US005665582A

United States Patent [19]
Kausch et al.

[11] Patent Number: 5,665,582
[45] Date of Patent: Sep. 9, 1997

[54] ISOLATION OF BIOLOGICAL MATERIALS

[75] Inventors: Albert P. Kausch, Stonington, Conn.; Sandya Narayanswami, Bar Harbor, Me.

[73] Assignee: Dekalb Genetics Corp., Mystic, Conn.

[21] Appl. No.: 229,288

[22] Filed: Apr. 18, 1994

Related U.S. Application Data

[63] Continuation-in-part of Ser. No. 605,852, Oct. 29, 1990, abandoned, which is a continuation of Ser. No. 146,434, Oct. 29, 1993, Pat. No. 5,508,164.

[51] Int. Cl.$^6$ .............................. C12N 7/02; C12N 11/06; C08B 37/04
[52] U.S. Cl. .................... 435/181; 435/820; 435/239; 536/3; 536/126
[58] Field of Search ........................ 435/239, 6, 29, 435/181, 820; 536/25.4, 3, 126

[56] References Cited

U.S. PATENT DOCUMENTS

| | | | |
|---|---|---|---|
| 3,970,518 | 7/1976 | Glaever | 435/239 |
| 4,454,234 | 6/1984 | Czerlinski | 436/526 |
| 4,710,472 | 12/1987 | Saur et al. | 435/287 |
| 4,904,391 | 2/1990 | Freeman | 210/695 |

FOREIGN PATENT DOCUMENTS

| | | | |
|---|---|---|---|
| 0 240 770 | 3/1987 | European Pat. Off. | G01N 33/553 |
| 0 339 980 | 4/1989 | European Pat. Off. | G01N 33/543 |
| 2 832 696 | 3/1978 | France | G01N 33/16 |
| WO86/05815 | 10/1986 | WIPO | C12Q 1/68 |
| WO89/04373 | 5/1989 | WIPO | C12Q 1/68 |
| WO90/07380 | 12/1989 | WIPO | C12Q 1/68 |
| WO90/06045 | 6/1990 | WIPO | G01N 33/543 |

OTHER PUBLICATIONS

Cashmore, A., Szabo, L., Timko, M., et al., "Import of Polypeptides into Chloroplasts." *Biotechnology*, vol. 3 (Sep. 1985), pp. 803–808.

Cooke, H. and Hindley, J., "Cloning of human satellite III DNA; different components are on different chromosomes," *Nucleic Acids Research*, vol. 6, No. 10 (1979), pp. 3177–3197.

Dahma, M., Giannaris, P., and Zabarylo, S., "An improved procedure for derivatization of controlled–pore glass beads for solid–phase oligonucleotide synthesis," *Nucleic Acids Research*, vol. 18, No. 13 (1990), pp. 3813–3821.

Dudin, G., Cremer, T., Schardin, M., et al., "A method for nucleic acid hybridization to isolated chromosomes in suspension," *Human Genetics*, vol. 76 (1987), pp. 290–292.

Dudin, G., Steegmayer, E., Vogt, P., et al., "Sorting of chromosomes by magnetic separation," *Human Genetics*, vol. 80 (1988), pp. 111–116.

Gengenbach, B., Green, C., and Donovan, C., "Inheritance of selected pathotoxin resistance in maize plants regenerated from cell cultures," *PNAS (USA)*, vol. 74, No. 11 (Nov. 1977), pp. 5113–5117.

Gruissem, W., Greenberg, B., Zurawski, G., et al., "Biosynthesis of Chloroplast Transfer RNA in a Spinach Chloroplast Transcription System," *Cell*, vol. 35 (Dec. 1983), pp. 815–828.

Hibberd, K., Walter, T., Green, C., et al., "Selection and Characterization of a Feedback–Insensitive Tissue Culture of Maize," *Planta*, vol. 148 (1980), pp. 183–187.

Howell, K., Gruenberg, J., Ito, A., et al., "Immuno–Isolation of Subcellular Components," in: Morre, D., et al. (eds). Cell–Free Analysis of Membrane Traffic (New York, Liss. 1988), pp. 77–90.

Hunter, J., Mills, G., and Sturrock, R., "Ferrography—a new method for isolation of particles from biological fluids," *Journal of Clinical Pathology*, vol. 35 (1982), pp. 689–690.

Kvalheim, G., Fodstad, O., Pihl, A., et al., "Elimination of B–Lymphoma Cells from Human Bone Marrow: Model Experiments Using Monodisperse Magnetic Particles Coated with Primary Monoclonal Antibodies," *Cancer Research*, vol. 47 (Feb. 1, 1987), pp. 846–851.

Lea, T., Vartdal, F., Davies, C., et al., "Magnetic Monosized Polymer Particles for Fast and Specific Fractionation of Human Mononuclear Cells," *Scand. J. Immunol.*, vol. 22 (1985), pp. 207–216.

Lehman, J., "Brave New Biosensors," *Biotechnology*, vol. 8 (Aug. 1990), pp. 729–731.

Manning, J., Hershey, N., Broker, T., et al., "A New Method of in situ Hybridization," *Chromosoma* (Berl.), vol. 55 (1975), pp. 107–117.

Margel, S., Beitler, U., and Ofarim, M., "Polyacrolein Microspheres as a New Tool in Cell Biology," *J. Cell Sci.*, vol. 56 (1982), pp. 157–175.

Margel, S., Zisblatt, S., and Rembaum, A., "Polyglutaraldehyde: A New Reagent for Coupling Proteins to Microspheres and for Labeling Cell–Surface Receptors. II. Simplified Labeling Method by Means of Non–Magnetic and Magnetic Polyglutaraldehyde Microspheres," *Journal of Immunological Methods*, vol. 28 (1979), pp. 341–353.

(List continued on next page.)

*Primary Examiner*—Mindy Fleisher
*Assistant Examiner*—James Ketter
*Attorney, Agent, or Firm*—Arnold, White & Durkee

[57] ABSTRACT

A method for the isolation and sorting of biological materials has been developed. Biological material includes chromosomes, segments of chromosomes, cell organelles, or other minute cellular components. The biological material is separated from the cellular milieu, if necessary, and anchored to a support. Examples of a support are glass coverslips, glass or polymer beads. The anchoring is by means of a reversible polymer and cross-linking system. The supported biological material may then be labelled with compositions capable of binding to said material, and with magnetic particles. Examples of the binding material include nucleic acid probes and antibodies. An example of the antibodies would be those directed to histones. Other labels, for example, fluorescein-biotin-avidin may be used. The material may be released from the support and sorted by a magnetic force. This method is an alternative to flow cytometry and presents numerous advantages in terms of time, resolution, purity, and preservation of the structure of the biological material during isolation and separation.

23 Claims, 31 Drawing Sheets
(8 of 31 Drawing(s) in Color)

OTHER PUBLICATIONS

Menz, E. Havelick, J., Groman, E., et al., "Magnetic affinity chromatography: An emerging technique," *American Biotechnology Laboratory* (Sep./Oct. 1986).

Miltenyi, S., Muller, W., Weichel, W., et al., "High Gradient Magnetic Cell Separation with MACS," *Cytometry*, vol. 11 (1990), pp. 231–238.

Molday, R., Yen, S., and Rembaum, A., "Application of magnetic microspheres in labelling and separation of cells," *Nature*, vol. 268 (Aug. 4, 1977), pp. 437–438.

Morimoto, Y., Okumura, M., Sugibayashi, K., et al., "Biomedical Applications of Magnetic Fluids. II. Preparation and Magnetic Guidance of Magnetic Albumin Microsphere for Site Specific Drug Delivery In Vivo," *J. Pharm. Dyn.*, vol. 4 (1981), pp. 624–631.

Morimoto, Y., Sugibayashi, K., and Akimoto, M., "Magnetic Guidance of Ferro–colloid–entrapped Emulsion for Site-Specific Drug Delivery," *Chem. Pharm. Bull.*, vol. 31, No. 1 (1983), pp. 279–285.

Mosbach, K., and Anderson,L., "Magnetic ferrofluids for preparation of magnetic polymers and their application in affinity chromatography," *Nature*, vol. 270 (Nov. 17, 1977), pp. 259–261.

Mosbach, K., and Schroder, U., "Preparation and Application of Magnetic Polymers for Targeting of Drugs," *FEBS Letters*, vol. 102, No. 1 (Jun. 1979), pp. 112–116.

Narayanswami, S., and Hamkalo, B., "High Resolution Mapping of *Xenopus laevis* 5S and Ribosomal RNA Genes by EM In Situ Hybridization," *Cytometry*, vol. 11 (1990), pp. 144–152.

Narayanswami, S., Kausch, A., and Hamkalo, B., "Reversible Immobilization of In–Situ Hybridized Chromosomes. A New Approach to Chromosome Sorting," (1990), 4th Intl. Workshop on Mouse Genome Mapping, Annapolis, MD, Nov. 4–8 (Abstract).

Padmanabhan, R., Corsico, C., Howard, T., et al., "Purification of Transiently Transfected Cells by Magnetic Affinity Cell Sorting," *Analytical Biochemistry*, vol. 170 (1988), pp. 341–348.

Pain, D., Kanwar, Y., and Blobel, G., "Identification of a receptor for protein import into chloroplasts and its localization to envelopes contact zones," *Nature*, vol. 331 (Jan. 21, 1988), pp. 232–237.

Rembaum, A. and Dreyer, W., "Immunomicrospheres: Reagents for Cell Labeling and Separation," *Science*, vol. 208 (Apr. 25, 1980), pp. 364–368.

Richa, J. and Lo, C., "Introduction of Human DNA into Mouse Eggs by Injection of Dissected Chromosome Fragments," *Science*, vol. 245 (July 14, 1989), pp. 175–177.

Schroder, U., Segren, S., Gemmefors, C., et al., "Magnetic carbohydrate nanoparticles for affinity cell separation," *Journal of Immunological Methods*, vol. 93 (1986), pp. 45–53.

Senyei, A. and Widder, K., "Drug Targeting: Magnetically Responsive Albumin Microspheres—A Review of the System to Date," *Gynecologic Oncology*, vol. 12 (1981), pp. 1–13.

Senyei, A., Widder, K., and Czerlinski, G., "Magnetic guidance of drug–carrying microspheres," *J. Appl. Phys.*, vol. 49, No. 6 (Jun. 1978), pp. 3578–3583.

Spangrude, G., Heimfeld, S., and Weissman, I., "Purification and Characterization of Mouse Hematopoietic Stem Cells," *Science*, vol. 241 (1988), pp. 58–62.

Staros, J., "N–Hydroxysulfosuccinimide Active Esters: Bis-(N–hydroxysulfosuccinimide) Esters of Two Dicarboxylic Acids Are Hydrophillic, Membrane–Impermeant, Protein Cross–Linkers," *Biochemistry*, vol. 21 (1982), pp. 3950–3955.

Uhlen, M., "Magnetic separation of DNA," *Nature*, vol. 340 (Aug. 31, 1989), pp. 733–734.

Viegas–Pequignot, E., Dutrillaux, B., Magdelenat, H., et al., "Mapping of single–copy DNA sequences on human chromosomes by in situ hybridization with biotinylated probes: Enhancement of detection sensitivity by intensified–fluorescence digital–imaging microscopy," *Proc. Natl. Acad. Sci. USA*, vol. 86 (Jan. 1989), pp. 582–586.

Waye, J., Durfy, S., Pinkel, D., et al., "Chromosome-Specific Alpha Satellite DNA from Human Chromosome 1: Hierarchical Structure and Genomic Organization of a Polymorphic Domain Spanning Several Hundred Kilobase Pairs of Centromeric DNA," *Genomics*, vol. 1 (1987), pp. 43–51.

Widder, K., Senyei, A., Burchette, J., et al., "A Rapid Method for Immunofluorescent Staining of Paraffin Sections Using Iron–containing Protein A Microspheres," *Journal of Histochemistry and Cytochemistry*, vol. 29, No. 7 (1981), pp. 870–873.

Widder, K., Senyei, A., and Ranhey, D., "Magnetically Responsive Microspheres and Other Carriers for the Biophysical Targeting of Antitumor Agents," *Advances in Pharmacology and Chemotherapy*, vol. 16 (1979), pp. 213–271.

Widder, K., Senyei, A., and Scarpelli, D., "Magnetic Microspheres: A Model System for Site Specific Drug Delivery in Vivo," *Proceedings of the Society for Experimental Biology and Medicine*, vol. 58 (1978), pp. 141–146.

Wu, D. and Walters, R., "Protein Immobilization on Silica Supports: A Ligand Density Study," *Journal of Chromatography*, vol. 458 (1988), pp. 169–174.

Narayanswami, S., Lundgren, K., and Hamkalo, B., "Deoxyribonucleic Acid Sequence Mapping on Metaphase Chromosomes by Immunoelectron Microscopy," *Scanning Microscopy Supplement*, vol. 3 (1989), pp. 65–76.

Schreier et al., "Plant Molecular Biology Manual B5", Eds., S.B. Gelvin & R.A. Schilperpoort, Kluwer Academic Publishers, Dordrecht, 1988, pp. 5–10.

Hutchinson et al., *J. Cell. Biol.*, 95:609–618, 1982.

Celeda, R.K.A. et al., "Magnetic Separation of Chromosome 1 from Human Lymphocytes," *European Journal of Cell Biology*, 51 (Supp. 30):20, Abstract pp. 1–7, 1990.

Franzusoff, et al., "Immuno–Isolation of Sec7p–Coated Transport Vesicles from the Yeast Secretory Pathway," *Nature*, 355:173–175, 1992.

Liberti and Feeley, "Analytical—and Process–Scale Cell Separation with Bioreceptor Ferrofluids and High–Gradient Magnetic Separation," Cell Separation Science and Technology, Eds., D.S. Kompala and P. Todd, Chapter 17..pp. 268–287, 1990.

Schnell et al., "The Chloroplast Import Receptor Is an Integral Membrane Protein of Chloroplast Envelope Contact Sites," *The Journal of Cell Biology*, 111:1825–1838, 1990.

International Search Report, mailed 18 Mar., 1992.

Anderson, L. and Mosbach, K., "Magnetic Ferrofluids for Preparation of Magnetic Polymers and Their Application in Affinity Chromatography," *Nature*, 270:259, 1977.

Dudin, G. et al., "A Method for Nucleic Acid Hybridization to Isolated Chromosomes in Suspension," *Hum. Genet.* 76:290–292, 1987.

Eicher, E.M. et al., "The mouse Y* chromosome involves a complex rearrangement, including interstitial positioning of the pseudoautosomal region," *Cyto. Cell Genet.*, 57:221–230, 1991.

Eicher, E.M. et al., "A repeated segment on the mouse Y chromosome is composed of retroviral-related, Y-enriched and Y-specific sequences," *Genetics*, 122:181–192, 1989.

Gould, A.P. et al., "Targets of homeotic gene control in Drosophila," *Nature*, 348:308–312, 1990.

Harris, P. et al., "Mapping by Chromosome Sorting of Several Gene Probes Including C–myc, to the Derivative Chromosomes of a 3;8 Translocation Associated with Familial Renal Cancer," *Cytometry*, 7:589–594, 1986.

Hormes, E. and Korsnes, L., "Magnetic DNA hybridization properties of oligonucleotide probes attached to superparamagnetic beads and their use in the isolation of poly (A) mRNA from eukaryotic cells," *GATA*, 7(6):145–150, 1990.

June, C. et al., "T–Cell Proliferation Involving the CD28 Pathway is Associated with Cyclosporine–Resistant Interleukin–2 Gene Expression," *Molecular and Cell Biology*, 7:4473, 1987.

Moser, H.E., and Dervan, P.B., "Sequence–specific cleavage of double helical DNA by triple helix formation," *Science*, 238:645–650, 1987.

Narayanswami, S. et al., "Cytological and molecular characterization of centromeres in *Mus domesticus* and *Mus spretus*," *Mamm. Gen.*, 2:186–194, 1992.

Ranney, D.F. et al., "Magnetically Responsive Microspheres and Other Carriers for the Biophysical Targeting of Antitumor Agents," *Advances in Pharmacological Chemotherapy*, 16:213, 1979.

Rikke, B.A. et al., "Systematic Identification of LINE–1 Repetitive DNA Sequence Differences Having Species Specificity Between *Mus spretus* and *Mus domesticus*," *J. Mol. Biol.*, 219:635–643, 1991.

Widder K. J. et al., "Magnetic Microspheres: A Model System for Site Specific Drug Delivery in Vivo," *Proceedings of the Society for Experimental Biology and Medicine*, 58:141, 1978.

Trendelenburg, M.F. and Gurdon, J.B., "Transcription of cloned Xenopus ribosomal genes visualized after injection into oocyte nuclei," *Nature*, 276:292–294, 1978.

Weber, J. et al., "Microdissection and Microcloning of Human Chromosome 7g22–32 Region," *Somat. Cell and Mol. Genet.*, 16(2):123–128, 1990.

Wong, A.K.C. et al., "The chromosomal distribution of the major and minor satellite is not conserved in the genus *Mus*. *Chromosoma* " (Berl), 99:190–195, 1990.

Ito, T. et al., "Sequence–specific DNA purification by triplex affinity capture," *Proc. Natl. Acad. Sci. USA*, 89:495–498, 1992.

Sherwood, J. K., et al., "Controlled antibody delivery systems," *Bio/Technology*, 10:1446–1449, 1992.

-B- Biotin Labeled DNA, hybridized

Y Rabbit anti-biotin IgG

✱ Colloidal gold tagged with IgG against rabbit

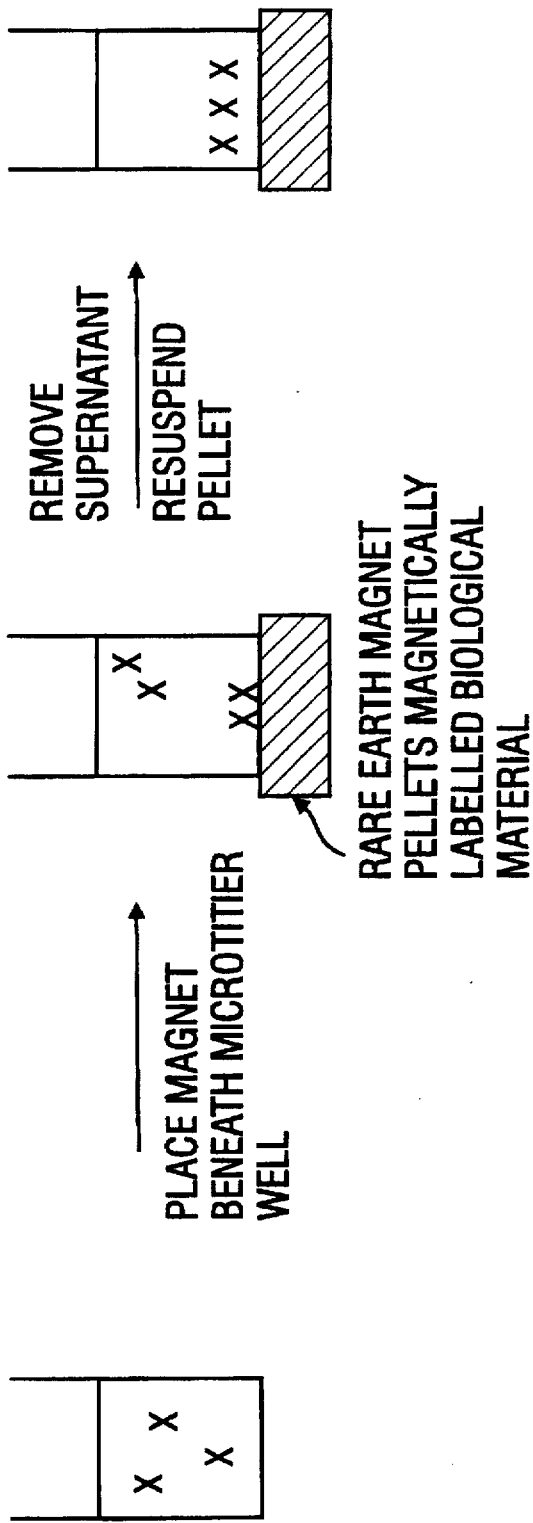

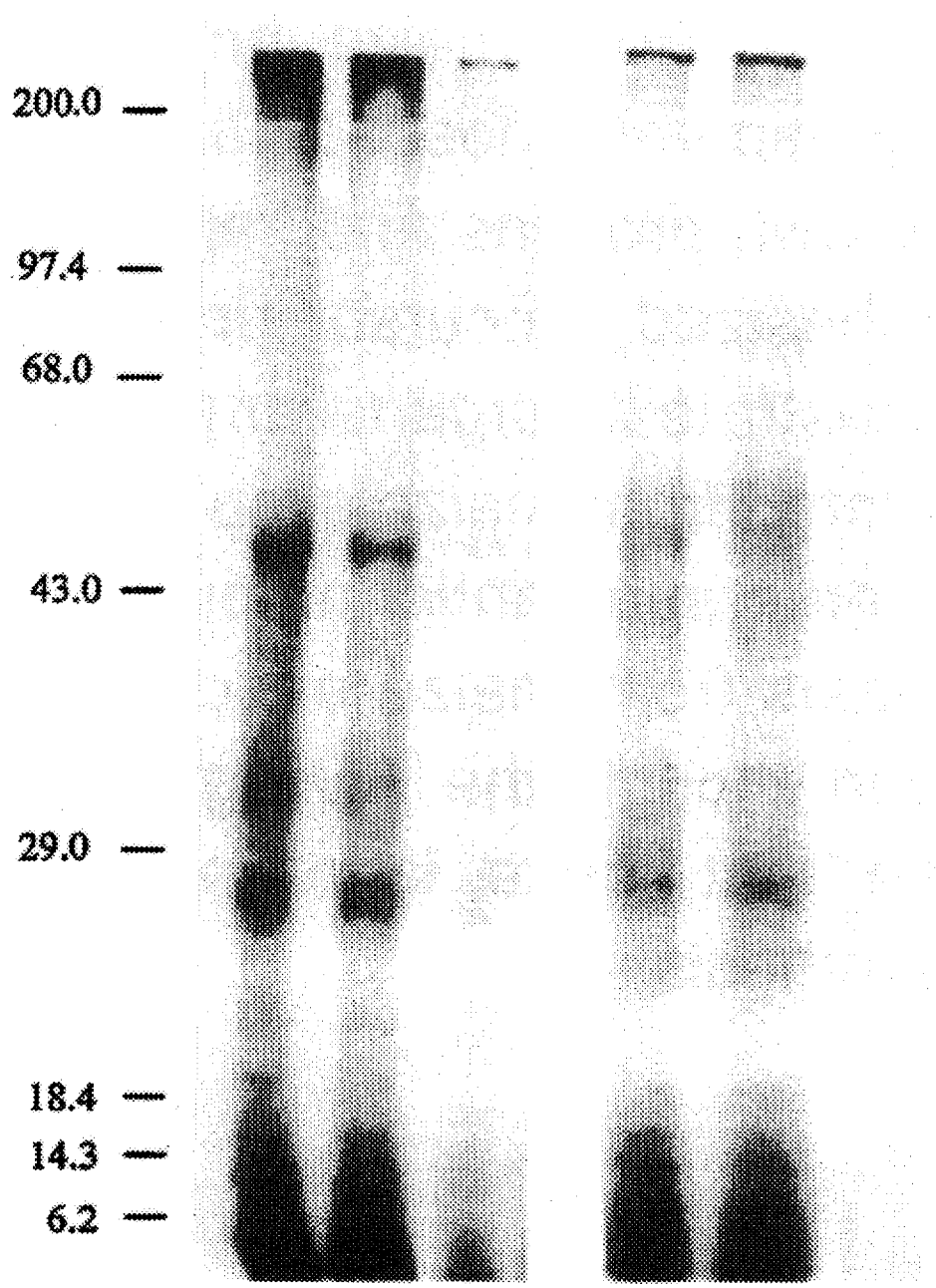

|                      | + | - | - | + | - | - |
|----------------------|---|---|---|---|---|---|
| NO INHIBITOR         | + | - | - | + | - | - |
| 100μM CYCLOHEXIMIDE  | - | + | - | - | + | - |
| 100μM CHLORAMPHENICOL| - | - | + | - | - | + |

ISOLATION OF BIOLOGICAL MATERIALS

The present application is a continuation-in-part of U.S. Ser. No. 07/605,852, filed Oct. 29, 1990, now abandoned in favor of file wrapper continuation application U.S. Ser. No. 08/146,434, filed Oct. 29, 1993.

The government may own certain rights in the present invention pursuant to grant number NIH GM 23241.

BACKGROUND OF THE INVENTION

1. Technical Field of the Invention

This invention relates to the development of an efficient, high yield method for the physical purification of specific biological material. This invention relates particularly to a method for separating and isolating biological materials by labelling the biological materials with a binding composition. The material to be labelled can be reversibly anchored to a support before labeling. A binding composition preferably comprises an indicator such as a luminescent material or a magnetic particle. Contemplated indicators are appropriate for use in separating and isolating biological material in the microscopic range, e.g. chromosomes, mitochondria, chloroplasts, Golgi apparatus and other cellular organelles. A binding composition is preferably a nucleic acid probe or an antibody. After release from the support, the labelled material is isolated by sorting by means of the indicator.

2. Background of the Invention

Cells are composed of heterogeneous components. Individual components need to be separated prior to many investigations and procedures. Separation methods vary depending on the absolute and relative sizes of the material to be separated, and the degree of purity which must be achieved. To separate relatively large biological materials, that is, the "meat" of the stew, centrifugation, filtering and density gradient sedimentation are some of the relatively crude methods that are appropriate. To separate small, minute cellular components, the "spices" (e.g., chromosomes) flow cytometry has been used. Some materials, e.g., the Golgi apparatus, have not been satisfactorily separated by any means as an individual, intact cellular component.

Major efforts are currently being made to map and sequence the genomes of man, mouse, and several other selected organisms. Although genetic mapping methods can tell us a great deal about the organization of a genome, it is also necessary to isolate chromosome-specific DNA to obtain contiguous DNA sequence information and construct a physical map. This is usually done by cloning or screening cosmid, YAC, or the recently developed P1 libraries (Burke et al., 1991; Sternberg, 1992). However, the usefulness of all libraries is subject to specific limitations of insert size and cloning bias, i.e., the mouse genome contains DNA sequences that are apparently resistant to cloning in either *E. coli* or yeast (Little, 1990; Gibson et al., 1987). It is also now known that high levels of rearrangement and deletion occur frequently within YAC clones (Little, 1990).

A physical purification method would permit the isolation and sequencing of DNA that is otherwise unstable in conventional hosts. In addition, effective chromosome purification combined with chromosome breakage methods such as microdissection (Weber et al., 1990) or the use of artificial restriction enzymes (Moser et al., 1987), would in theory allow the construction of libraries for specific chromosomal subregions such as centromeres, repeated genes, translocation breakpoints, or the rearrangements involved in neoplastic progression. Applications of the present invention are not limited to the types of experiment outlined above, however. Even where straightforward library construction is the goal, physical purification methods will permit the rapid construction of highly enriched libraries, increasing the efficiency with which desired sequences can be cloned. This technology is applicable to many species besides the mouse and would be of great utility in the analysis of the human genome.

Various organelles and intracellular structures have proven difficult or impossible to isolate or purify by traditional cell fractionation methods such as density sedimentation. In addition, existing procedures for routine organelle isolations may disrupt or impair their physiology, and in some cases provide populations of organelles which are not developmentally representative (Dahlin and Cline, 1991). Antibodies specific to exposed epitopes on many intracellular compartments and structures have been reported (e.g. Ohba and Schatz, 1987; Pain et al., 1988; Yoneda et al., 1988;) and their specificity has been demonstrated immunocytochemically.

Most currently applied cell fractionation procedures exploit obvious differences in physical parameters between organelles and rely on centrifugation which generates large, damaging shear forces. Consequently, it is difficult to prepare physiologically intact subcellular fractions where only minor differences exist in physical properties or when the compartments are especially fragile to shear. Furthermore, most existing procedures for routine organelle isolations are lengthy, rendering some physiological observations difficult. The study of plastids and their metabolism has focused on mature green chloroplasts with considerably less attention given to the chloroplast developmental sequence from proplastids and even less to research on nongreen plastids (e.g. chromoplasts, amyloplasts, etc.). In many cases the nongreen plastids have a distinct metabolism which provides a superior physiological system for the study of many plant processes, such as carotenoid biosynthesis in chromoplasts, or starch synthesis in amyloplasts. Although intact mature green chloroplasts can be readily isolated by density sedimentation, the study of nongreen plastids has been encumbered by their fragile properties and difficulties in isolation from the tissues in which they develop.

Immunoabsorption of subcellular components by organelle specific antibodies bound to an appropriate [solid phase] support obviates some of these difficulties (Howell et al., 1988) and provides the possibility for separation from whole cell lysates by specific biochemical criteria. Various preparations of magnetic particles with distinct magnetic properties, surface characteristics, and mean diameter size ranges have been produced (Haukanes and Kvam, 1993.) These differences significantly influence their specific utility for biological separations, and even though magnetic cell purifications were achieved several years ago, magnetic particles with the necessary qualities needed for other types of separations were developed only very recently (Haukanes and Kvam, 1993).

Superparamagnetic (magnetic only in a magnetic field) microparticles (sized in the micron range) are synthesized by polymerizing polystyrene or polyacrolein in the presence of a magnetite ferrofluid (Ugelstad and Berge, 1988) or by formation of an agglomerate by silanation of a ferrofluid (Whitehead et al., 1985). With both of these preparations antibodies can be covalently coupled by the resultant surface character of the particles. Magnetic microparticles have been used in cell separation, immunoassays, isolation, identification and genetic analysis of specific nucleic acid sequences, and for isolation of DNA binding proteins (Haukanes and Kvam, 1993). The present inventors have examined the possibility of using similar magnetic microparticles as a solid support for immunoabsorption of intact plastids from whole cell lysates because their relatively high magnetic moment allows ease of separation using simple rare earth magnets.

Another class of particle preparations can be described as magnetic nanoparticles (ferrofluid derivatives sized in the nanometer range) consisting of ferric oxide crystals encapsulated by dextran (Molday and MacKenzie, 1982), which are activated with cyanogen bromide and subsequently coupled to protein preparations with diaminohexane. Magnetic nanoparticles have been shown to have a much faster binding reactivity than magnetic microparticles for intact mammalian cell separations (Miltenyi et al., 1990; Liberti and Feeley, 1991), hence greater specificity, and they do not aggregate in a magnetic field. The small size of nanoparticle preparations renders them applicable for subcellular immunolocalizations by allowing the antibodies carried by the particles to react with all exposed epitopes over the entire surface of the organelle. The immunoreactions occur as rapidly as if free in solution with a minimal degree of stearic hindrance compared with larger solid phase surfaces which can only react with a tangential surface. However, magnetic nanoparticles have an extremely low magnetic moment since the subparticles of ferromagnetic material are smaller than the domain size required for rapid magnetic precipitation and therefore, migrate only very slowly in conventional ferromagnetic fields. Consequently, organelles labelled with magnetic nanoparticles must be separated in a magnetic affinity column (Miltenyi et al., 1990). Disclosed herein is the use of antibodies specific to exposed epitopes of proteins on chloroplast outer envelopes coupled to magnetic nanoparticles to immuno-isolate various plastid subtypes from whole cell lysates.

Although there are many variations on the flow cytometry theme, the basic principle of this method is to label the cellular material, for example, chromosomes, according to its DNA content, which will be generally correlated with size, and to separate the material into collecting tubes by laser beams that quantitatively measure the DNA content. Flow separation of human chromosomes has been somewhat successful in completely separating some of the 23 pairs of chromosomes but has resulted in some aggregation of chromosomes of similar sizes, e.g., the human chromosomes 21-22 and Y. Therefore, this method is of limited usefulness.

Flow cytometry techniques are used for both analysis and sorting of biological macromolecules and cells (Darzynkiewicz & Crissman, 1990). Flow cytometry currently is the primary method for the purification of specific chromosomes. However, this method suffers from several drawbacks, and its efficacy is limited by the amount of time (hours or even days) required to sort large quantities of a single chromosome. For example, it is not yet possible to reliably separate different chromosomes whose DNA contents are similar and there is some cross-contamination of chromosomes having similar sizes.

Furthermore, flow cytometry techniques cannot be employed to separate individual chromosomes by DNA content alone in species such as the mouse whose karyotype consists of similarly sized telocentric chromosomes (these are chromosomes with their primary constrictions, the centromeres, located at one end). In such cases, somatic cell hybridization may be employed, although this is very laborious. In somatic cell hybridization, chromosomes may be isolated in a genetically different background by cell fusion and selection.

Although some attempts at developing physical isolation methods have been made (Dudin et al., 1988; Kandpal et al., 1990), there is no effective method for obtaining purified mouse chromosomes. Flow cytometry is currently the only available method for physically isolating specific whole chromosomes (Carrano et al., 1979). Maps constructed by analyzing cosmid libraries derived from flow-sorted material are currently being used for the analysis of the human genome (Van Dilla et al., 1989). Flow sorting is not generally feasible for mouse chromosomes, however, due to their uniform DNA content. Somatic cell hybrids containing a given chromosome, or cell types with nonstandard karyotypes, such as are found in mouse strains carrying single Robertsonian translocation chromosomes, have been used to differentiate the DNA content of mouse chromosomes. Furthermore, the efficacy of flow cytometry is limited by the time required to sort large quantities of a given chromosome. Finally, debris and cross contamination in sorted preparations limit their utility. Thus an alternative to FACS must be available before easy purification of mouse chromosomes can become a reality.

The availability of chromosome-specific, repetitive sequence hybridization probes (Moyzis et al., 1987) presents the possibility of a unique alternative method for chromosome isolation. The combination of in-situ hybridization of such probes, appropriately labelled (Narayanswami et al., 1992), to chromosome mixtures, followed by isolation based on the presence of the hybridized probe, should permit isolation of a specific chromosome without flow sorting. There has been one attempt to develop such a technique (Dudin et al., 1988). In that report, in-situ hybridization was carried out on suspensions of chromosomes prepared as for flow cytometry. Hybrids were labelled with large magnetic beads several microns in diameter. However, that approach was not very successful due to problems with adventitiously adsorbed contaminants, chromosome aggregation, and losses during centrifugation steps.

SUMMARY OF THE INVENTION

An important embodiment of the present invention is a method of reversibly anchoring a biological material to a solid support. The solid support may be any acceptable solid material, with the most preferred being glass, as in a glass coverslip or controlled pore glass beads. It is an embodiment of the invention that the biological material, once anchored, can be separated from unanchored materials by a variety of methods. The invention offers particular advantages in the separation or labeling of materials that are not easily separated by methods such as centrifugation, gel chromatography or electrophoresis due to constraints of size or fragility.

The present invention also comprises an improvement in the reversible anchoring of biological materials in that a reversible polymer is anchored to the solid material and the linker is attached to the polymer. This improvement overcomes steric hindrances that may arise when the linker is directly attached to the solid support and results in improved labeling and activity of the anchored biological material.

The preferred method for reversibly anchoring a biological material to a solid support described by the present invention comprises the steps of placing a reversible polymer onto the solid support, attaching a reversible linker to the polymer and linking the biological material to the reversible linker to reversibly anchor the biological material to the solid support. The method may also further comprise releasing the biological material.

A polymer is a compound formed by the joining together of small molecules to make often, very large molecules. The large molecule is called a polymer, and the simple molecules from which polymers are made are monomers. Two types of polymers that may be used as a part of the present invention are homopolymers, in which all the monomers are the same, and heteropolymers in which two or more types of monomers are joined in the polymer.

Polymers that may be used as a part of the present invention include, but are not limited to stable polymers such as polyethylene-co-vinyl acetate (EVAc) and the like, which are not reversible but can incorporate proteins, polyanhidride copolymer of stearic acid dimer and sebacic acid (p(SAD:SA)), polyglycolate or polylactate and combinations thereof and alginate, with alginate, lactide or glycolate polymers being preferred, and alginate being the most preferred.

The linker, or crosslinker of the present invention may be homobifunctional linker and is preferably a heterobifunctional linker that is joined to the polymer at one functional end and to the biological material at the other functional end. The crosslinker may be any linker that is reversibly joined and a representative list includes DTSSP, SPDP, SAED, SMPT, DPDPS, DSP, BSOCOES, EGS, APDP, DTBP, BASED or SADP, with the most preferred being DTSSP or SPDP.

It is understood that the reversing agent for both the polymer and the linker is preferably an agent that does not affect the biological material that is being anchored. For example, DTSSP is reversible by thiol reduction, BSOCOES is base cleavable and EGS and sulfo-EGS are cleavable by hydroxylamine. Periodate cleavable linkers also may be used in the practice of the invention, but may have adverse affects on biological materials. Polymers such as alginate are reversible by $Ca^{2+}$. Therefore a polymer and linker is chosen with a reversing agent that is compatible with the biological material to be anchored.

The biological material of the present invention may comprise DNA, RNA or protein, and may also comprise lipids, carbohydrates or combinations of any of these. In certain embodiments, the biological material may be a cellular component such as chromosomes or fragments thereof. In still further embodiments, the biological material may be a cell organelle such as a vesicle, chloroplast, plastid, nucleus, mitochondria, endoplasmic reticulum or a golgi apparatus.

The present invention contemplates a binding composition which can bind to the biological material. The binding composition of the present invention may be any composition that will bind to or associate with the biological material. The binding may be by any means, including ionic, covalent, noncovalent, electrostatic, magnetic, by Van der Waals attraction, hydrophobic interaction or by any other acceptable means. In certain embodiments, the binding will be specific, i.e. antibody/antigen recognition or nucleic acid hybridization and in other embodiments, the binding will be non-specific. The binding composition may also comprise a means of separating or labeling the biological material.

The binding composition may comprise, for example nucleic acid probes which hybridize to a unique sequence of a specific chromosome such as the unique telomeric region, NOR region of the chromosome of interest or to sequences scattered throughout specific chromosome arms. Such a nucleic acid molecule may comprise either RNA or DNA from any source and may be in single stranded or double stranded form and may comprise a triple helix forming molecule. In the case of double stranded binding composition or biological material, the nucleic acids may require "melting" or being rendered single stranded before binding will occur. The binding may be a specific hybridization such as a nucleic acid sequence that preferentially hybridizes to a particular chromosome, or a non-specific interaction, or it may comprise the formation of a triple helix between a double stranded and a single stranded nucleic acid molecule.

In certain embodiments, the binding composition will comprise an antibody or an anti-idiotypic antibody, biotinylated antibody or protein A and binding may be directed to an epitopic marker that is inherent on the biological material or that has been previously bound to the biological material by a second antibody, for example. Furthermore, the antibody can be a monoclonal antibody. The antibody can be directed to a nucleic acid sequence, a protein sequence or a cellular component.

The binding composition may further comprise an indicator Such as a luminescent indicator, a radioactive indicator, or an electron opaque indicator, such as i.e. colloidal gold, with a preferred indicator being a fluorescent indicator, so that the binding can be detected by some means. Preferred means of detecting include, but are not limited to fluorescence, autoradiography and electron microscopy.

The binding composition may also comprise magnetic particles or paramagnetic particles. In certain embodiments, the binding composition will comprise magnetic particles that are from about 2 nm to about 10 microns in diameter and preferably are from about 2 nm to about 2 microns in diameter. In certain embodiments, the magnetic particles provide a means of separating the biological material after it has been released from the solid support by exposure to a magnetic field, for example. By way of example, the magnetic particles may be further joined to an indicator such as colloidal gold, for example, and are preferably ferric oxide joined to colloidal gold.

Therefore, in certain embodiments, the present invention is a method for reversibly anchoring a biological material to a solid support, comprising the steps of placing a reversible polymer onto the solid support, attaching a reversible linker to the polymer, linking the biological material to the reversible linker to reversibly anchor the biological material to the solid support, releasing the biological material by reversing both the reversible polymer and the reversible crosslinker, and obtaining the biological material therefrom.

The present invention also contemplates a kit for reversibly anchoring a biological material to a solid support. The kit would comprise a reversibly polymerizable material, a linker material and a container means. The kit may further comprise a means of reversing the polymerized material and a means of releasing the linker. The kit may further comprise a binding composition that may include a label.

It is understood that the kit of the present invention may also include a solid support such as a coverslip or controlled pore glass beads and that these supports may be pretreated to bind to the polymer, or may comprise bound polymer and/or linkers.

The reagents of the kit can be provided as liquid solutions, attached to a solid support or as dried powders. When a reagent provided is a dry powder, the powder can be reconstituted by the addition of a suitable solvent. The solvent can be provided.

The container means will generally include vials into which the compositions may be placed, and preferably suitably aliquotted. The kits of the present invention will also typically include a means for containing the reagent containers in close confinement for commercial sale. Such containers may include injection or blow-molded plastic containers into which the desired vials are retained.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

Other objects and advantages of the invention will become apparent upon reading the following detailed description and upon reference to the drawings in which:

FIG. 11 shows the steps in the procedure to pellet, rinse and purify (sort) the magnetically labelled biological material after it has been released from the support by a releasing agent, for example, DTT.

FIG. 17A is an electron micrograph of a single chromatid of a mitotic chromosome from an insect (Oncopeltus) treated to reveal loop chromatin fibers that emanate from the central axis of the chromatid.

FIG. 17B is a schematic illustration of the many orders of chromosome packing postulated to give rise to the highly condensed metaphase chromosome.

FIG. 19A illustrates the dose dependent recovery of prefractionated pea leaf chloroplasts labelled with various amounts of $\alpha$-OM and immunoabsorbed to equal amounts of streptavidin nanoparticles. This data indicates saturation and optimal recovery at 300 µg/ml.

FIG. 19B illustrates the optimization of flow rate through the magnetic affinity column with various controls. This data indicates minimal recovery of non-specifically labelled chloroplasts while still retaining the highest number of specifically labelled chloroplasts at 300 µl/min.

FIG. 19C illustrates depletion of chloroplasts from samples with increasing numbers of chloroplasts. This data indicates a concentration dependence and saturation of 200 µg/ml chlorophyll.

FIG. 20A is a typical affinity column used for recovery of nanoparticle labelled organelles.

FIG. 20B is magnetically immunoabsorbed pea chloroplasts adhered to the steelwool matrix.

FIG. 20C is elution of isolated plasmids by gentle backflushing of the column after brief demagnetization.

FIG. 20D is a differential interference contrast and phase contrast microscopy of magnetically immunoabsorbed cell fractions from whole cell lysates indicating that the chloroplast preparations were free of contaminating cell structures.

FIG. 20E is a differential interference contrast and phase contrast microscopy of magnetically immunoabsorbed cell fractions from whole cell lysates indicating that the amyloplast preparations were free of contaminating cell structures.

FIG. 20F is a differential interference contrast and phase contrast microscopy of magnetically immunoabsorbed cell fractions from whole cell lysates indicating that the chromoplast preparations were free of contaminating cell structures.

FIG. 20G is a transmission electron microscopy of magnetic nanoparticles adhered to the outer envelope of pea chloroplasts.

FIG. 20H is a transmission electron microscopy of magnetic nanoparticles adhered to the outer envelope of pea chloroplasts.

FIG. 23A is in organellar protein synthesis by prefractionated (intact) pea chloroplasts after magnetic immunoabsorption with nanoparticles from Percoll gradients.

FIG. 23B is in organellar protein synthesis by prefractionated (intact) maize chloroplasts after magnetic immunoabsorption with nanoparticles from Percoll gradients.

Figure 1:
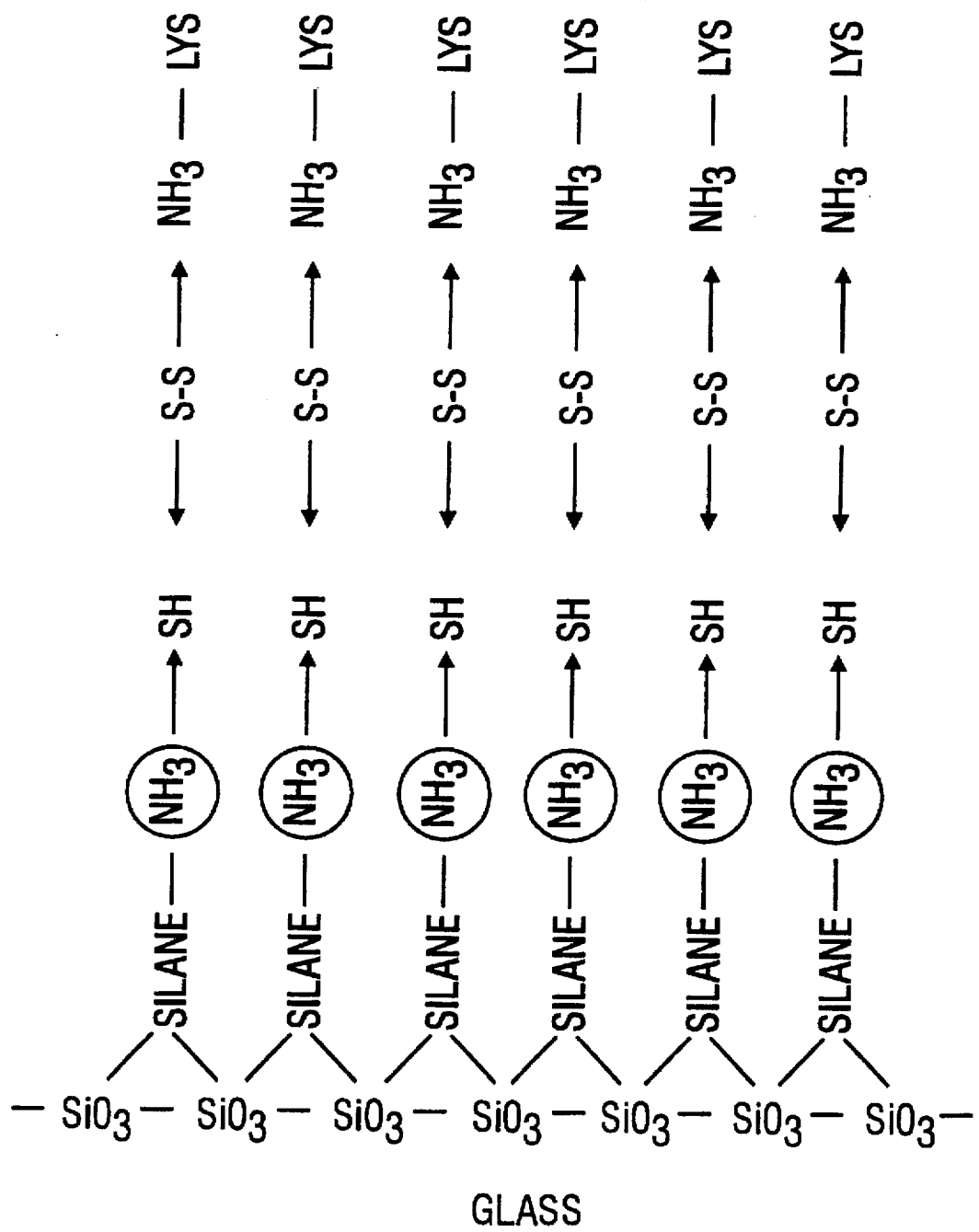
FIG. 1 is a representation of a reversible linkage between a chromosome and a support in the form of a piece of glass, for example, a coverslip.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

I. The Invention

The present invention relates to a method for the separation and isolation of a biological material. The method includes the steps of anchoring the biological material to a support to immobilize it, and labelling the anchored biological material with a binding composition which is capable of binding to it. The purpose of the labelling is to take advantage of inherent differences in the biological material with regard to complexing with the binding material and to subsequently forming the basis for separation. The biological material-binding composition is preferably attached to an indicator and that indicator is used to separate and isolate the material.

More specifically, the invention described herein relates to methods of separating and isolating small biological materials. This is achieved by: (1) reversible immobilization or anchoring of biological materials, such as cellular organelles, chromosomes or segments thereof, supernumerary chromosomes, such as B-chromosomes, plasmids, artificial chromosomes, mitochondria, vesicles, chloroplasts, and Golgi apparatus on a support; followed by (2) labelling of these structures with a binding composition such as nucleic acid probes complementary to DNA or RNA within the material, with antibodies, or with antibody-biotin steptoavidine complexes or similar detection systems. Such antibodies may be directed for example, to proteins within the materials or exposed on their surfaces; (3) combining the labelled materials with an indicator; (4) isolating individual components or classes of components of the biological material by reversal of the immobilization step; and (5) separating the labelled material from the non labelled material through the use of the indicator.

An important and unique aspect of this invention is that materials are labelled while they are anchored to a solid support, and then released to facilitate sorting. Another important aspect is that the indicator used is small relative to the biological material so that steric hindrance is not a problem, cross-aggregation is minimized, the structure of the biological material is preserved, and resolution of the signal/target is improved.

A. Biological Material

As used herein, the term "biological material" means any material obtained from an organism and, preferably a cell. A method of this invention is applicable to any biological material, although it is most advantageous for cellular organelles, cellular components and molecules, and particularly, for small cellular organelles, small cellular components and molecules. Examples of these are chromosomes or segments thereof, double minute chromosomes, supernumerary chromosomes, plasmids, artificial chromosomes, cell organelles, such as mitochondria, intact nuclei, chloroplasts, and cell structures such as the Golgi apparatus, ribosomes, synaptosomal complexes, microtubule organizing centers, vacuoles, vesicles, and the like.

It is contemplated that a cell from any source can be used to provide biological materials for use in the present invention. Preferred examples include tumor cells such as HeLa cells, human LAK cells (lymphokine activated killer cells), cells of PHA stimulated human peripheral blood, bone marrow cells, plant callus cells, plant protoplasts, and the like. Generally, cells which are capable of giving rise to detectable amounts of biological material are preferable.

Means for obtaining biological material from cells and organisms are well known in the art. By way of example, chromosome preparations are made as described in Narayanswami et al. (1989) with minor modifications. These methods are modifications of that proposed by Miller (1969). In one embodiment, mouse L929 cells are arrested with 50–80 ng/ml Colcemid (Gibco) overnight. Cells at metaphase of the mitotic cycle are collected by shaking them off the bottom of the culture vessel and lysing them in the presence of 0.5% Nonidet P-40. After 1 min. at room temperature, the chromosome suspension is layered over a cushion of 1M sucrose, at about pH 8.5 in the cap of a 15 ml Falcon tube. The cap contains a glass coverslip that had previously been silanated and prefixed with the thiol-cleavable crosslinking agent dithiobis-sulfa succinimidyl propionate (DTTSP). Preparations were centrifuged as described in Narayanswami et al. (1989). The coverslips are removed from the microcentrifugation chambers, and rinsed briefly in 0.4% Kodak Photoflo 200, at about pH 8.5, followed by about a 5 min. rinse in 2×SSC, 150 mM glycine, to quench the crosslinker. The preparations are kept moist with the solution in use.

Chromosomes are conventionally numbered, usually in decreasing order according to size as determined microscopically at metaphase. It is important to be able to analyze the chromosomal composition of a cell, cell line, tissue or organism, because deviations from the correct number of chromosomes usually produce phenotypic abnormalities. The phenotype results from the interaction of the genetic complement and the environment. Structural chromosomal aberrations may also produce abnormalities, if the genetic balance is disrupted. Chromosomal aberrations may be detected by standard karyotyping, wherein photomicrographs of the chromosomes in individual cells are analyzed. Another method of detection is to sort chromosomes from large numbers of cells, by flow cytometry (Gray, 1990) and to compare the results with a standard pattern.

For other purposes, it is also desirable to isolate groups of identical chromosomes. For example, in humans, aneuploidy of chromosome 21 is responsible for Down syndrome. To study the properties of this clinically important chromosome, it is helpful to separate large numbers of chromosome 21 from other chromosomes, or to isolate individual chromosome 21 in a background of chromosomes from another species. The former may also be achieved by flow cytometry, and the latter by, for example, somatic cell hybridization techniques. Although somewhat useful, current techniques for chromosome isolation and sorting each have serious limitations in terms of time and cost, unpredictability, inaccuracies due to contamination, and destruction or alteration of the chromosomes during processing.

The ability to isolate and sort specific chromosomes is of use in the study of both normal and malignant cell processes, and is an essential first step in the creation of chromosome-specific libraries for cloning. For instance, flow sorting of specific chromosomes has been used to detect deletions in apparently balanced translocation chromosomes (Cooke et al., 1989). Because the deleted translocation is not the quantitative sum of its component parts, the missing part may be deduced. Flow cytometry has also been used to investigate genetic changes associated with the malignant state, as exemplified in a case of familial renal carcinoma, where two oncogenes have been translocated to the derivative chromosomes of a cancer-related translocation (Harris et al., 1986), a change that is detectable quantitatively.

Present methods for separation of small biological materials, e.g., chromosomes, which are in the range of 0.2 to 10 microns or even smaller entities such as B-chromosomes, minichromosomes and double-minute chromosomes, are inadequate or unavailable. Flow cytometry is not sensitive enough to guarantee separation of small individual components which often sort with the debris when discrimination is dependent on size. Somatic cell methods (hybridization, microcell fusion) can isolate chromosomes but the methods are laborious and unpredictable. Thus, the development of a separation method that is not solely dependent on size differences, but is related to other inherent properties of the materials to be separated, would be particularly advantageous.

To collect organelles, cells or protoplasts are lysed by physical or isotonic disruption into an isolation buffer which is appropriate for specific organelles and cell types. An example of an appropriate buffer for chloroplast isolation is described by Gruissem et al. (1983). Crude organellar preparations can be made by differential centrifugation (see Cashmore et al., 1984). The crude organellar pellet is then layered over a cushion containing an appropriate percol concentration adjusted for the organelle of interest, in a 15 ml Falcon tube cap. The cap contains a glass coverslip that has been silanated and prefixed with DTSSP, so that following centrifugation the organelles are immobilized to the surface of the glass.

This invention has particular advantages for small biological materials. For example, chromosomes are of approximate size 0.5–10 µm; mitochondria 5–20 µm; chloroplasts 5–100 µm. As is evident from the subsequent discussion on magnetic particle sizes, an aspect of this invention is the use of small magnetic particles as labels, of the order of 1 nm-10 µm, preferably 5nm-2.0 µm, for labelling these small biological materials. The choice of these small particles improves resolution.

B. Solid Support

The biological material is affixed, immobilized or anchored to a solid support. Any solid support which does not adversely affect the integrity of the biological material, which is capable of linking to a binding composition, and which can be manipulated to achieve the eventual separation of the biological material, is useful for purposes of this invention. In preferred embodiments, it is contemplated that the solid support is glass, either in the form of coverslips or controlled pore glass beads, or polymer beads. These supports can be scaled up by use of large sheets of similar materials. In preferred embodiments, it is contemplated that the solid support is a stable or a dissoluable (reversible) polymer. Exemplary polymers include alginate, polyethylene-co-vinyl acetate, (EVAC) and poiyanhydride co-polymer of stearic acid dimer and sebacic acid, (PCSAD:SA), also polyglycolate, polylactate and combinations thereof.

Recently, various methods have been developed for the immobilization of biological structures, and such methods have found numerous applications, for example, in molecular biology. Biologically active structures such as enzymes have been immobilized on matrices such as silica for use in studies of biochemical catalysis (Wu & Walters, 1988). Oligonucleotides are currently synthesized on controlled pore glass supports (Damha et al., 1990). Various purification methods and DNA capture methods rely on the immobilization of molecules of interest on a solid support (Bebee & Gebeyehu, 1990). Biosensors and monitoring systems have also been designed using immobilized biomolecules (Lehman, 1990).

Anchoring methods can utilize a variety of chemical crosslinking agents (Staros, 1982), both cleavable and non-cleavable. Thus, immobilization can be reversible or not, as required. However, these methods have not been applied to isolating and sorting of small biological materials. The combination of methods in the present invention addresses the separation and isolation of small biological materials.

Figure 2:
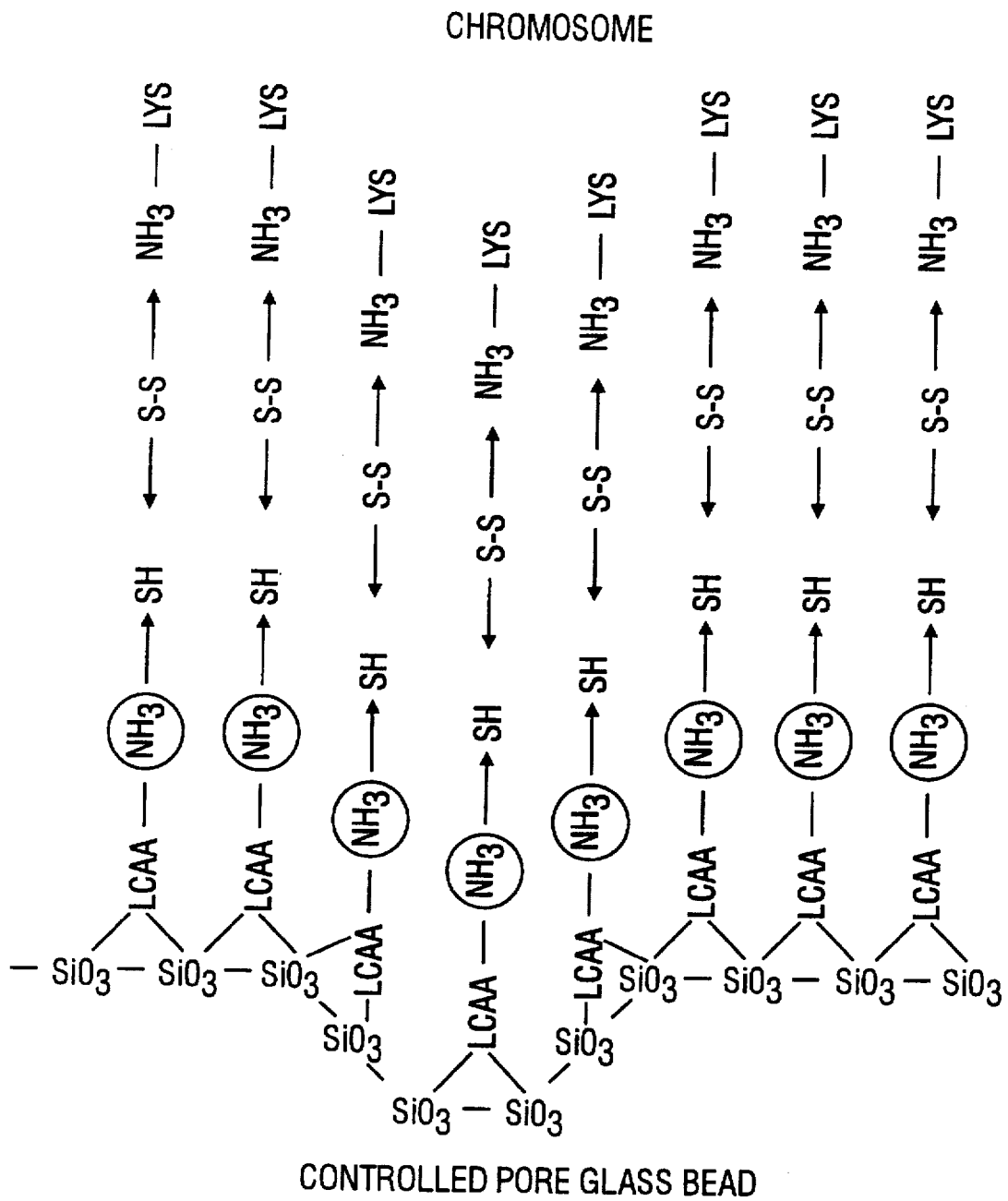
FIG. 2 is a representation of a reversible linkage between a chromosome and a support in the form of a controlled pore glass bead (CPG).

Supports are prepared by treating them with an agent which can anchor chromosomes, segments of chromosomes or small organelles. Exemplary cross-linking agents are listed in Table 2. These materials are attached to derivatized glass surfaces with various reversible cross linkers, carried through an in-situ hybridization reaction, and later released from the support with a strong reducing reagent. (FIGS. 1 and 2).

TABLE 2

| Cross-linking Agents |
|---|
| N-Succinimidyl 3-(2-pyridyldithio)propionate (SPDP) |
| Sulfosuccinimidyl 6-[3-(2-pyridyldithio) propionamido] hexanoate (Sulfo-LC-SPDP) |
| Succinimidyl 6-[3-(2-pyridyldithio) propionamido] hexanoate (LC-SPDP) |
| Sulfosuccinimidyl 2-(7-azido-4-methylcoumarin-3-acetamide) ethyl-1,3'-dithiopropionate (SAED) |
| Sulfosuccinimidyl 6-[alpha-methyl-alpha-(2-pyridyldithio) toluamido]hexanoate (Sulfo-LC-SMPT) |
| 1,4-Di-[3'-(2'-pyridyldithio)propionamido]butane (DPDPS) |
| Dithiobis(succinimidylpropionate) (DSP) |

TABLE 2-continued

Cross-linking Agents 3,3'-Dithiobis(sulfosuccinimidylpropionate) (DTSSP)
Disuccinimidyl tartarate (DST)
Disulfosuccinimidyl tartarate (Sulfo-DST)
Bis[2-(succinimidooxycarbonloxy)ethyl]sulfone (BSOCOES)
Bis[2-(sulfosuccinimidooxycarbonyloxy)ethyl]sulfone (Sulfo-BSOCOES)
Ethylene glycolbis(succinimidylsuccinate) (EGS)
N-[4-(p-azidosalicylamido)butyl]-3'(2'-pyridyldithio)propionamido (APDP)
Dimethyl 3,3'-dithiobispropionimidate-2 HCI (DTBP)
Bis-[β-(4-azidosalicylamido)ethyl] disulfide (BASED)
N-Succinimidyl(4-azidophenyl)1.3'-dithiopropionate (SADP)
Sulfosuccinimidyl(4-azidophenyldithio)propionate (Sulfo-SADP)

FIG. 1 is a representation of a reversible linkage between a chromosome and a support in the form of a piece of glass, for example, a coverslip. LYS refers to the free amines ($NH_2$) from the lysine residues in the chromosomes. The S-S link is provided in this representation by DTSSP which recognizes free amines ($NH_2$) at both ends. The silane provides free amines to the glass solid support, shown as a linkage of $SiO_3$.

In one embodiment, a support to which the biological materials is anchored is treated with an anchoring agent, a cleavable cross-linking agent, and a releasing agent. Although treatment of glass surfaces with a homobifunctional cross-linker is an embodiment of a method of anchoring, other schemes such as the use of heterobifunctional cross-linkers for reversibly anchoring chromosomes to a solid support are preferred. These include heterobifunctional agents such as SPDP and the like. In another embodiment, a reversible anchoring agent is a stable polymer or a dissolvable polymer. Furthermore, the anchoring agent can be a stable or a dissolvable polymer. Exemplary polymers include alginate polymer, poly(ethylene-co-vinyl acetate), (EVAC), polyanhydride copolymer of stearic acid dimer and sebacic acid, (P(SAD:SA)), and polyglycolate, polylactate and combinations thereof. Preparation of alginate polymer is described in example 3 of the present application. Preparation of EVAc and P(SAD:SA) is described in Sherwood et al., 1992. EVAc is an example of a stable polymer and P(SAD:SA) is an example of a dissolvable polymer.

A binding composition which can bind to the cellular component is embedded in the polymer. As used herein, the term "embedded" describes the dispersion of the binding composition within or on the polymer. The interaction between the binding composition and the polymer includes any molecular interaction. These molecular interactions include ionic, covalent, hydrophilic, hydropathic, Van der Waals, and other molecular forces.

It will be recognized that the binding composition can be an antibody. The antibody can be directed towards the immunological recognition of the cellular component. Thus, if the cellular component of interest is a vesicle, chloroplast, plastid, nucleus, mitochondria, endoplasmic reticulum, golgi apparatus or any other cellular component, an antibody which is immunoreactive with the cellular component of interest can be embedded in the polymer.

The cellular component of interest is anchored to the polymer through a binding interaction between the cellular component and the binding composition. If the cellular component is a nucleic acid molecule, the binding composition can be a nucleic acid molecule that is complementary to the nucleic acid molecule of interest. Alternatively, the binding composition can be an antibody that is immunoreactive with the nucleic acid molecule of interest. For example, if the cellular component of interest is a chromosome, an anti-histone antibody or an anti-NOR (nucleolus organizing region) antibody can be embedded in the polymer. Alternatively, reversible biotinylated antihistone antibodies, available commercially, may be immunoreacted with the chromosomes. Streptavidin is embedded in the polymer and the chromosome is anchored to the polymer through the streptavidin-biotin interaction.

The anchored cellular component can be released through several alternative mechanisms. If the binding composition directly recognizes the cellular component, the addition of a releasing compound which binds to the binding composition can be added. For example, if the binding composition is an antihistone antibody, the addition of excess $F_{ab}$ fragments of the antihistone antibody will release the anchored chromosome by immunoreacting with the histones. Alternatively, if the binding composition is a reversible biotinylated antihistone antibody, the anchored chromosome can be released by the addition of a thiol cleaving agent. If the cellular component of interest is an organelle, the addition of excess $F_{ab}$ fragments of the anti-organelle antibody will release the anchored organelle by immunoreacting with the organelle. If the polymer is a dissolvable polymer, for example P(SAD:SA), the anchored cellular component can be released by slow dissolution of the polymer.

The use of controlled pore glass (CPG) beads both with and without attached long chain alkylamine linker arms is preferred as a support. The foam-like structure and relatively small amount of available outer surface of the CPG allows the attachment of chromosomes to their surfaces through fewer crosslinks, and hence improves yield after reversal of the linkages.

It is also possible to reversibly crosslink isolated biological material to polymer beads that have been derivatized with oligopeptides terminating in attackable reactive amino groups. This approach combines solid phase peptide synthesis protocols with the techniques described above, and is attractive because oligopeptides can be custom made with, for example, strong internal rigidity, and to a variety of lengths. Thus, characteristics of such linker molecules for maximal capture of biological material and release after crosslink reversal can be optimized. In addition, the use of microbead supports that can be manipulated in suspension instead of a flat glass surface, may improve efficiency of reactivity.

The efficiency of any reversible anchoring procedure depends on having a controllable reaction with the crosslinking agent. Homobifunctional crosslinkers, for example, DTTSP, are successful for purposes of this invention although prior treatment of supports such as glass has the potential to render a proportion of the linker unavailable for reaction with the biological material due to reaction of both ends with the support. This problem is overcome by the use of heterobifunctional thiol cleavable crosslinkers such as N-succinimidyl 3-(2-pyridyldithio)propionate (SPDP). Use of compounds such as these permit a more controllable, and more effectively reversible anchoring procedure because supports are modified so that they will react with only one end of the crosslinker, leaving the other end free to react with the biological material. An example of a releasing agent is dithiothreitol (DTT), which cleaves disulfide bonds. Other exemplary reducing agents that may be used in the practice of the invention are tris(2-carboxyethyl)phosphene hydrochloride (TCEP), β-mercaptoethanol (BME), β-mercaptoethylamine HCL, Ellman's reagent (5-5'-dithiobis-(2)-nitro benzoic acid), Reduce-IMM™ (Pierce) or any other reducing agent that will displace or break disulfide bonds.

An anchoring procedure allows efficient labelling of biological materials for separation without the loss and aggregation associated with carrying out labelling reactions in suspension. Furthermore, debris and contaminants can be easily washed away from an immobilized preparation. Reversal of the immobilization step then allows the labelled material to be recovered for sorting.

To reversibly immobilize or anchor biological material, supports are preferably treated with reversible crosslinkers. In an illustrative embodiment, glass surfaces are derivatized with N-(2-aminoethyl)-3-aminopropyl trimethoxysilane, according to specification by Pierce Chemical Co. Coverslips were prefixed in freshly made 1 mM DTSSP (Pierce), 2×SSC for 1 h at room temperature. Silane provides functional amino groups that can be attacked by the thiol cleavable crosslinking agent dithiobissulfo succinimidyl propionate (DTTSP). (Staros, 1982) (FIG. 1). Chromosomes from cell lysates were pelleted through sucrose by standard methods (Rattner and Hamkalo, 1978) and attached to these prepared surfaces by reaction of the amino groups of chromosomal proteins with bound DTSSP. Although postfixation with glutaraldehyde was necessary to stabilize the chromosomes against degradation, in-situ hybridization reactions were conducted on these preparations using biotinylated probes (FIG. 6), and target sequences were detected by standard antibody sandwich amplification schemes (Narayanswami et al., 1989) followed by either colloidal gold (for electron microscopy) (FIG. 7), or magnetically responsive biotinylated ferric oxide particles (FIG. 8) for sorting in a magnetic field. The signal was amplified (FIG. 9).

FIG. 2 is a representation of a reversible linkage between a chromosome and a support in the form of a controlled pore glass bead (CPG). LYS refers to free amino groups ($NH_2$) provided by lysine residues in the chromosome. The S-S link is provided in this illustration by SPDP which recognizes the sulfhydryls (SH) on one end and the free amines on the other. This band is a cleavable disulfide linkage which may be released with a releasing agent (e.g., 50 mM DTT). The free amine ($NH_2$) is converted to sulfhydryl groups by Traut's reagent. LCAA refers to the long chain alkyl amine which provides free amines on the support phase. The solid support phase of the controlled pore glass bead CPG is shown as a linkage of $SiO_3$.

The reducing reagent does not remove the labelled probes from the reacted biological material. Reversible crosslinkers (DTTSP/SPDP) are used to anchor chromosomes to the glass supports. The anchored chromosomes are fixed to protect them against destruction by denaturing agents. A nonreversible crosslinker, such as glutaraldehyde, can be used as a post-fixative to increase stability of the biological material. It was determined for chromosomes that the number of cross links introduced by post-fixation is directly correlated to maintenance of chromosome integrity throughout this procedure. A titration series can be constructed to optimize time and concentration values for reversible crosslinker and nonreversible post-fixatives for different biological materials.

Figure 3:
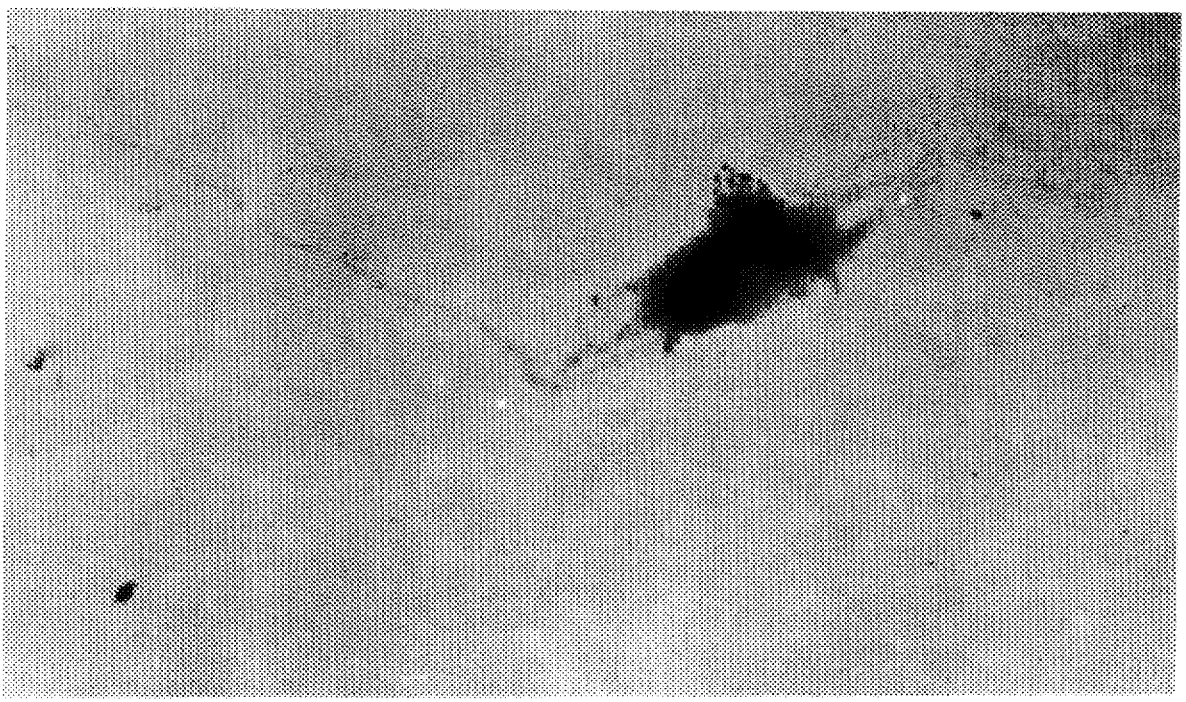
FIG. 3 shows a chromosome which has been isolated and released from a glass solid phase support after fixation with 0.1% glutaraldehyde, standard in-situ reaction, and reduction with 50 mm of DTT, a releasing agent.
Figure 4:
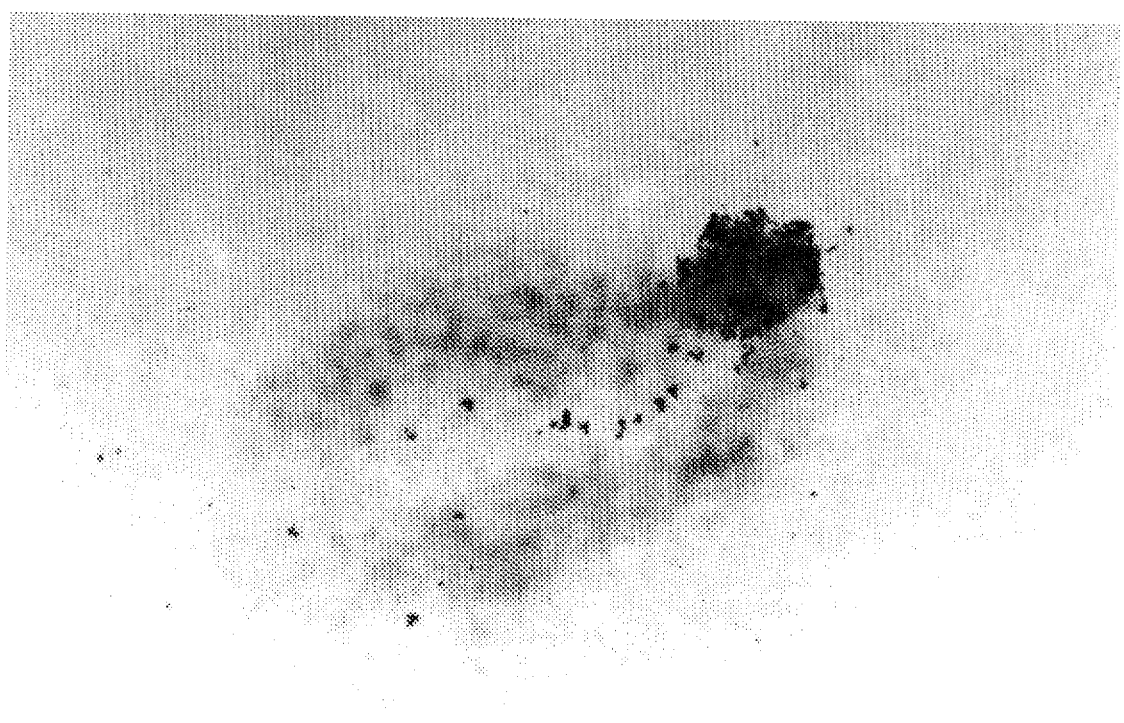
FIG. 4 is the same as FIG. 3 except that fixation was in 0.03% glutaraldehyde.
Figure 5:
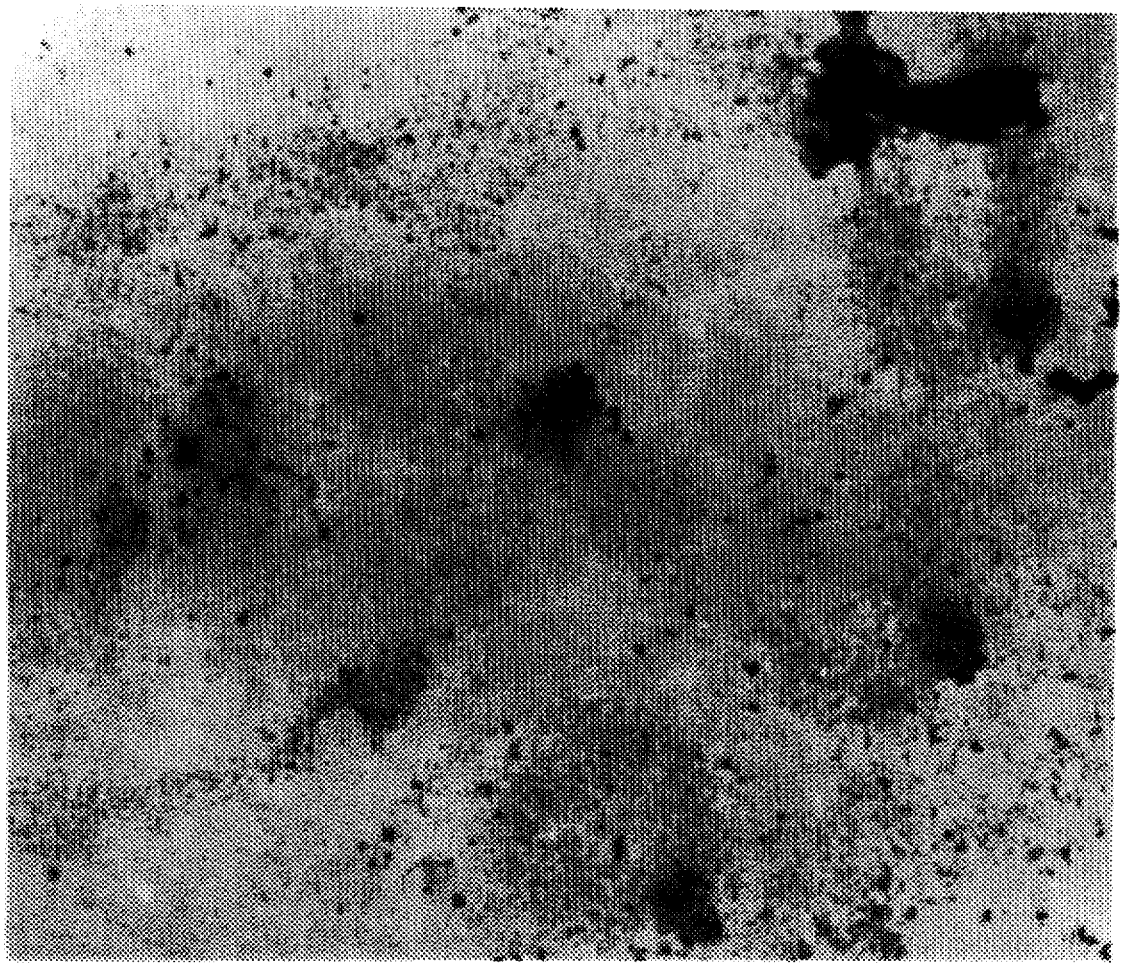
FIG. 5 is the same as FIG. 3 except fixation is in 0.01% glutaraldehyde.

FIGS. 3-5 show the morphologies of chromosomes isolated and released from a glass solid phase support, after post-fixation with 0.1%, 0.03%, and 0.01% glutaraldehyde, standard in-situ reaction, and reduction with 50 mm DTT, a releasing agent. Chromosomal morphology was optimal at 0.1% glutaraldehyde post-fixation.

The use of flat glass as a solid support phase for reversible attachment of chromosomes during in-situ hybridization reactions has some limitations for use in chromosome sorting and isolation. Controlled pore glass beads of pore size smaller than chromosomes are preferred so that less of the chromosomal surface area is in contact with the support, reducing the time and concentration of the releasing agent, e.g., DTT, necessary to remove it. The presence of pores may also improve reagent access to crosslinks.

Figure 6:
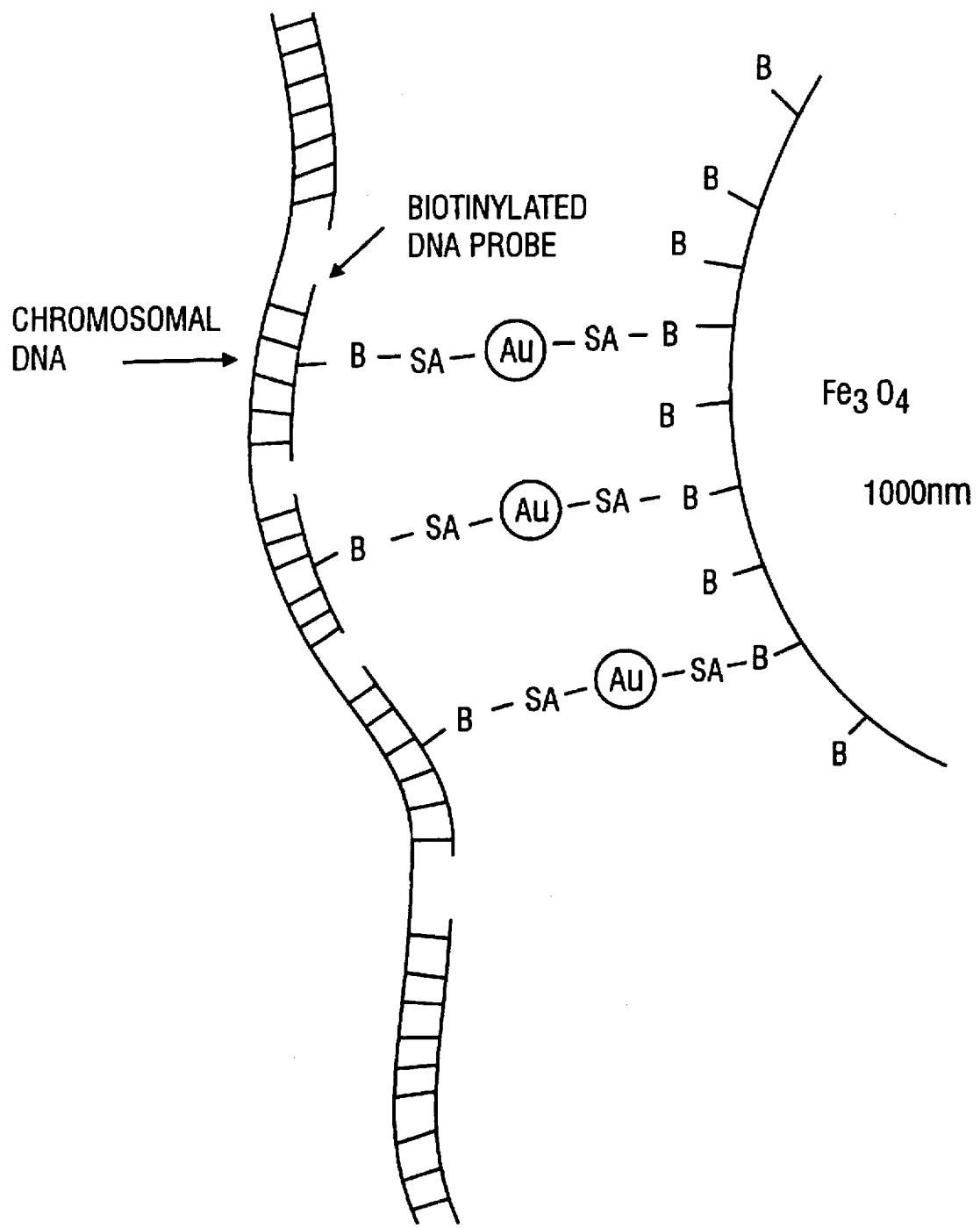
FIG. 6 is a diagrammatic representation of linkage between chromosomal DNA and ferric oxide (1000 nm) via a biotinylated DNA probe, streptavidin, and colloidal gold.

FIG. 6 is a diagrammatic representation of a linkage between chromosomal DNA 70 and ferric oxide 74 (1000 nm) via a biotinylated (B) DNA probe 72, streptavidin (SA) and colloidal gold (Au). The $K_m$ of these reactions ranges from $10^{-12}$ to $10^{-15}$.

Figure 7:
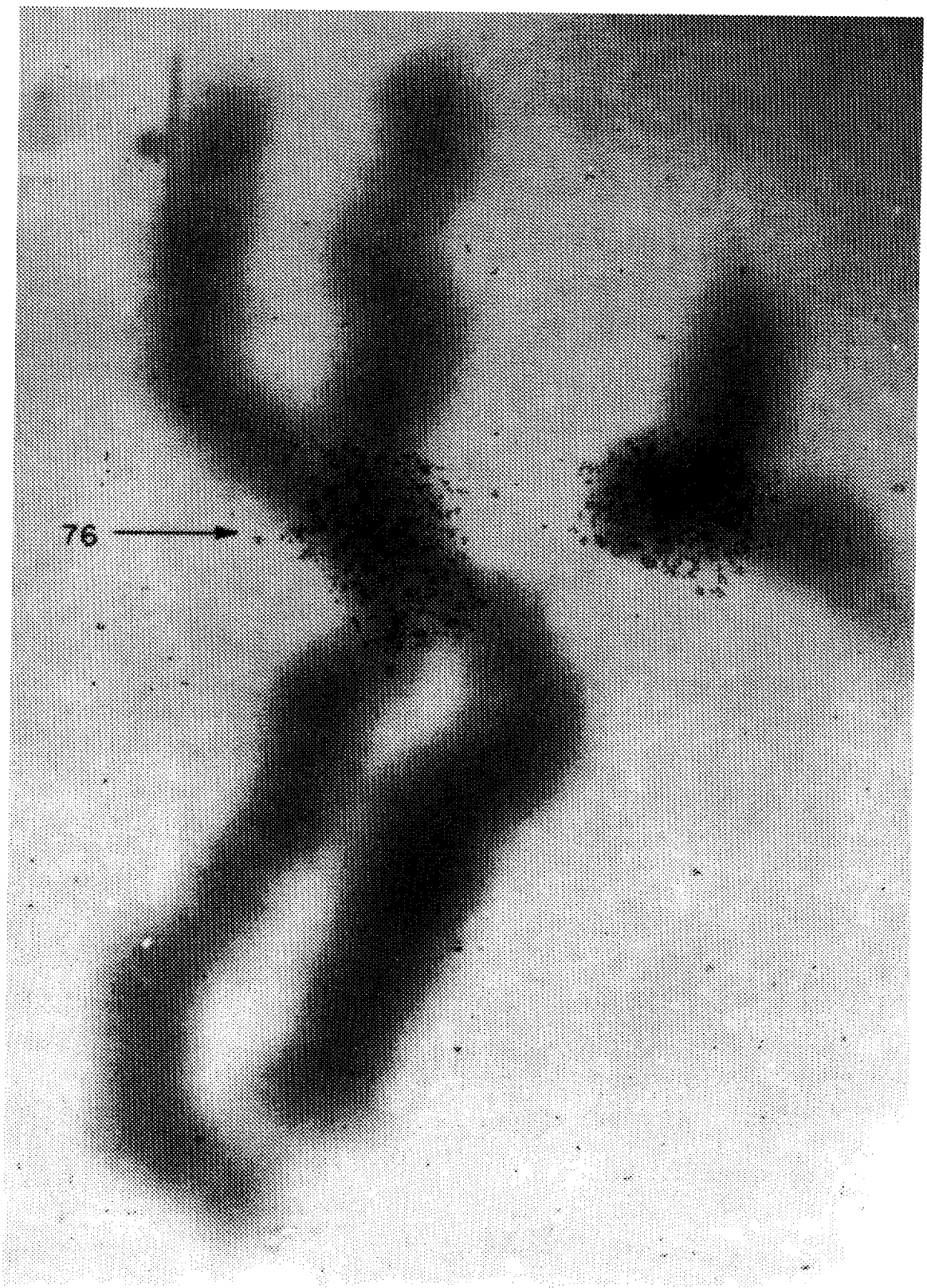
FIG. 7 shows a chromosome labelled with colloidal gold (see Reaction 1 in Table 1 of Example 1, described hereinafter).

FIG. 7 shows a chromosome labelled with colloidal gold (see Reaction 1 in Table 1 of Example 1, described below). The label 76 can be seen at the centromeric region (the centromere is the primary constriction of each chromosome). This position is consistent with the hybridization characteristics of the nucleic acid probe.

Figure 8:
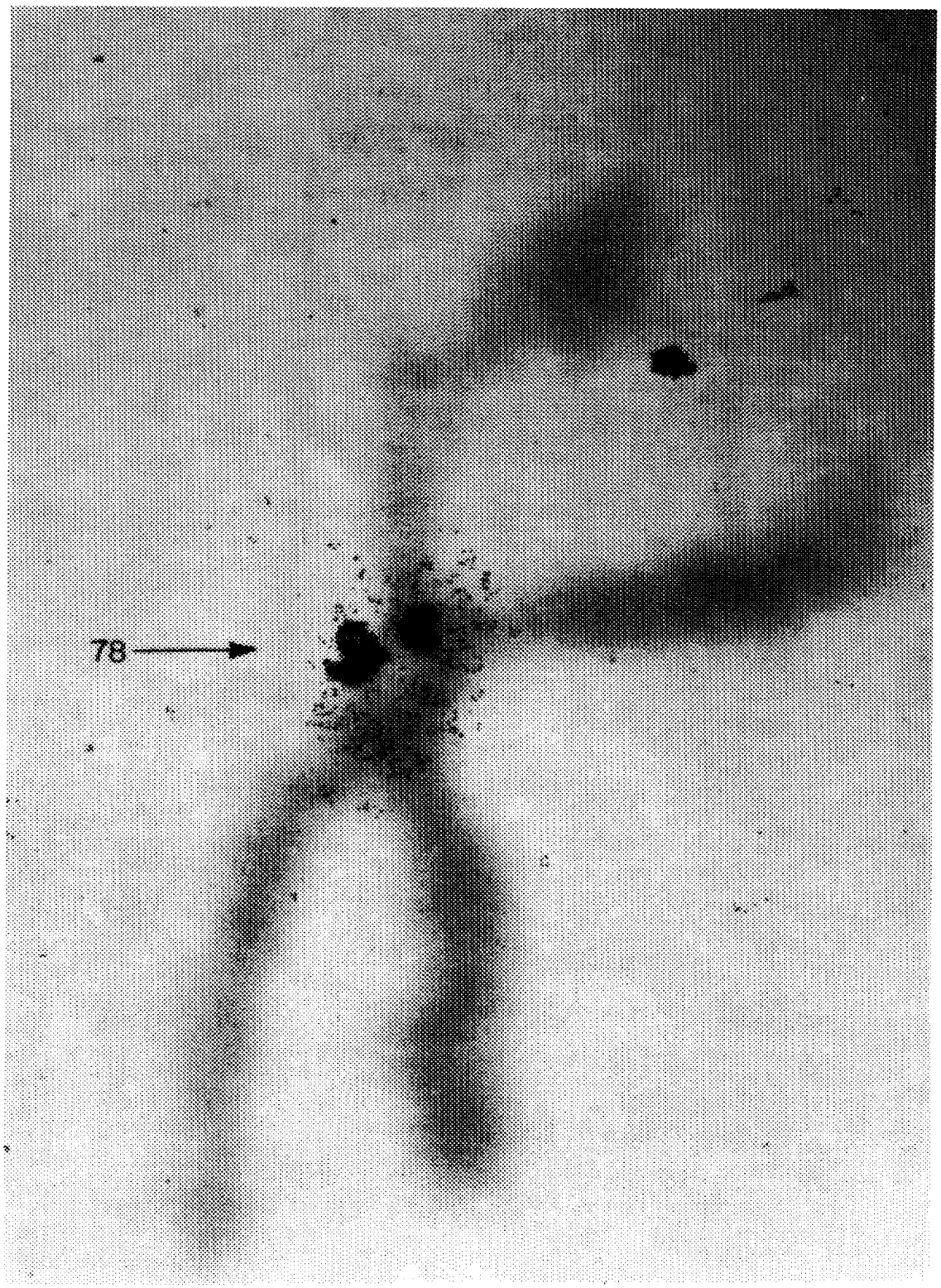
FIG. 8 shows a chromosome in which iron oxide particles are bound to the colloidal gold as illustrated in FIG. 7 (see Reaction 2 in Table 1).
Figure 9:
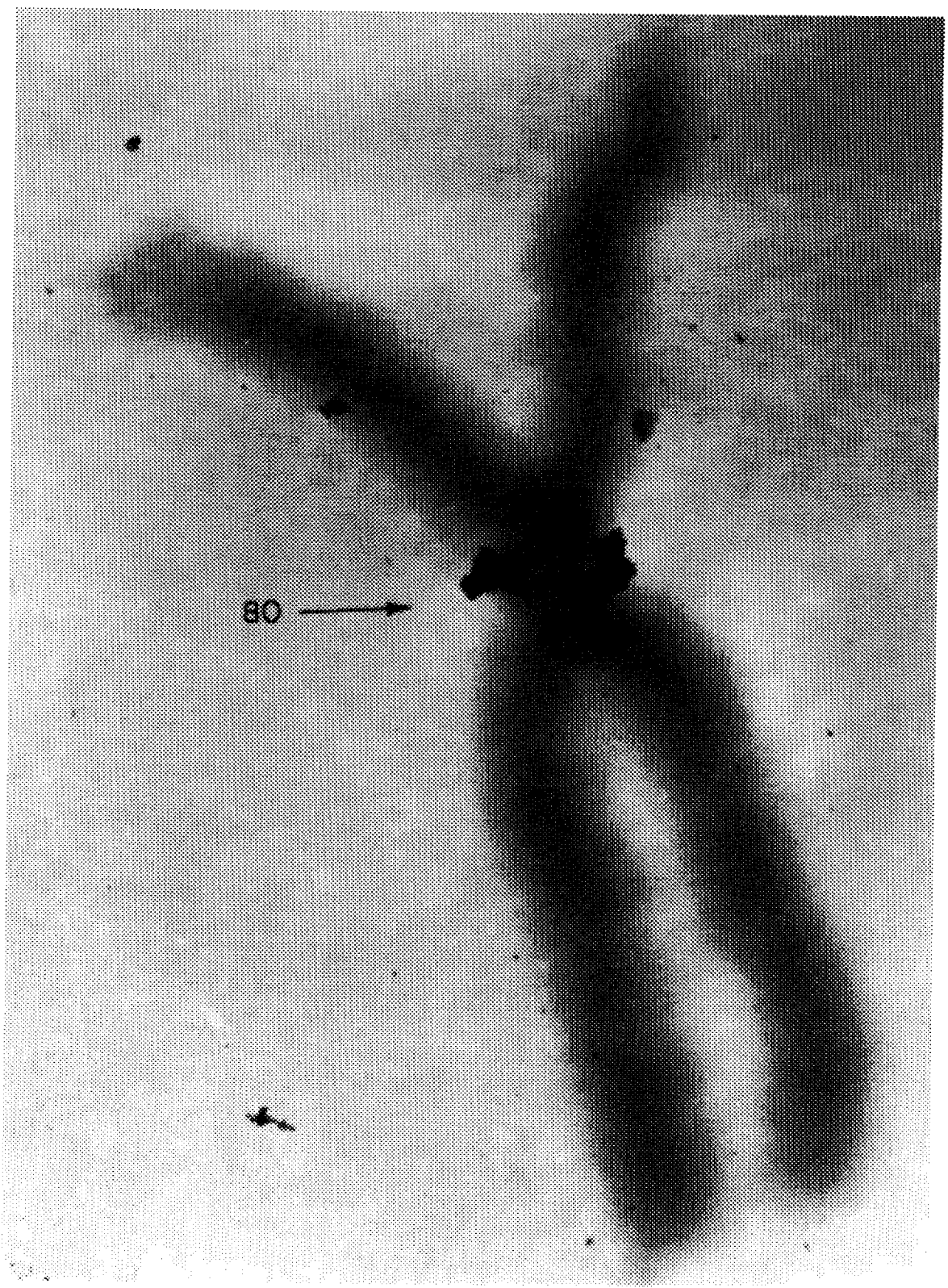
FIG. 9 shows a chromosome in which the signal has been amplified.
Figure 10A:
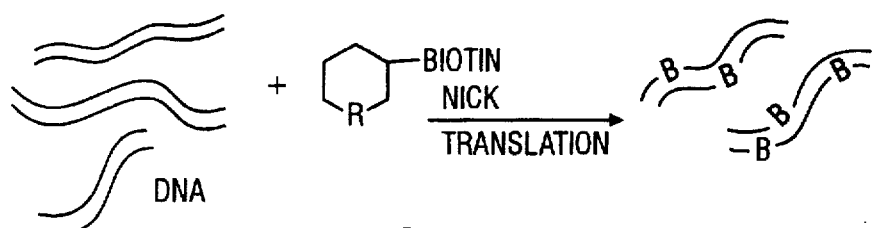
FIG. 10 is a schematic representation of in-situ hybridization of electron micrograph chromosome preparations.
Figure 10B:
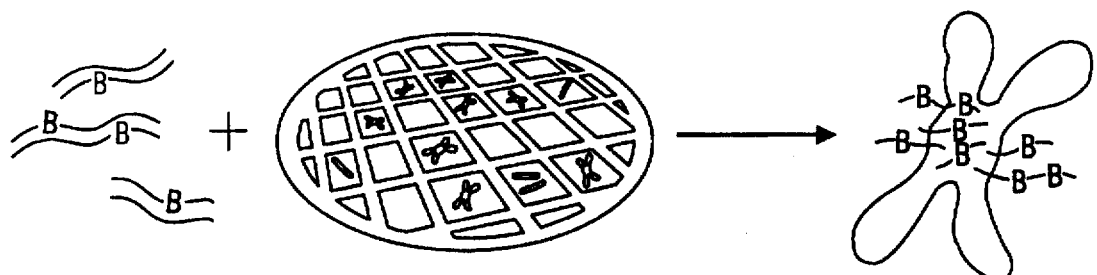
Figure 10C:
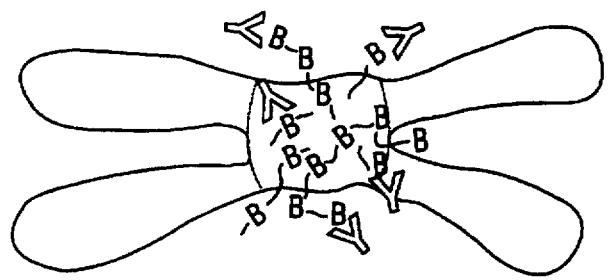
Figure 10D:
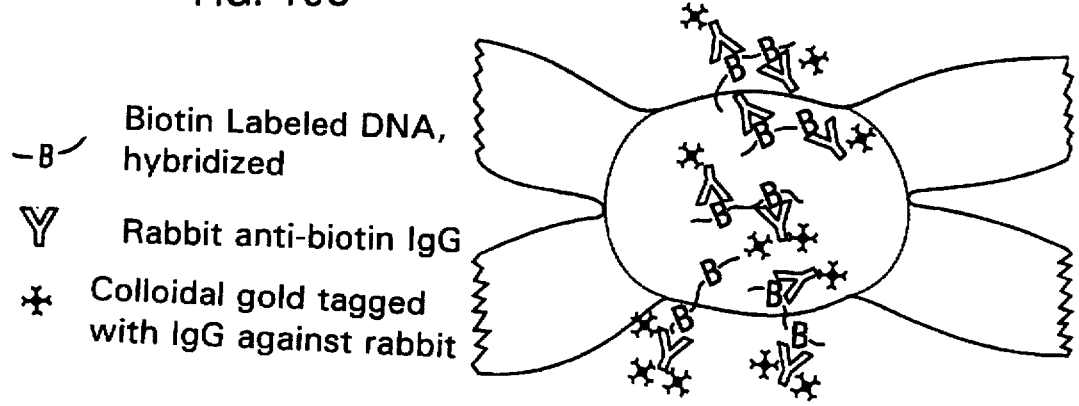
Figure 12:
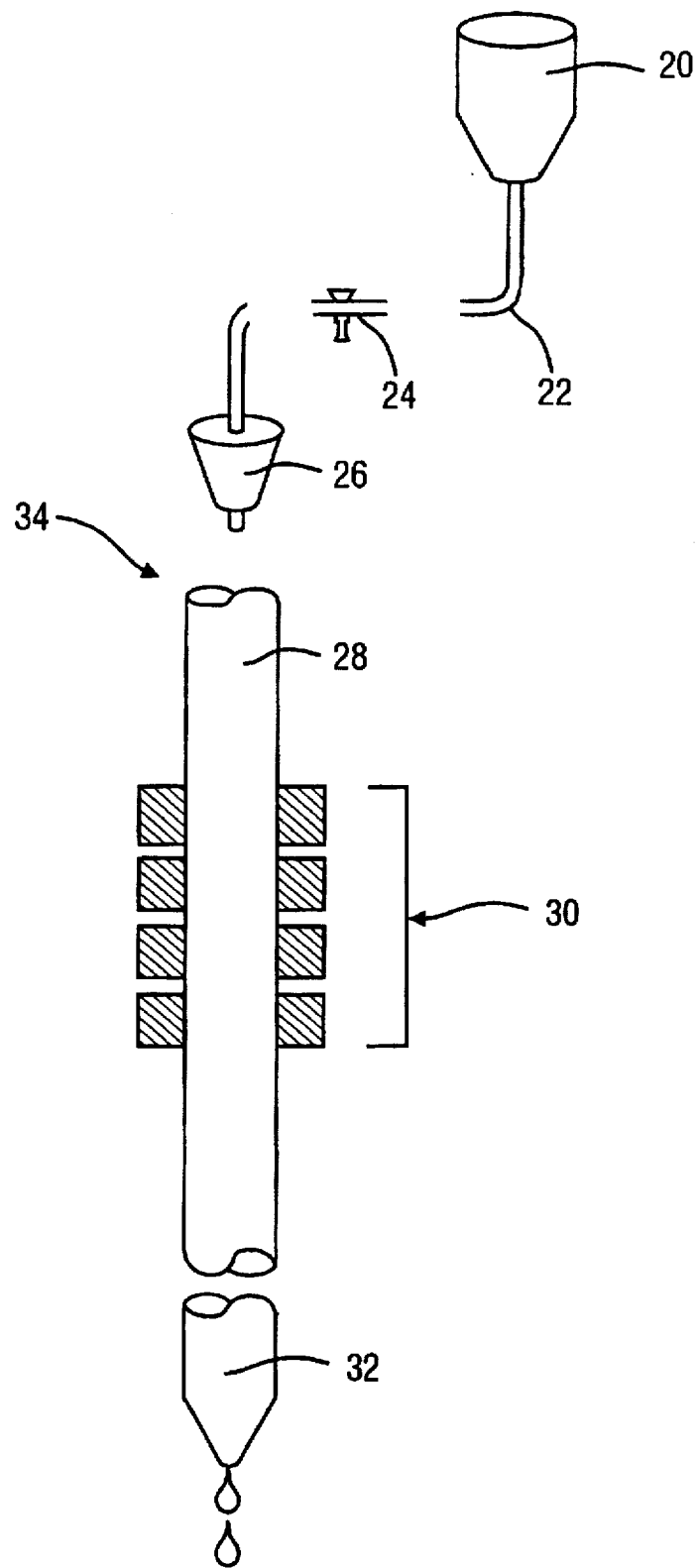
FIG. 12 is a schematic, broken and partially sectioned diagram of a magnetic affinity column used to collect magnetically labelled biological material.
Figure 13:
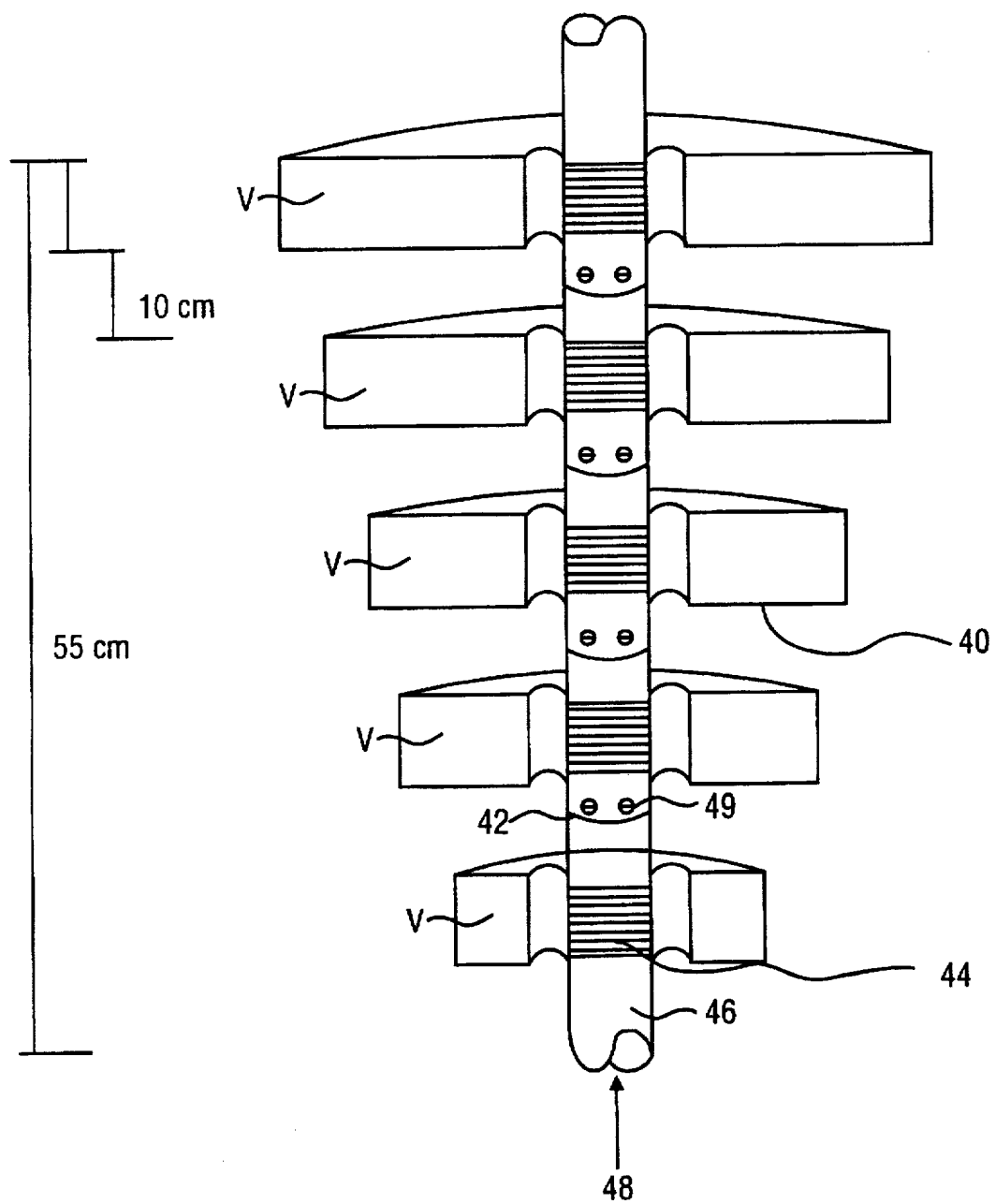
FIG. 13 is a cross-sectional diagram of an embodiment of an apparatus used to collect and separate chromosomes with different amounts of magnetic labels.
Figure 14:
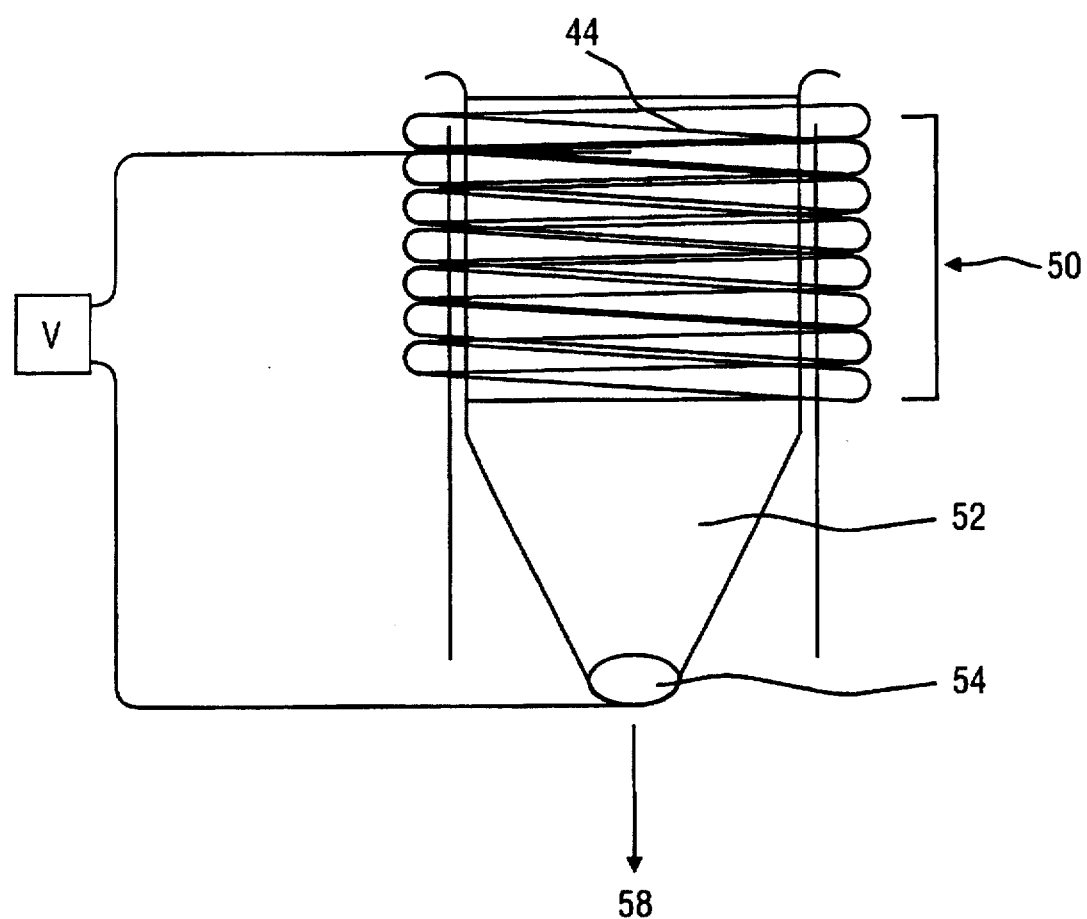
FIG. 14 is a magnafuge, which is a magnet "centrifuge" used to remove the pelleted biological material.

FIG. 8 shows a chromosome in which iron oxide particles are bound to the colloidal gold 78 as illustrated in FIG. 7 (see Reaction 2 in Table 1).

FIG. 9 shows a chromosome in which the signal has been amplified 80. A positive reaction is evidenced by a deposition of product at the centromeric region. This Reaction (see 4 in Table 1) addressed the question of steric hindrance.

In still further embodiments, the present invention concerns reversible anchoring to a solid support, this aspect per se has important uses. Reversible immobilization methods for cell organelles may have commercial applications if the biochemical activity of anchored organelles is preserved, i.e., sensor design, energy cells, prosthesis design for the replacement of defective organelles (for instance, some neuromuscular diseases are due to defective mitochondria). With appropriate solid supports available, scaling up is also possible. In the case of chromosomes, this system may be considered as a solid phase chromosome system, and as such is amenable to applications other than chromosome sorting. It may be used as a medium for directed chromosome modification, because in essence it allows chromosomes to be subjected to various defined manipulations and then recovered for further analysis. Entire modified chromosomes could, for instance, be used for cell transformation and the introduction of desirable traits, or as a functional assay for DNA sequences of interest in eukaryotes, a need which has not yet been filled in molecular biology and which is of considerable importance. In addition, modified chromosomes could be used for the construction of artificial chromosomes.

The ability to reduce contaminant levels by extensive rinsing of an immobilized preparation is an important advantage over current protocols for in-situ hybridization 'in suspension. Reversibility of the attachment is another important aspect. The anchoring reduces problems due to internal aggregation of the biological material and other undesirable interactions.

The present invention requires a minimum of specialized, expensive reagents or equipment for its execution, and thus constitutes an easily transferable technology as well as a cost effective means of isolating specific chromosomes as readily replaceable resources. The present invention can yield large amounts of chromosomes, DNA, cellular organelles, or other cellular components. Some of the potential applications of the nethodology are listed below.

C. Binding Compositions

The biological material that is reversibly anchored to a solid support is labelled with a binding composition that specifically labels the target biological material. As a result of labelling, the target biological material to be separated by a process of the present invention can be distinguished from biological material that is not the target of a separation process.

Typically target material is distinguished from non-target material by labelling the target material. A process of the present invention also contemplates labelling of the non-target biological material. Any binding composition that distinguishes between target and non-target biological material and which binding composition does not adversely affect the integrity of the target biological material is suitable for use in a process of this invention.

One preferred embodiment of the present invention is contemplated to be the marking and isolation of a nucleic acid target material by the use of a triple helix forming probe. In this method, a nucleic acid probe comprising a homopurine stretch of nucleotides and/or a homopyrimidine stretch of nucleotides may be used to form a triple helix, or a triplex with a complementary sequence in a nucleic acid target, such as a chromosome, for example. An application of this targeting method in a liquid solution rather than as an immobilized target is described in Ito et al., 1992, incorporated herein by reference.

In this embodiment, the nucleic acid probe would be labeled, for example. After contact of the target and probe, and separation of the extraneous materials, the target-probe complex may be removed from the solid support by the methods disclosed herein. After removal from the solid support, the labeled complex would be separated by magnetic affinity chromatography, for example, and the triplex would then be separated by treatment with mild alkaline, which separates the triplex bond, but does not affect the Watson-Crick base pairing.

In a preferred embodiment, a binding composition comprises a nucleic acid probe or an antibody. Where the binding composition is a nucleic acid probe, that probe is designed to hybridize to one or more nucleic acid sequences in the biological material. The specificity of a nucleic probe, as is well know, is a function inter alia of the nature and length of the probe as well as the hybridization conditions employed. Means for varying hybridization conditions to achieve high, low or medium stringency hybridization are well known in the art.

Another preferred binding composition comprises an antibody having immunospecificity for the biological material. An antibody used in a process of the present invention can be a polyclonal or a monoclonal antibody. Where a high degree of specificity is desired, a preferred antibody is a monoclonal antibody. Means for preparing antibodies and determining the immunospecificity of such antibodies are well known in the art. Detailed descriptions of the use of nucleic acid probe and antibody binding compositions are set forth below as well as in the Examples.

In one embodiment, where DNA is the target of the isolation procedure, a preferred binding composition is a nucleic acid probe. For example, a probe can be directed to a repetitive sequence of specific centromeric regions, to the entire chromosome, or to a single gene. The probe can also include triple helix forming sequences and PNA probes as described above. In an exemplary embodiment, a probe is a nick-translated plasmid, usually 500 bp-5 kb in length allowing specific chromosomes to be recovered. Such isolated chromosomes would have utility in the production of chromosome specific libraries, and the production of physiologically intact chromosomes.

In a second embodiment, a preferred binding composition is an antibody to elements contained within the biological material, e.g., histones (H1), so that intact chromosomes are recovered form a mixture of cell components. Another aspect of this second application is to isolate specific chromosomes on the basis of chromosomal proteins rather than DNA sequences. All these procedures are also applicable to interphase chromosomes, as well as to metaphase chromosomes, and segments of chromosomes. Nucleic acid probes or antibodies to specific proteins, are also useful labels for cell organelles such as mitochondria and chloroplasts, and for other small biological materials. Indeed, by employing a specific antibody one can isolate any biological component for which such an antibody is available or for which such an antibody can be generated.

In-situ hybridization of middle or high repeat DNA sequences using radioactive probes is available to those of skill in the art (Pardue & Gall, 1970). More recently, labelling with non-radioactive probes has been favored to detect the location of the hybridized probe. Hybridization occurs between complementary nucleic acid sequences if conditions are appropriate. As is well known to those skilled in the art, the hybridization conditions, i.e., the "stringency," may be controlled to permit hybridizing between segments of varying complementarity. Hybridization may occur between probes and segments of different sizes, for example, from high or middle repeat sequences, to single copy DNA. Hybridization may occur between probes and any cellular component containing nucleic acid. Chromosome-specific, repetitive sequence hybridization probes are readily available (Moyzis et al., 1987) and would be useful in the practice of the present invention.

Fluorescent rather than radioactive probes are also available, but there are problems in the detection of the fluorescent signal for single-copy DNA sequences because of the weak signal from a small target. Methods for amplification of the signal have been explored, e.g. by enhancing the strength of the signal itself, land will be known to those skilled in the art. Enhancing the signal detection, e.g. by digital image enhancement (Viegas-Pequignot et al., 1989) is another approach. An alternative application of the present invention would be to conduct in-situ hybridizations on whole chromosomes in suspension. Success in this venture would facilitate the Fluorescence Activated Cell Sorter (FACS) process for chromosome sorting.

Other methods of in situ hybridization that may be used in embodiments of the present invention include a scanning electron microscope in-situ hybridization method based on avidin-polymer spheres binding to biotin-coupled nucleic acid probes hybridized to polytene chromosomes as reported by Manning et al. (1975) (incorporated herein by reference). Dudin et al., (1988) carried out in-situ hybridization on suspensions of chromosomes prepared as for flow cytometry. Human genomic DNA biotinylated by nick translation was used to label human chromosomes by in-situ hybridization in suspension. In this study, streptavidin was covalently coupled to the surface of large (4 μm) magnetic beads and these were incubated with the hybridized chromosomes. The human chromosomes from Chinese hamster X human hybrid cell lines were reportedly bound to the magnetic beads through the biotin-streptavidin complex and separated from non-labelled Chinese hamster chromosomes by a simple permanent magnet. Hybridization was visualized by additional binding of avidin-FITC (fluorescein) to the unoccupied biotinylated human DNA bound to the human chromosomes.

These authors noted that for high purity sorting of chromosomes, interphase nuclei and heterogeneous aggregates, in this case hamster mixed with human chromosomes, must be significantly reduced or eliminated. It was suggested that 1 g sedimentation preferably prior to magnetic separation was a means of solving these problems. A further problem encountered by the investigators was severe clumping when large numbers of chromosomes/ magnetic beads were used. Overall, this approach has not been very successful due to problems with adventitiously adsorbed contaminants, and chromosome aggregation and loss in the centrifugation steps required for changing solutions during the procedure. Furthermore, buffer components such as hexylene glycol used in preparing chromosome suspensions cause excessive condensation of the chromosome and consequently a loss of accessibility of sequences within the structure of the condensed chromosome. This reduction in sensitivity is obviously detrimental to sequence detection. In addition, the large magnetic particles used, which are about the size of some chromosomes in metaphase (~3–4μ), reduced the yield because there is a low efficiency of labelling, probably due to limited target accessibility. Finally, lack of reproducibility means that suspension in-situ hybridization cannot be a solution to the problems of flow sorting of chromosomes.

More than one probe may be applied to a chromosome. If all the probes hybridize to the same chromosome, this may enhance sorting by providing a stronger signal. If the probes are to different chromosomes, they must be distinguishable in some way so the chromosomes may be separated by the magnetic field.

To sort more than one chromosome, chromosomes are labelled with differently substituted DNA probes. Each of these is labelled with magnetic particles of different sizes and/or amounts. After detachment, the labelled preparations are exposed to a weak magnet to isolate materials labelled with a large amount of particles, followed by exposure to a strong one, to isolate chromosomes labelled with the smaller particles. A gradient magnetic field can be used for simultaneous separation of differently labelled chromosomes. FACS may be used if chromosomes are labelled with a fluorochrome before cleavage of the cross-linkage. Thus, currently available multiple fluorescent detection methods may be exploited to sort biological material having different labels.

Antibodies can be effectively used for isolation and purification of physiologically intact organelles. For example, cell organelles can be isolated by preparing a cell lysate and reacting them to the appropriate cognate antibody immobilized on magnetic particles (i.e., to a chloroplast membrane protein), allowing recovery of the organelle in a magnetic field. The present inventors have developed a system for immunolabelled various forms of higher plant plastids with an antibody raised against pea chloroplast outer envelope proteins which had been covalently coupled to magnetic particle preparations and were isolated from whole cell lysates in a magnetic field. This antisera is immunoreactive with a variety of plastid forms from both monocotyledonous and dicotyledonous plants. By covalent coupling this antibody to magnetic nanoparticles, rapid and gentle isolation of physiologically intact organelles on a steel wool matrix suspended in a 0.6 Tesla high gradient magnetic field can be obtained. Using this immunoabsorption procedure, pure chromoplasts, amyloplasts, and chloroplasts from whole cell lysates of several plant species can be isolated. The integrity of these plastids has been examined by in organellar protein synthesis, $^{14}$C-ADP-glucose uptake, flow cytometry, in vitro synthesized precursor import and FITC-cationized ferritin staining of the plastid envelope. The ability to isolate intact nongreen plastids provides a superior physiological system for the study of many plant processes. Magnetic immunoabsorption of subcellular structures from whole cell lysates is a new method that is useful in the in vitro analysis of many different cellular compartments from a wide range of organisms.

Antibodies which are covalently coupled to magnetic nanoparticles and specific to extrinsic epitopes on the cytosolic side of chloroplasts can be used for immuno-isolation of various plastid subtypes from whole cell lysates. The results indicate positive enrichment of plastids by a specific biochemical criteria. This approach is extendable to other subcellular structures or organellar components. Preliminary results have shown that it is possible to enrich for plastid membrane fractions associated with the adhered magnetic particles by lysing the organelle on the column matrix and recovering the retained fraction after stringent washing. The chicken polyclonal antibody used in these experiments, reacts with at least five different proteins on the outer envelope and it is not determined which of these is capable of interacting with magnetic particle preparations. Studies on magnetic cell separation (Liberti and Feeley, 1991) indicate that specific monoclonal antibodies to cell surface antigens increase yields and decrease nonspecific reactivity, and it is contemplated that the depletion ratios and recoveries would improve with a monoclonal antibody preparation.

D. Indicators

A binding composition generally comprises an indicator. Any indicator that attaches to the labelled biological material and can be used to separate and isolate the biological material is suitable. Exemplary such indicators are fluorescent indicators, magnetic indicators and colloidal gold. Particular indicators and means for attaching those indicators to target materials are well known in the art. In an illustrative embodiment, the indicator is a fluorescent indicator such as biotin-avidin with fluorescein. In this case, intensified fluorescent digital-imaging microscopy is employed to detect the fluorescent label (Viegas-Pequignot et al., 1989).

An indicator is used to further label or tag the biological material-binding composition complex. The indicator is used a means of separating target from non-target biological materials. In a preferred embodiment, an indicator attaches to the binding composition that is used to label the biological material. By way of example, where the binding composition comprises a nucleic acid probe, the indicator attaches to that probe.

A binding composition can be attached to an indicator either before or after labelling of the biological material with the binding composition. Thus, in one embodiment, the binding composition comprises an indicator. Alternatively, an indicator can be attached to a binding composition that is already bound to biological material. A preferred indicator is a magnetized particle, a luminescent indicator or colloidal gold.

Large paramagnetic particles are currently being used in conjunction with DNA diagnostics and cell separations (Kvalhelm et al., 1987). Magnetic affinity chromatography has also recently become a viable alternative method of purifying biological structures (Menz et al., 1986). Magnetic solid supports with specific affinity couples are used for separating cells, cell organelles, and microorganisms (Dudin et all, 1988). One member of the affinity couple is usually an antibody covalently bound or physically absorbed to magnetic microspheres. Some of those used are polystyrene beads containing ferric oxide ($Fe_3O_4$) particles (Lea et al., 1985; Howell et al., 1988).

Magnetic beads were originally developed for immunoassays, but have also been used to separate DNA and RNA (Uhlen, 1989). Some of the original magnetic particles, made by the polymerization of acrylamide and agarose with paramagnetic materials, were heterogeneous in size and magnetic content. Hydrophilic beads have now been developed that are more homogenous in size, density and amount of magnetized material. Such beads sediment homogeneously in magnetic fields. The chemical structure of the particle surface may be varied, providing a flexible system for the attachment of biomolecules.

A magnetic cell sorting system for separation of large numbers of cells according to specific cell surface markers was reported by Miltenyi et al. (1990). Cells were labelled sequentially with biotinylated antibodies, fluorochrome-conjugated avidin, and superparamagnetic biotinylated microparticles. These cells were then separated on high gradient magnetic (HGM) columns. Retained cells were then eluted from the column. This method was said to be compatible with analysis of separated cells by fluorescent microscopy or flow cytometry (FACS). Miltenyi et al. (1990) have implemented a suggestion by Molday and Molday to combine small superparamagnetic microparticles and high gradient magnetic (HGM) fields to separate cells; they call this MACS.

Magnetic cell separations have been achieved for several years, however, investigations using magnetic particles for immunoassays, isolation of RNA, DNA, viruses and subcellular compartments have been initiated only recently because magnetic particles with the appropriate properties necessary for various applications have been developed only in the last few years (for review, see Haukanes and Kvam, 1993). The use of monodispersed superparamagnetic microparticle preparations (sized in the micron range) coupled to monoclonal antibodies specific to cell surface proteins was pioneered by Treleaven et al. (1984) for affinity separation of neuroblastoma cells from bone marrow. These types of particles have since proven useful for other cell separations by positive enrichment, including incomplete removal of lymphocyte subsets for quantification (Brinchmann et al., 1988), and isolation of lymphoid cells from peripheral blood (Vartdal et al., 1986). Magnetic microparticles have been successfully used for recovery and genetic analysis of specific nucleic acids (Albretsen, 1990), and isolation of DNA binding proteins (Grabrielsen et al., 1990). The present inventors have determined that these particles are inadequate for plastid isolation from whole cell lysates owing to the nonspecific reactivity of the particle surface coatings or the relative size of the particles. However, plastids can be immobilized on these particles to facilitate handling when used in biochemical assays which require several incubation or wash steps. Immobilization of prefractionated stacked golgi to magnetic microparticles coupled to Sec 7p antibodies has proven useful for cell-free analysis of membrane traffic in transport vesicles (Franzusoff et al., 1992).

Organelle separation from whole cell lysate is possible with antibodies coupled to magnetic nanoparticles because of the properties of the particles and the flow separation method used for recovery. Their small size provides a fine colloidal suspension that has greater than a ten fold increased surface area relative to micron-sized particles and allows reactions with the antibodies to occur as if free in solution, such that nonspecific reactivity is minimized. The aspect of using flow past a magnetic affinity minimizes recovery of nonspecifically and weakly labelled structures indicating that there may be a magnetic threshold necessary to retain a labelled structure in a magnetic gradient against the force of flow. It may be for a similar reason that smaller contaminating organelles that may become weakly and nonspecifically labelled are not retained on the column. The viscosity of the isolation medium is another component to separation, however, in these experiments we were able to use unadjusted isolation buffers typically used for isolation of these organelles. The speed and gentleness of this fractionation approach should facilitate biochemical analyses of plastid metabolism as indicated by the physiological integrity demonstrated with the amyloplast preparations. The fragility of these organelles has traditionally encumbered studies on their physiology and starch metabolism in plants.

Magnetic microparticles tagged with antibodies to DNA binding proteins constitute useful reagents for isolating DNA sequences of interest. Such an approach possesses advantages over the immunoprecipitation methods currently employed to isolate such sequences. Furthermore, direct isolation from cellular DNA permits assessment of the in vivo behavior of DNA binding proteins. Among potential applications, immunomagnetic isolation could be used:

a) To identify the target DNA sequences of the products of mouse homeotic genes, such as Pax 1, for which antibodies are available. This would be a first step in the elucidation of the mode of action of these important regulators of differentiation;

b) To use antikinetochore antibodies immobilized on magnetic microparticles to isolate the DNA sequences to which these proteins bind. In *M. domesticus*, current opinion speculates that the minor satellite is the binding site (Wong et al., 1990). However, direct proof is lacking. The same experiment performed in *M. spretus*, whose centromere is differently organized (Narayanswami et al., 1992) might reveal whether kinetochore associated sequences are conserved among mice.

Transgenic mouse technology allows the use of a universal probe to isolate chromosomes. This approach can be used not only to isolate chromosomes for library construction, but it is contemplated that a transgene located in a region of interest could be used to isolate that region for further analysis of the integration site and adjacent DNA.

The physiological integrity of the organelles isolated by magnetic immunoabsorption is quite high by the different criteria. The FACS is capable of rapidly assessing the physical intactness of a large population of chloroplasts and shows that magnetically isolated chloroplasts are comparable or more intact than chloroplasts isolated from Percoll gradients. The degree of plastid intactness is directly related to the method of cell lysis. Magnetic antibodies do not differentiate intact versus ruptured organelles. Consequently, for immunoisolation of organelles from many plant cell types, lysates will necessarily be prepared from ruptured protoplasts, however, chopped endosperm cells provide an adequate lysate for intact amyloplast isolations. Magnetically isolated plastids are capable of in organellar protein synthesis. In vitro protein import, and $^{14}$C-ADP-glucose uptake and starch synthesis.

These types of assays can be easily accomplished on isolated organelles bound to the column matrix. The results with amyloplast preparations show an inverse relationship between starch synthesis and in organellar protein synthesis. No damaging effects of exposure to high gradient magnetic fields to organellar functioning have been observed by the present inventors.

This technique is applicable to any subcellular structure to which specific antibodies can be prepared against accessible extrinsic proteins. Magnetic antibodies can be used to select organelles from a whole cell lysate, as shown herein, or antibodies to other cell constituents could be used to deplete contaminating organelles from a given preparation.

Naked magnetic (ferric oxide) particles can be purchased from commercial suppliers, for example, 1) Ferro Fluids (Nashua, N. H.); 2) Advanced Magnetics (Collaborative Research, Cambridge, Mass.); and 3) Alfa Particles (Danvers, Mass.). These commercial preparations of naked ferric oxide range in particle and particle aggregate sizes. All these preparations are heterogeneous with regard to particle size and particle aggregate size. To use these preparations for this invention, they must be fractionated into more accurately by defined size classes. In a typical fractionation, a density sedimentation column (1–2 meter) and an electromagnet may be used to collect various size classes. Oxidation of the particles should be prevented, for example, by suspension in 100% ethanol. A slurry should be placed in the column and left for a period of time, such as 24 hours, until a gradient has formed. Aggregates will be towards the top and heavy particles towards the bottom. Specific magnets can be left against the column at certain size levels, and the other particles rinsed through. Because of the method of collection, these particles are by definition responsive to a magnetic field.

Following such a protocol, examination of the particles in the electron microscope after separating them by size revealed that there were two types of particles in the 100–500 nm and the 500–1000 nm size classes: solid single particles and aggregates of much smaller particles (about 2–20 nm). These aggregates appeared as grape-like clusters in the electron microscope. Resedimentation by density sedimentation further separated the aggregates from the solid particles.

One type of material that can be attached to magnetic particles to enhance their versatility is proteins. Two of the methods used to attach proteins to the ferric oxide particles are: 1) direct adsorption; 2) covalent attachment through a silane. Any protein has the potential to be covalently linked to magnetic particles. A preferred silane is N-(2-aminoethyl)-3-amino propyltrimethoxysilane (Pierce Chemical Co.). This silane provides functional amino groups which may be activated by glutaraldehyde and linked to specific proteins.

Collaborative Research sells magnetic particles with covalently attached antibodies. This company also sells biotinylated particles. Examination of these preparations in the transmission electron microscope (TEM) revealed two classes of particles reminiscent of those described above for the naked ferric oxide preparations, that is, single particles and aggregates (grape-like clusters).

For purposes of this invention, biological materials are preferably labelled with the grape-like ferric oxide aggregates. Because the ferric oxide particles are magnetically responsive, the labelled biologically material is also magnetically responsive.

The smaller magnetic particles such as those produced by Bangs Laboratories (50 nm) have advantages over larger ones. The binding reaction is faster, quantitative differences in labelling are feasible, beads do not interaggregate, and they are easy to sterilize. A disadvantage is that the small magnetic moment increases separation times in magnetic fields of conventional geometries. In any event, separation using the methods of this invention may be achieved in minutes. Lower magnetic fields provided by commercially available permanent magnets (100–1000 gauss) art adequate to remove materials such as chromosomes from a column. Rare earth magnets are preferred because they have intense magnetic fields (Advanced Magnetics). Preferably, magnetic particles used in a process of the present invention have a diameter of from 1 nm to 10 µm. More preferably, magnetic particles have a diameter of from 1 nm to 500 nm and, even more preferably from about 2 nm to about 50 nm.

Magnetic particles can be coated to reduce non-specific binding. Latex and other coatings are well known in the art to reduce non-specific binding. As mentioned above, biotin-avidin links are one example of a labelling system. The non-covalent biotin-streptavidin interaction is strong and stable ($K_m=10^{-13}$). Methods have been developed for amplifying signals from labelled loci on chromosomes. For example, genes can be detected in-situ, that is, to determine their chromosomal location. This process using colloidal gold was used for physical mapping of genes on chromosome at the electron microscope level.

Colloidal gold is commonly used in standard electron microscopy in-situ reactions to localize a labelled DNA probe either by antibody coupling reactions or streptavidin-biotin affinity. Colloidal gold is inexpensive and simple to prepare in a variety of sizes; it is extremely electron opaque; and it does not bind adventitiously to chromatin or chromosomes. It may be used with the magnetic particles as a bridge, although it is contemplated as useful only for specific applications, for example, when it is necessary to demonstrate that magnetic beads bind specifically to loci of interest.

E. Releasing and Separating

An aspect of the invention is to release the labelled biological material from a solid support so that they can be isolated and/or sorted. This process enables the purification of the said material, that is, obtaining suspensions enriched for a particular class of structure, e.g., if the material is chromosomes, a sample of chromosome 21 may be recovered. For simple laboratory use, a 10 ml pipette was used as a separation column. A series of magnets were placed on the outside of the pipette and small magnetic particles in a buffer were allowed to fall by gravity through the pipette. These particles attached to the inside of the pipette adjacent to the magnets.

If the materials are to be used in subsequent applications wherein labels and indicators are not desirable, these may be removed from the biological material by phenol extraction, by melting the complexes off with temperatures of about 50° C., detergents, high salt concentration or treatment with a proteolytic enzyme. For instance, papain digestion may be used to cleave antibody hinge regions and so remove iron. Alternatively, other proteases could be used. Any other method to remove the magnetic particles and/or the binding composition and which does not adversely affect the structure of the biological material for subsequent applications is also within the scope of this invention.

After the biological material is labelled, the linker is cleaved and a magnetic force pulls the magnetic particles and the attached substance to be purified, such as chromosomes or small organelles, to the vessel wall or a collecting reservoir. In an illustrative embodiment, the labelled material may be pelleted in microtiter wells and purified from a supernatant by 1 g centrifugation. Unwanted particulate matter remains in suspension or at the bottom of the vessel to be discarded. Magnets such as the Bio Mag separator (Advanced Magnetics, Inc.) provide the force for magnetic separation. There are also flat magnetic separators (Advanced Magnetics) for flat tissue culture vessels.

The availability of the rapid and effective sorting method of the present invention has many applications. It allows the production of large amounts of pure chromosomes with procedures that can be conducted at the bench top for various purposes, such as library construction and cloning. As such, it facilitates the elucidation of both normal and aberrant cellular processes. The methods of this invention also permit organelles and subcellular components such as mitochondria, chloroplasts, ribosomes and Golgi apparatus to be sorted for biochemical analysis.

This invention increases the sensitivity and applicability of this procedure by employing new, more reactive magnetic microparticles to permit more rapid and efficient labelling. The present invention contemplates alternative labelling protocols using either a 1–2 step antibody sandwich or direct labelling with streptavidin-conjugated particles. One-step suspension labelling of chromosomes by direct conjugation of hybridization probes directly to microparticles is also contemplated. This procedure eliminates the necessity for reversible immobilization of chromosomes and renders the procedure more rapid and simple.

The DNA isolated from immunopurified chromosomes, in terms of its fragment size, double-strandedness, sequence enrichment, and digestibility with restriction enzymes, is suitable for use in molecular biology. Standard gel electrophoresis and dot blotting shows that the DNA from purified chromosomes is suitable for further biochemical procedures. Magnetically purified DNA/C plasmids ligated to purified chromosomal DNA can be used for transformation of $E.$ $coli.$ Labelled chromosomes are released from the solid surface by incubation with 50 mM DTT, which cleaves the disulfide linkage present in the crosslinker, and electron microscopy revealed that they are both morphologically intact and specifically labelled. Ferric oxide labelled chromosomes were then sorted in a magnetic field. These mechanisms are shown schematically in FIG. 10, a schematic representation of in-situ hybridization of electron micrograph chromosome preparations. Whole mount metaphase chromosomes were hybridized with a biotinylated DNA probe 92. Detection of the probe was with a primary antibiotin antibody 100, followed by a secondary antibody coupled to colloidal gold or magnetic particles 102. Mouse satellite DNA 90 was nick translated with biotin-dUTP 92 to yield labelled DNA 94. The DNA was hybridized with mouse chromosome preparations on electron microscope grids 96. The result is a set of labelled chromosomes 98. The hybridized biotin-labelled probe was then bound to rabbit anti-biotin IgG (an antibody) 100. For electron microscope visualization, colloidal gold was labelled with secondary antibody (goat or sheep directed against rabbit) which binds to the rabbit antibody at sites of hybridized biotin-mouse satellite DNA 102. Alternatively, labelled $Fe_3O_4$ 102 was substituted for colloidal gold. This information also demonstrated that this invention as applied worked as predicted from theory.

The present invention provides an innovative approach which combines in situ hybridization of nonisotopically labelled probes with a) reversible chromosome immobilization, and b) magnetic microparticle labelling. Reversible immobilization circumvents the aggregation/chromosome loss problems resulting from multiple centrifugation steps. The ability to reduce contaminant levels by extensive rinsing of an immobilized preparation is also an important advantage over current protocols for in situ hybridization in suspension. The use of submicron magnetic particles should minimize steric hindrance, and improve sensitivity and yield.

EXAMPLES

Example 1

Preparation of Cellular Components

A. Vertebrate animals

The mice to be used constitute a source of diploid metaphase chromosomes for application of a newly developed chromosome isolation procedure. This procedure is used to purify the mouse Y chromosome. Spleen lymphocytes are stimulated to divide with interleukin-2 to yield LAK cell cultures. Mitotic arrest of LAK cells is followed by the isolation of stabilized metaphase chromosomes. Chromosomes are hybridized with specific hybridization probes prior to labelling with magnetic particles. Labelled chromosomes are purified in a magnetic field.

The mouse is a preferred experimental animal because methods for the physical isolation of chromosomes constitute an effective alternative to FACS in this species. C57BL/ 6J is a preferred strain because the LAK cell technology, which yields large numbers of diploid cells and metaphase chromosomes for biochemistry and cytology, was developed and optimized in this strain. Furthermore, as this strain is a standard wild-type strain, any results should be representative of this species.

Mice to be used as a source of spleen cells for setting up primary cultures are sacrificed by the administration of carbon dioxide. This method is rapid, taking 2–5 minutes to kill the mice. Standard procedures as recommended by the Panel on Euthanasia of the American Medical Association and covered under "Guidelines for Euthanasia of Animals" Clamp 60-01, The Jackson Laboratory, Clinical Laboratory Animal Medicine, Bar Harbor, Me., will be used.

B. Production of LAK cell cultures

Diploid $M.$ $domesticus$ cells are obtained from spleen lymphocyte cultures stimulated to divide by recombinant human interleukin-2. Briefly, 3 minced spleens are used to set up a culture after removal of red cells by lysis, and depletion of macrophages based on their adherence to plastic. The nonadherent population is suspended in RPMI 1640 supplemented with 10% FCS, 2 mM glutamine, 10 µg/ml penicillin, 0.1 mg/ml streptomycin, 0.1 mM nonessential amino acids, 1 mM sodium pyruvate, $5\times10$-5M 2-mercaptoethanol, and 1000 units/ml recombinant human interleukin-2. Cultures are seeded at a density of $2\times10^6$ cells/ml, grown for 4 days at 37 C. in an atmosphere of 5% $CO_2$ and then subcultured every 48 h into fresh medium at an inoculation density of $1\times10^6$ cells/ml. One week old cultures are subcultured and incubated at 37 C. for 24 h prior to mitotic arrest as for L929 cells.

C. Chromosome Preparation

Two T75 tissue culture flasks of cells were initiated by standard procedures, e.g., line L929. This is enough to prepare about 8 coverslips. If more cells are needed, 4 T75 flasks may be set up. When growth of cells in the flasks was approximately 50% confluent (100% confluent would be at the point where cell growth covers the entire bottom surface area of the culture vessel), Colcemid was added to arrest the cell division (50–80 ng/ml, Gibco) and incubated at 37° C. overnight, or up to 24 h.

The metaphase cells were collected by shaking them off the bottom of the flasks. Three hard bumps was usually sufficient to dislodge all the metaphase cells. Metaphase refers to all phases of the cell cycle wherein chromosomes are sufficiently distinct (condensed) to be isolatable. This usually refers to prometaphase through later metaphase.

The metaphase cells were pelleted by centrifugation (2000 rpm for about 10 min.) and resuspended at 25° C. in about 1 ml of the same culture medium. This amount was determined empirically.

After the coverslips had prefixed for 1 h, (see step A4) the microcentrifugation chambers were set up. The transparent cap of a 15 ml Falcon tube was filled with 1M sucrose at a pH of about 8.5 to a depth of about 1 cm. The coverslip was dipped in the sucrose with the prefixed side up and should rest on the raised central portion of the chamber. There should be few mm of sucrose above the coverslip. This amount was determined empirically.

Cells were lysed in about 1% Nonidet P-40 (a detergent) at about pH 8.5. Using a Pasteur pipette, about 5 drops of cells were placed in a glass test tube. Five drops of the detergent, Nonidet P-40, were added, mixed gently with the cells, and incubated at room temperature for 1 min. The lysate was layered over the sucrose cushion in the chamber, and centrifuged for 5 min. at 3200 rpm (2500 g) at room temperature in 50 ml swinging buckets in a Sorvall GLC-28 centrifuge, or the equivalent.

The coverslip was removed from the chamber using watchmakers' forceps, and rinsed well in 0.4% Kodak Photoflo 200, at about pH 8.5, to remove the sucrose. The coverslips were rinsed briefly, about 5 min., in an excess of 2×SSC, 150 mM glycine in a beaker (50–100 mls buffer) to quench the DTSSP. The chromosomes on the coverslips were examined at this point using a 40×phase contrast microscope. To do this, sufficient 2×SSC to cover the glass (a few drops) was placed on the coverslip which was on a slide. The coverslip was kept wet at all times from this point on.

D. Whole cell lysates for organelle

Protoplasts were isolated according to Walbot and Hoisington (1982) from pea (Pisum sativum) leaf mesophyll from ten day old light grown seedlings, excised maize (Zea mays) endosperm 13 days post-pollination, Black Mexican Sweet (BMS) maize suspension culture cells, and sliced pepper (Capsicum anuum) mesocarp from mature fruit. Cells were washed several times to remove digestive enzymes and resuspended in the appropriate plastid immunolabelling buffer at 4 C. Whole cell lysates were made by immediately rupturing cells through a 37 μm mesh nylon screen in a sweeney device fitted with a syringe.

E. Antibody preparations

The α-OM polyclonal antibody was prepared by the large scale purification method by Jensenius et al. (1981) for purification of 1 gG from chicken egg yolks and preimmune serum used for control reactions was treated identically. Immunized chickens were injected with a purified outer envelope which was separated from a combined envelope fraction from Percoll purified intact pea chloroplasts (Keegstra and Yousif, 1986). The histone antisera (α-RH) control was raised in rabbits immunized again rat histone H1 subtypes (J. W. Brenemen, personal communication). Aliquots of these various antisera were biotinylated with NHS-LC-biotin (Pierce Chemical Co.). Streptavidin was purchased from Pierce Chemical Co.

F. Density gradient fractionation of intact plastid subtypes

Intact chloroplasts from pea and maize seedlings were recovered from continuous Percoll density gradients according to Bartlett et al. (1982) washed and resuspended in isolation buffer. Intact amyloplast preparations were made by 1 g density sedimentation for 30 min. on ice of whole chopped endosperm lysate (Shannon, 1989) from maize kernels 11–13 days post-pollination. Chromoplasts were isolated from pepper mesocarp according to Gounaris (1989). Plastid immunolabelling buffers consisted of the referenced isolation medium containing 2% nonfat milk, 20 mM KCl, and 0.05 mg/ml preimmune serum.

G. Purification of the Y chromosome

Although use of the mouse L929-major satellite test system has allowed us to develop a method and assess its efficiency, the real test of the method is isolation of a specific mouse chromosome. The inventors have isolated the mouse Y chromosome from diploid mouse cells.

The Y chromosome was chosen as a candidate for purification for several reasons. Its role in sex determination makes it great general interest. Furthermore, its centromere differs in sequence organization from those of the autosomes (Pardue et al., 1970; Jones et al., 1985), so that elucidation of its organization would clarify the problems of both centromere function and sex linkage. These considerations, and the fact that its small size means that Y-linked sequences comprise only a small percentage of the sequences contained in total genomic libraries, make enriched libraries for this chromosome highly desirable. Although the human Y has now been substantially mapped, this has not yet been done for the mouse, and is important for the purposes of comparison.

As an initial experiment to assess the efficiency of the sorting procedure, we purified the five nucleolus organizer chromosomes from the rest of the mouse chromosomes (Elsevier et al., 1975; Henderson et al., 1974). Although the NOR chromosomes will not be separated from each other, a preliminary purification experiment resulted in a high yield of chromosomes from the starting material because the mouse NOR chromosomes comprise 25% of the karyotype. This permitted examination by TEM of chromosomes in sufficient numbers to determine the percentage of labelled versus unlabelled chromosomes and measure the degree of contamination of the purified preparation. Sorting of the Y was then performed.

H. Chromosomes from Mouse LAK Cells

Purification was performed on chromosomes derived from diploid mouse cells, to minimize the effects of chromosome rearrangement in cell lines. Recently, a method has been developed for interleukin-2 stimulation of mouse spleen lymphocytes that yields suspension cultures that grow actively for up to two weeks without demonstrating obvious karyotypic changes (Narayanswami et al., 1992). IL-2 stimulated lymphocytes show high (20% after 6 h of arrest with Colcemid) levels of mitosis, and typically this procedure results in the production of $10^9$ cells per spleen, permitting both biochemical and cytological applications (Narayanswami et al., 1992).

LAK cells were prepared by IL-2 stimulation of spleen cells from male C57BL/6J mice, which respond well to this treatment. The Y chromosome can be purified using two different strategies. In the first approach, chromosomes from male mice are hybridized with Y-specific repetitive sequence probes, prior to immunomagnetic isolation. The second strategy relies on labelling with the mouse major centromeric satellite, to permit selective removal of the mouse X and autosomes.

I. Metaphase Chromosomes and Chromosome Fragments from Mouse.

The present invention contemplates a protocol for the immunomagnetic purification of specific metaphase chromosomes and chromosome fragments from the mouse. Efficient methods for mouse chromosome purification are needed to facilitate physical mapping of the mouse genome. Mouse chromosomes are difficult to sort by FACS due to their uniform DNA content. On the other hand, a recently developed suspension labelling protocol was subject to massive chromosome aggregation and losses during centrifugation steps. These problems are overcome by the present invention. Chromosomes from mouse L929 cells are stabilized with propidium iodide and hybridized in suspension with a biotin-labelled DNA probe. They are then reversibly immobilized on alginate coated substrates and subsequently labelled with biotin or streptavidin conjugated magnetic microparticles via a three-step antibody sandwich. Chromosome release from alginate is followed by separation of labelled from unlabelled material in a magnetic field.

J. Chromosome stabilization with propidium iodide

L929 cells (1 T75) were arrested with Colcemid, the mitotic cells collected by selective detachment, pelleted and resuspended in 400 ul 40 mM KCl. The cells were incubated 15 min at room temperature to cause hypotonic swelling. 400 ul of 1% Triton X-100 containing 50 µM PI was added to the cells, mixed well, and the suspension incubated 3 min at room temperature. The lysate was given 25 strokes with a 23 g syringe needle and the released chromosomes were checked visually at 40× phase contrast. The stabilized chromosomes were fixed by the addition of 1 ul of 8% EM grade glutaraldehyde. They were allowed to settle out at 1 g for 6 h-overnight before hybridization, in order to remove detergent and residual glutaraldehyde. The supernatant was removed prior to hybridization.

High levels of labelling with the short sandwich and direct labelling schemes were obtained. Hybridized chromosomes were anchored on alginate prior to incubation with either secondary reagents and/or magnetic particles and rinsing, and the cushion dissolved after labelling. Released chromosomes were examined in the TEM for labelling, both specific and nonspecific.

Although good levels of labelling of PI stabilized chromosomes with biotinylated probes are routinely obtained, there are possible problems with these chromosomes. PI stabilization results in chromosome condensation, thus rendering target sequences less accessible to probe. However, the degree of condensation is determined by the PI concentration of the isolation buffer and can be varied in a reproducible manner (Aten et al., 1987). Moderate PI concentrations of 25 uM are routinely used, but lower concentrations of intercalator are still effective in chromosome stabilization (Narayanswami, unpublished). Thus, probe access can be improved by using lower concentrations of PI. The use of other intercalating agents may also be effective. Finally, the routine use of chemically biotinylated RNA probes would also result in higher levels of labelling, as discussed above. Efficient labelling of chromosomes is a key step in the design of a rapid and sensitive physical isolation method.

K. Suspension hybridization of propidium iodide stabilized metaphase chromosomes Sedimented, fixed, PI stabilized chromosomes were resuspended in 100 µl of the same hybridization buffer as for EM in situ hybridization. Buffer contained undenatured probe at 4 µg/ml. The suspension was incubated at 73 C. for 30 minutes in a Lauda water bath to ensure denaturation of both probe and target sequences. The temperature was then reduced to 30 C. and the chromosomes were incubated overnight. Hybridized chromosomes were diluted ten-fold with distilled water before immunomagnetic labelling or immobilization.

Example 2

Anchoring and Isolation of Cellular Components

A. Anchoring of chromosomes

PI chromosomes were centrifuged onto alginate through a 1M $CaCl_2$ cushion and examined in phase contrast. Cushions were then soaked in EDTA for 5–10 min. Chromosomes immobilized on alginate/PEI were removed by soaking the cushion in 0.5M EDTA with the addition of 50 mM dithiothreitol (EDTA/DTT). Detached chromosomes were collected, centrifuged onto EM grids, and examined by TEM.

PI stabilized chromosomes centrifuged onto alginate cushions can be completely detached from the substrate with EDTA, which leaves the chromosomes intact while completely dissolving the cushion. However, a small percentage of chromosome detachment occurs during prolonged series of incubations.

PEI/DTSSP crosslinked alginate cushions show no chromosome detachment during labelling procedures. Reversal of the immobilization procedure results in recovery of essentially 100% of the chromosomes and complete dissolution of the cushion.

Denaturation of chromosomes on the cushion tends to disrupt it, so that a contemplated best mode of the invention is to perform denaturation and probe hybridization in one step in suspension to glutaraldehyde fixed PI chromosomes before immobilization (Stuart et al., 1978). Under these conditions we obtain nearly control (EMISH) levels of probe hybridization as assayed by colloidal gold labelling. Hybridized chromosomes are then centrifuged onto alginate for labelling.

PEI/DTSSP crosslinked alginate constitutes an effective reversible immobilization system with which stabilized metaphase chromosomes can be affixed to a surface, labelled with magnetic beads, and removed with essentially 100% efficiency.

B. Anchoring and Isolation of Mouse Chromosomes

The mouse L929 cell chromosome system was used to perform experiments designed to assess the efficiency of the immobilization protocol, because large quantities of chromosomes can be easily obtained from this cell line. Mouse satellite DNA was used as a test sequence to determine the effectiveness of labelling protocols because all the mouse centromeres except that of the Y label heavily with this probe (Pardue and Gall, 1970).

Centromeric satellite DNA from mouse chromosomes was used as a probe in a series of reactions to determine binding capacity of various magnetic particles. Results of a series of reactions in Table 1 illustrate the binding capacity of various magnetic particle compositions.

TABLE 1

In-Situ Hybridization Experiments.

| REACTION # | PROBE | LABEL | PROTEIN CONJUGATION |
|---|---|---|---|
| 1. | L929 sat DNA | biotin | Streptavidin gold (10 nm) |
| 2. | L929 sat DNA | " | SA gold (10 nm) - biotin $Fe_3O_4$ |
| 3. | L929 sat DNA | " | RαR.biotin - SA gold (15 nm) - biotin $Fe_3O_4$ |
| 4. | L929 sat DNA | biotin | RαR.biotin - SA (naked) - biotin $Fe_3O_4$ |
| 5. | L929 sat DNA | " | Rα biotin - GαR gold (15 nm) |
| 6. | L929 sat DNA | " | Rα biotin - GαR $Fe_3O_4$ |
| 7. | L929 sat DNA | " | Rα biotin - Gα biotin - Rα biotin - Gα R $Fe_3O_4$ |
| 8. | L929 sat DNA | " | Rα biotin - GαR.biotin - SA - GαR biotin - Rα $Fe_3O_4$ |

Rα = Rabbit anti-
Gα = Goat anti-

The signal appeared at the centromeres of every chromosome, facilitating detection of low frequency events. Colchicine treated mouse L929 cells were used to prepare chromosome spreads (this is a modification for chromosomes of a method reported by Miller, 1969; see also Hamkalo et al., 1978).

As a control, reaction 1 (Table 1) was directed to visualize the colloidal gold reaction (see FIG. 7). Reaction 2 bound iron oxide particles to the colloidal gold (see FIG. 8), but at a low frequency. Reaction 4 is a scheme used for signal amplification, addressing the question regarding stearic hindrance, that is, 1) does the signal need to be amplified to be detected by a 500 nm (0.5 micron) $Fe_3O_4$ particle; 2) does signal amplification increase the frequency of signal. The answer to 1 is no. The answer to 2 is yes. A positive amplified reaction product was observed at the centromeric regions (FIG. 9).

Figure 15:
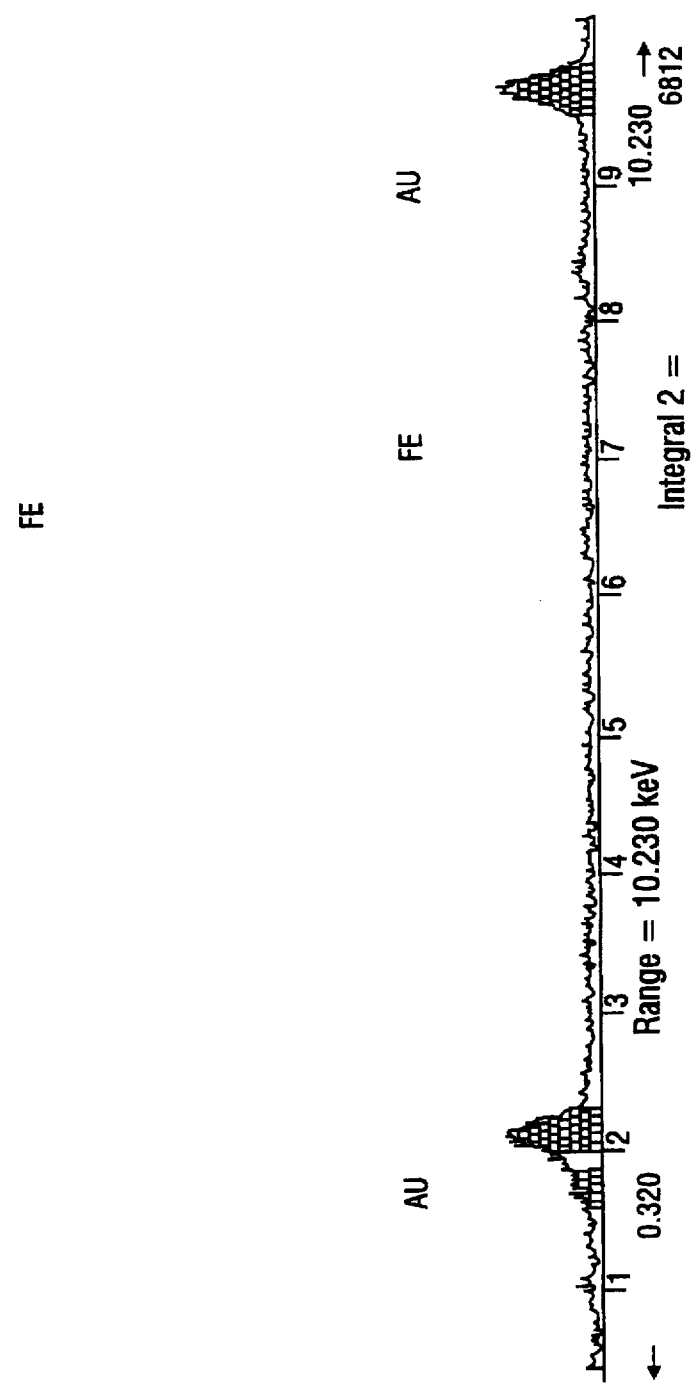
FIG. 15 is a graph which illustrates results of energy dispersive x-ray microanalysis on a non-reactive chromosome from Reaction 3 (Table 1 of Example 1).
Figure 16:
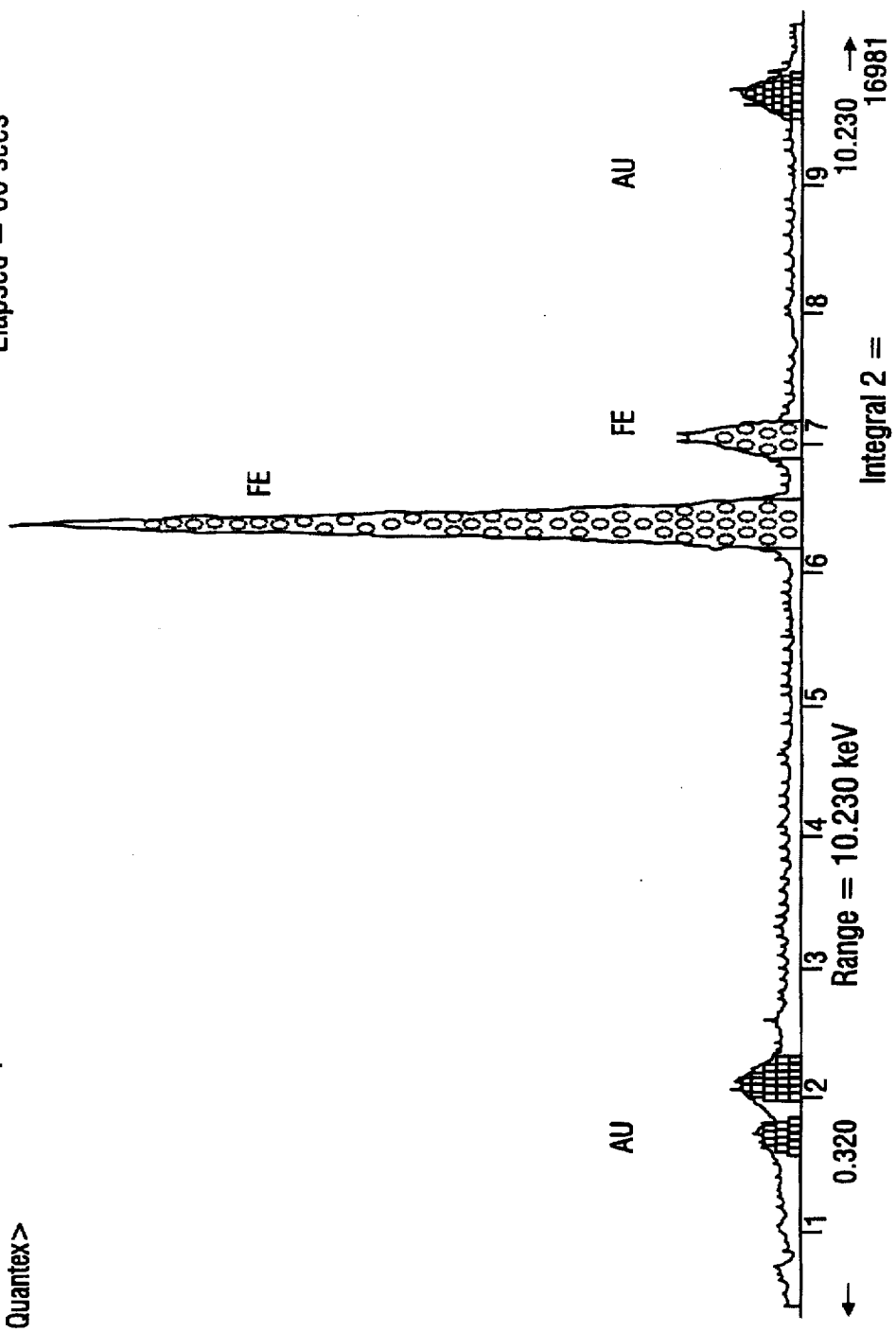
FIG. 16 is a graph which illustrates results of energy dispersive x-ray microanalysis of a reacted chromosome illustrating K$\alpha$ and K$\beta$ peaks for iron (see also FIG. 15).

The reaction product was unequivocally determined to be iron by energy dispersive x-ray microanalysis. FIG. 15 is a graph which illustrates results of energy dispersive x-ray microanalysis on a non-reacted chromosome from reaction 3 (Table 1). In this analysis, electron beams interact with molecules to emit x-rays characteristic of the molecules. L and K refer to electron shells. The $L\alpha$ and $L\beta$ peaks (to the left) and the $K\alpha$ and $K\beta$ (to the right, shouldered together) are for gold (Au) and are detected from an EM grid. There is no iron detectable. FIG. 16 is a graph which illustrates results of energy dispersive x-ray microanalysis of a reacted chromosome illustrating $K\alpha$ and $K\beta$ peaks for iron (see also FIG. 15). Labelling with magnetic particles was therefore achieved.

Figure 17A:
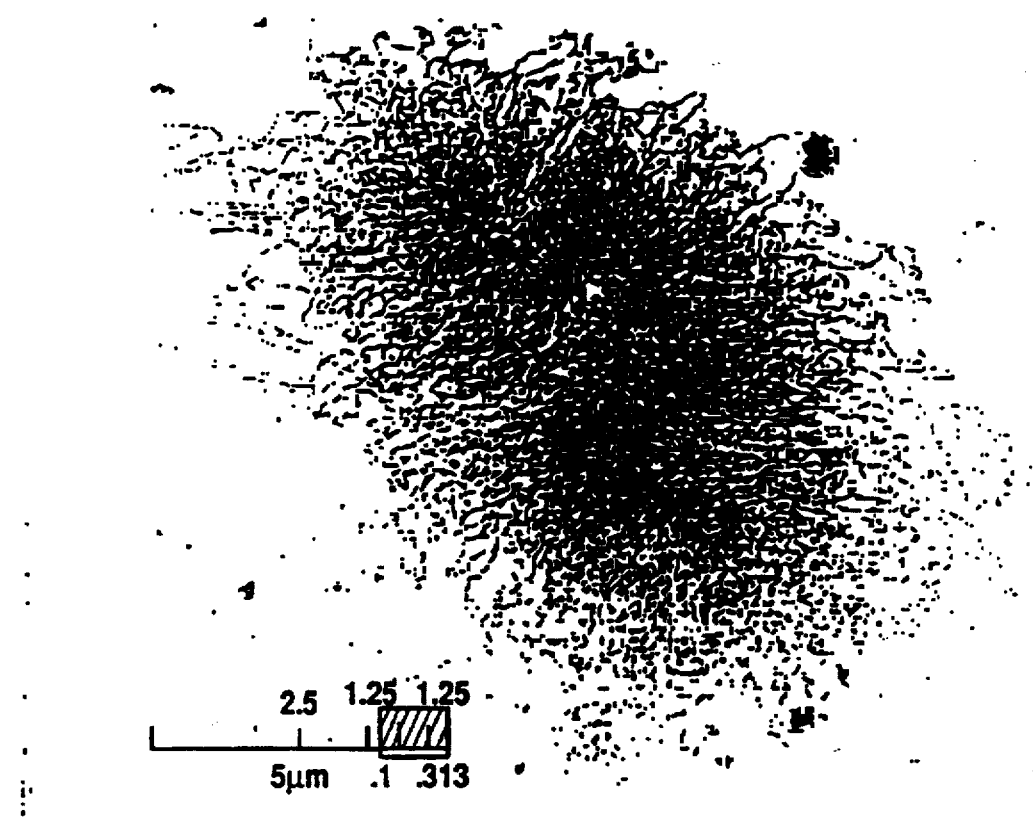
FIG. 17A–B illustrate the size and internal composition of one of the classes of biological materials referred to in this invention, chromosomes.
Figure 17B:
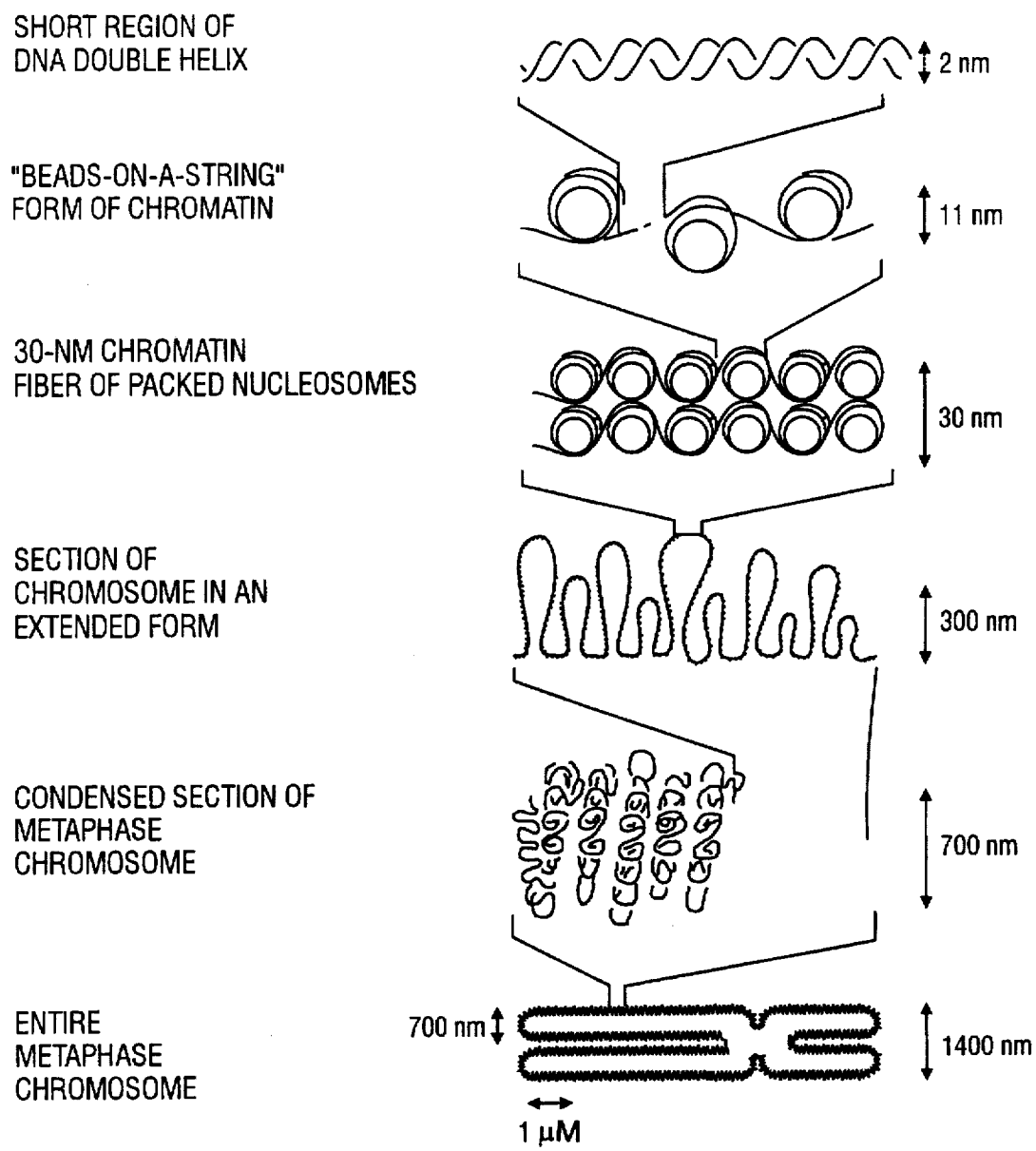

There was no evidence of the steric hindrance that might have been expected based on the supercoiled chromosome structure (FIG. 17A). FIGS. 17A-B illustrate the size and internal composition of one of the classes of biological materials referred to in this invention, chromosomes. FIG. 17A is an electron micrograph of a single chromatid of a mitotic chromosome from an insect (Oncopeltus) treated to reveal loop chromatin fibers that emanate from the central axis of the chromatid. FIG. 17B is a schematic illustration of the many orders of chromosome packing postulated to give rise to the highly condensed metaphase chromosome. A short region of DNA double helix is illustrated in 120 and packed into "beads on a string" 122. 30 μm chromatin fibers are comprised of packed nucleosomes 124. In an extended form 126, the chromosome may be viewed as a long string, condensed at metaphase 128 to be viewed with the light microscope 130. (adapted from Albert et al. 1989)

C. The mouse NOR chromosomes

Evidence from the *X. laevis* cell line XTC demonstrates that middle repeat sequences such as the 18S+28S ribosomal RNA genes can be detected with magnetic particles. The mouse 18S+28S ribosomal RNA genes, which are located at the NORs, comprise such a middle repeat sequence and are easy to label with magnetic particles because preliminary EMISH has shown that these sequences label to high levels with colloidal gold (Narayanswami, unpublished).

LAK cells were arrested for 6 h with Coicemid. PI stabilized chromosomes were prepared, and interphase nuclei were removed either by sedimentation at 1 g for 30 min or by mild centrifugation. The suspension of chromosomes was hybridized with biotin labelled pXlr101, labelled with magnetic particles, and the labelled chromosomes were separated by passage over a magnetic affinity column. The effectiveness of the sorting procedure was assessed in the TEM after centrifugation of the chromosomes onto an EM grid.

D. The Y chromosome

Sorting of the Y chromosome can be performed in two ways. First, direct purification of this chromosome can be accomplished by hybridization with probes for known Y-linked repeated sequences. We have chosen the sequences YB10, which consists of a 310 bp sequence repeated approximately 500 times in the Y chromosome, and pERS5A, which is also concentrated on the Y (Eicher et al., 1989; Eicher et al., 1991). Immunomagnetic labellings can be performed using these probes either singly or in combination.

In the second strategy, purification of the Y can be accomplished by hybridization with pSAT1. Mouse major satellite is present on all the mouse chromosomes with the exception of the Y (Pardue et al., 1970). The mouse X and autosomes can therefore be separated from the Y when labelled chromosomes are placed in a magnetic field, leaving the Y chromosomes in suspension. This latter approach has the advantage that an extremely highly repetitive sequence can be used, and that it will not be necessary to remove the magnetic tag from the Y chromosomes prior to biochemical manipulations.

Two Y-linked repeated sequences have been chosen to be used as probes for sorting the Y for several reasons. First, although YB10 is localized exclusively on the Y chromosome (Eicher et al., 1989) and consists of a 150 kb tandem array, the current lower limit of detection is 4500 kb, which gives a moderately large signal with old Molday particles. The new Molday particles, being 100 times more sensitive, improves our level of detection sufficiently to visualize a 150 kb cluster. In addition, recovery may be improved by including pERS5A in the experiment, because this sequence is also known to be highly repeated in the Y and gives an intense signal with fluorescent in situ hybridization (Eicher et al., 1989). One potential drawback to this strategy is that pERS5A detects GATA/GACA repeats, which are present at low levels in the rest of the mouse genome. However, this should not be a problem, first, because magnetic particles should not detect these interspersed sequences, due to their relatively low level of repetition, and second, because the strength of a magnetic field may be modulated in such a way that only heavily labelled chromosomes are recovered. Finally, hybridization stringency can also be modulated to favor hybridization with Y-associated sequences. Consequently, this strategy results in considerable enrichment for Y DNA, even if a small percentage of other chromosomes are present in the sample.

It is possible that the second of the two strategies for purifying the Y will compromise the quality of the sorted preparation because any chromosome fragments present in the suspension will remain mixed with the Y chromosomes. However, such fragments should not appreciably contaminate Y chromosomes prepared in this way because PI chromosomes are more condensed than in the absence of intercalating agents. Subsequent glutaraidehyde fixation results in considerable further stabilization, and EM examinations of these chromosomes, both at all stages of the preparative procedure and after storage for 1-2 weeks, have failed to demonstrate any appreciable degree of chromosome breakage.

Successful purification of the mouse Y is only one example that illustrates the possibility of the construction of an enriched library. It is understood that this method may be applied to the purification of any other mouse, human, or higher eukaryote chromosome and that the use of the invention for such purification would fall within the spirit and the scope of the present claimed invention.

E. Isolation and Sorting of a Human Chromosome from a Mouse-Human Hybrid Cell Line In order to sort a specific chromosome, and to determine the purity of the sorted preparation, a mouse-human hybrid cell line was used. This line contains a single intact human chromosome No. 1. Cells were mitotically arrested, metaphase cells were harvested by selective detachment and chromosome preparations were immobilized as in Example 1. After immobilization, chromosomes were labelled with a probe for human satellite III (Cooke and Hindley, 1979) which occurs as a large block at a pericentric location on the q-arm of chromosome No. 1. Although Satellite III itself occurs on several human chromosomes (Cooke and Hindley, 1979), an alphoid repeat has also been identified that hybridizes specifically to the centromeric region of chromosome No. 1 (Waye et al., 1987) thus allowing sorting of chromosome 1 from both cell hybrids and diploid human tissue. Hybrids were detected with an antibody sandwich procedure followed by reaction with biotinylated ferric oxide in preparation for magnetic isolation. Chromosomes were sorted in a magnetic field as shown in FIG. 11. The sorted preparations were then examined by light microscopy for alteration in morphology and any contamination with mouse chromosomes, which are readily identifiable because of their distinct morphology. Gel electrophoresis was used to estimate the molecular weight of chromosomal DNA. Finally, the DNA from the sorted chromosomes was subjected to blotting and hybridization with appropriate probes (i.e., satellite III) in order to confirm that human chromosome No. 1 had been sorted. This example demonstrates the feasibility of sorting by magnetic particle labelling by isolating chromosome No. 1.

F. Immunomagnetic methods can be used to isolate many chromosomes or chromosomal regions of interest.

Specific mouse chromosomes can be isolated from hybrid cell lines already in existence by using species-specific LINE repeats (Rikko et al., 1991) as hybridization probes. EM in situ hybridization with such probes will differentiate chromosomes of varying origin in cell hybrids (K. Lundgren, unpublished). Furthermore, it is also possible to exploit differences between the LINE repeats of *Mus domesticus* and *Mus spretus* to separate their chromosomes in hybrid cells (Rikko et al., 1991).

An advantage of the mouse system is that it is possible to create an artificial chromosome-specific sequence for probe hybridization by integrating a transgene array into the genome. This eliminates the need for naturally occurring chromosome-specific probes and permits purification of any mouse chromosome with a universal hybridization probe.

Such purified chromosomes have diverse uses. For example, DNA from preparations of individual mouse chromosomes can be electrophoresed in each lane of a gel, and the result blotted and hybridized with an unknown cloned DNA whose chromosomal assignation is desired. Although in the mouse, chromosomal assignations are currently done using a backcross panel, such blots would be very useful in analyzing human or other genomes, and constitute a potentially valuable resource.

Centromere-enriched libraries can be produced by cutting mouse DNA with an artificial restriction enzyme (Moser et al., 1987). Such an enzyme could be constructed by scanning for triple helix forming sequences in the 18S+28S RNA sequence, which is known to be embedded in major satellite (Narayanswami, unpublished) at the centromere-arm border. The triple helix forming sequence can be attached to an iron-EDTA moiety that will cleave DNA at the site of triple helix formation. Since the nucleolus organizer chromosomes make up 25% of the mouse karyotype, this gives a high yield of centromere fragments for cloning. A similar approach can be employed for *M. spretus* and *M. caroli* chromosomes.

Artificial restriction enzymes can be designed to cleave the mouse major satellite and the *M. caroli* satellite, both of which are known to be localized at the centromere-armborder (Narayanswami et al., 1992). In the case of *M. spretus*, at least 80% of the chromosomes should be cleaved (Narayanswami et al., 1992). This approach should permit interspecific comparisons of centromere organization in the mouse.

Centromere fragments can be used as artificial chromosomes after ligation of a selectable marker and a second telomere, reintroduction into cells and analysis of segregation. Specific chromosomes isolated by immunomagnetic purification can be introduced into living cells by injection, for example. This approach, whereby entire centromeres are isolated and used as vectors, would complement existing approaches, such as the use of double-minute chromosomes as megabase cloning vectors (Hahn et al., 1992), in addition, the new approach would have the advantage that the products would be expected to show Mendelian segregation.

In the absence of a suitable chromosome-specific sequence for in situ hybridization, chromosomal proteins can be used for chromosome isolation. For instance, antibodies to nucleolus organizer (NOR)-associated proteins can be conjugated to magnetic microparticles and used to purify the mouse NOR chromosomes. This approach has the advantage that it does not require denaturation of chromosomal DNA.

Unrearranged mouse DNA fragments can be prepared in bulk by employing a modification of the method described by Kandpal et al in (Kandpal et al., 1990). In their method, DNA fragments generated by digestion with restriction endonucleases have their ends rendered single-stranded. Hybridization to a biotinylated oligonucleotide is followed by purification over a streptavidin affinity column.

Further applications of this technique would include, but would not be limited to immunomagnetic chromosome isolation in the purification of chromosomes from solid tumors, where the small amount of starting material makes FACS impractical, preparing source DNA in large quantities from Interleukin-2 stimulated mouse lymphocytes (Narayanswami et al., 1992), obviating the cloning step prior to sequencing and isolating chromosome 17 using a repetitive probe that is unique to t-haplotypes (K. Artzt, pers. comm). In addition, the preliminary digestion step can be avoided by conjugating microparticles to triple helix forming sequences.

G. Isolation of Chloroplasts by Magnetic Particles

Chloroplast polypeptides are reactive with anti-idiotypic antibodies, providing a label to distinguish chloroplasts by their different protein compositions (Pain et al., 1988). Chloroplasts are magnetically labelled by methods analogous to that used for chromosomes. Initially, chloroplasts are immobilized, or unfixed and successively incubated with anti-idiotypic antiserum and goat anti-rabbit IgG conjugated to 50 nm magnetic particles. Immobilized chloroplasts are incubated with 50 mM HEPES/KOH, pH 7.7, 0.66M sorbitol for 1 min at 4° C., then with an ice-cold aldehyde fixative (0.05% glutaraldehyde+25% paraformaldehyde) in the same buffer for 30 min at 4° C. After washing with buffer A (50 mM HEPES/KOH, pH 7.7, 0.33M sorbitol, 40 mM $KOA_c$, 2 mM Mg $(OAc)_2$) containing 10 mM $NH_4Cl$ and buffer A plus 2% BSA (bovine serum albumin), the samples are incubated with decomplemented anti-idiotypic rabbit antiserum (1:500) in buffer B (Buffer A, 1% BSA, 1 mM phenyl methyl sulfonyl fluoride (PNSF)) for 2 h at room temperature, washed and incubated with goat IgG (100 $\mu l^{-1}$)

in buffer B. The samples are washed as above and incubated with goat anti-rabbit IgG conjugated to colloidal gold if desired (10 nm, 1:50, Janssen). The samples are washed with Buffer A, immersed in Karnovsky's aldehyde fixative containing 0.33M sorbitol (1 h), osmicated (1 h), stained with uranyl acetate (2 h) and dehydrated in graded series of ethanol as described (Kanwor, Y. S. and Farguhar, M. G., *J. Cell. Biol.*, 81:137–153 (1979)).

Protoplasts are lysed by physical disruption into the isolation buffer described in Gruissem et al. (1983) or Schreiber et al. (1988). Chloroplast isolation is performed according to conditions established by Grossman et al. (*J. Biol. Chem.* 257:1558–1563, 1982) and magnetic immunoprecipitation as described in the present application. Sorting is accomplished in a magnetic field.

H. Reversible anchoring on alginate coated supports

There are several possibilities in developing a reversible anchoring system that would permit labelling and recovery of propidium iodide stabilized chromosomes.

In initial studies the properties of glass surfaces coated with the thiol cleavable crosslinker, dithiobissulfosuccinimidylpropionate (DTSSP) (Staros, 1982; Narayanswami et al., 1992) were investigated. Although both labelling and recovery of Miller-spread chromosomes are good, PI stabilized chromosomes inconsistently detached from the substrate on reversal of immobilization.

Therefore a system was developed to exploit the properties of surfaces coated with the polysaccharide alginate, which is found in brown algae. Alginate is characterized by solidification in the presence of a counter ion such as calcium. The resulting gel will, however, dissolve in the presence of chelating agents such as EDTA. Its properties make it a preferred reversible immobilization system.

The use of alginate as a support requires the presence of a counter ion throughout the procedure. If the counter ion is omitted, some disruption of the support and consequent chromosome detachment occurs as the counter ion is leached out of the gel. However, agents such as polyethyleneimine (PEI) can be used to further stabilize the support by the introduction of amino groups that can then be crosslinked. This results in the formation of a network interdigitating with the alginate. The resulting gel is stable in the absence of the counter ion. If a cleavable crosslinker such as DTSSP is used to crosslink the PEI, the resulting gel is dissolvable in the presence of EDTA and a reducing agent.

I. Reversible anchoring of chromosomes on Alginate/PEI

Although the reversible anchoring of propidium iodide (PI) stabilized metaphase chromosomes was possible on alginate/PEI, the most effective attachment and recovery after labelling conditions were determined before proceeding with immunomagnetic labelling of chromosomes.

PI Stabilized metaphase chromosomes from mouse L929 cells and phase contrast microscopy of alginate pads (alginate is optically clear) were used to assess the properties of the reversible anchoring system. 1.5% alginate was used to coat 1 cm glass coverslips. The solidified supports were then soaked in PEI of various concentrations for varying amounts of time. This was followed by prefixation with dithiobissulfosuccinimidylpropionate (DTSSP), centrifugation of chromosomes onto the pads, postfixation with DTSSP in order to attach the chromosomes to the alginate/PEI, reversal with 0.5M EDTA/50 mM DTT, and examination in the phase contrast microscope. Released chromosomes were recentrifuged onto EM grids for examination.

The best reversal occurred when alginate coated supports were soaked in 0.05% PEI for 1 minute, followed by centrifugation of chromosomes and postfixation with 1–10 μM DTSSP for 1 minute. Prefixation of the support was not necessary, and indeed, detrimental to chromosome detachment. Chromosome detachment was complete after 10 mins incubation in EDTA/DTT, and the chromosomes were readily visible as individual chromosomes suspended in the supernatant. Essentially 100% of the chromosomes were removed from the substrate and the morphology of released chromosomes appeared in the EM to be indistinguishable from controls.

During immunomagnetic labelling experiments it was verified that chromosomes remained attached to the surface of the alginate pad throughout the entire procedure. No detachment of chromosomes was observed during the procedure. Reversal with EDTA/DTT, although it cleaves the disulfide linkages in DTSSP, has no effect on antibodies or particulate tags attached to chromosomes, as evidenced by the presence of intact signal on detached chromosomeslabelled on alginate/PEI. Alginate/PEI crosslinked with DTSSP constitutes an effective reversible immobilization matrix for metaphase chromosomes. Chromosomes remain attached to the supports during labelling procedures, and can be recovered with 100% efficiency after labelling.

J. Immuno-isolation of plastids from whole cell lysates

Figure 20A:
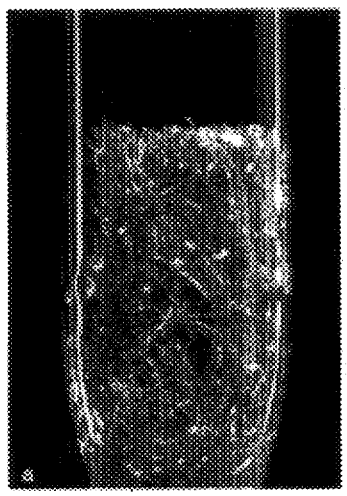
FIGS. 20A–H illustrate the isolation of various plastid forms from whole cell lysates immunolabelled with magnetic nanoparticles.
Figure 20B:
Figure 20C:
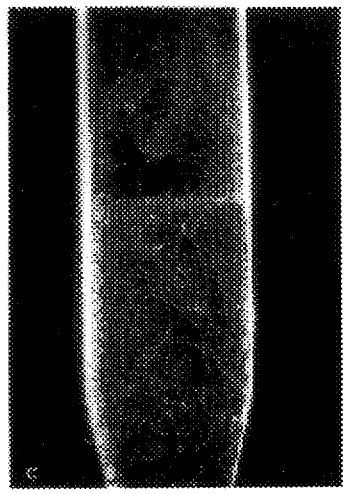

Depending on the purpose of the isolation, various plastid forms can be immunolabelled in preparations of chopped or whole tissue homogenates, lysed cells and protoplasts, or density sedimentation fractions and recovered from magnetic affinity columns (FIGS. 20A–H). The columns used for the various whole cell lysate separations were identical to those used to recover prefractionated chloroplasts (FIG. 20A). The functions of the column matrix are to increase the magnetic surface area and to reduce the average distance that the weakly magnetically labelled organelles must travel through the isolation buffer before adhering to a magnetic surface. Once the organelles are bound to a ferromagnetic surface, the flow can be increased significantly to reduce retention of unlabelled cell debris without eluting specifically labelled organelles. Each column was first sterilized with ethanol and then rinsed with ten volumes of isolation buffer prior to loading (FIG. 20A). The optimal flow necessary for adequate separation of an organelle depends on the size and the density of the organelle, the viscosity of the isolation buffer, as well as the number of magnetic particles specifically adhered to the organellar surface.

Figure 20D:
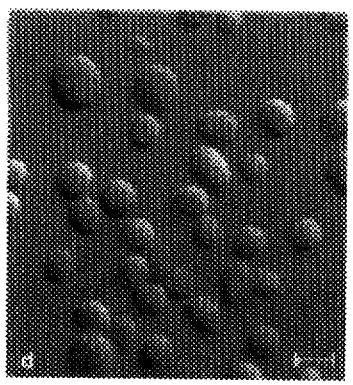
Figure 20E:
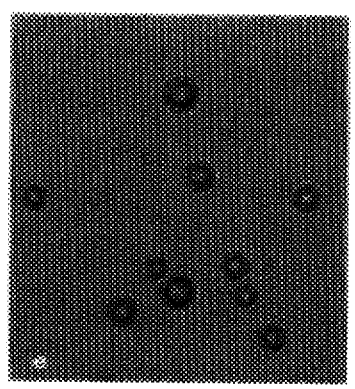
Figure 20F:
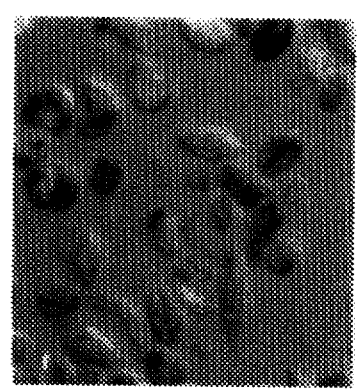
Figure 20G:
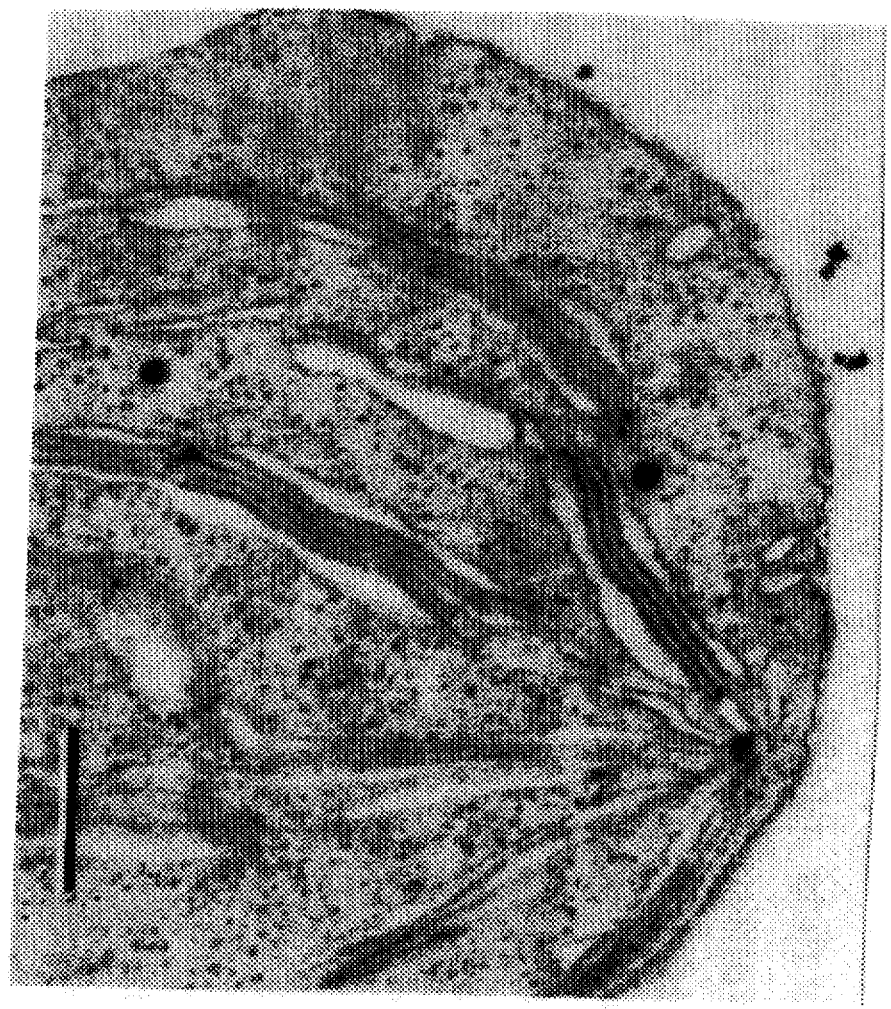
Figure 20H:

The parameters defined by recovery of prefractionated leaf mesophyil chloroplasts were applied as an approximation for isolation of other plastid subtypes. Aliquots of whole cell lysates (500 μl) were not reacted with a primary antisera or incubated with 300 μg of either biotinylated antihistone, preimmune sera, or α-OM for twenty minutes on ice in the dark, followed by a ten minute incubation with 100 μl streptavidin conjugated nanoparticles. Labelled organelles were immediately separated with isolation buffer on a magnetic affinity column adjusted to a flow rate of 300 μl/min. at 4 C. in a high gradient magnetic field. After washing the column with approximately ten volumes of the appropriate isolation buffer at a flow rate of 1.5 ml/min., chloroplasts (FIG. 20B) and chromoplasts could be observed adhered to the column matrix. The column was removed from the magnetic field, briefly demagnetized, backflushed with 1.0 ml isolation buffer, separated and washed again before the plastids were eluted. Plastids labelled in whole cell lysates were eluted from the column as before by backflushing isolation buffer up through the column (FIG. 20C) after a brief demagnetization to remove hysteresis. Chloroplasts, amyloplasts, and chromoplasts were isolated from lysed protoplasts and examined for purity by phase and differential interference contrast microscopy (FIGS. 20D,E,F). The plastid preparations recovered from the columns appear free of contaminating cell debris. Whole cell lysate from maize endosperm and amyloplast preparations made by density sedimentation in isolation buffer (Shannon, 1989) contained particulate debris readily observed with phase contrast and dark field optics which were absent in preparations made by magnetic immunoabsorption. Transmission electron microscopy of pea chloroplasts shows these preparations made from whole cell lysates to be isolated from other cellular structures and ultrastructurally intact. (FIG. 20G). Magnetic nanoparticles were often observed between agglutinated chloroplasts. The particles adhered to the outer envelopes of magnetically separated plastids (FIG. 20H) appear to be localized slightly off the surface of the outer plastid membrane accountable by the dextran which surrounds the electron dense magnetic core of a Molday type particle.

K. Immunomagnetic labelling and recovery of immobilized metaphase chromosomes.

Although it was determined that streptavidin-conjugated Molday particles and Immuncotype particles can be used to specifically label both normal and PI stabilized metaphase chromosomes (Narayanswami, unpublished) it was necessary to demonstrate that labelling could be performed on chromosomes immobilized on alginate/PEI, and that such chromosomes can be isolated in a magnetic field.

Glutaraldehyde fixed, PI stabilized chromosomes from mouse L929 cells were hybridized in suspension with biotin labelled pSAT1, immobilized on alginate/PEI and labelled with rabbit-anti-biotin AB, biotinylated goat-anti-rabbit AB and streptavidin conjugated magnetic particles for 20 mins-12 h. Extra avid 60 nm magnetic particles were used as defined by the amount of streptavidin conjugated to their surfaces (Kausch, unpublished). Preparations were rinsed, chromosomes detached as above, and the released chromosomes centrifuged on to EM grids for further examination. In general, reactions were run in low salt with the addition of 50 mM calcium chloride to preserve the integrity of the alginate pad.

The effectiveness of modifications to the labelling procedure on alginate were assessed by comparison to gold labelled controls. In certain cases, chromosomes were detached from alginate prior to labelling with magnetic particles, recentrifuged onto EM grids, and labelled with colloidal gold as for EM in situ hybridization (EMISH). For instance, chromosomes labelled with rabbit-anti-biotinAB on alginate can be detached, sedimented on an EM grid, and labelled with secondary antibody and gold as for EMISH. A positive signal demonstrates that primary antibody labelling on alginate has been successful.

To determine whether labelled chromosomes were sensitive to a magnetic filed, iron labelled chromosomes were prepared as described above, mixed with unlabelled chromosomes, and the mixture exposed for 5 minutes to a magnetic field generated by a large permanent rare-earth magnet. Chromosomes remaining in the supernatant were centrifuged onto an EM grid and examined for the presence of iron particles.

Thus it was possible to demonstrate that in situ hybridized chromosomes can be labelled successfully with magnetic particles (FIG. 1). Detached chromosomes, when recentrifuged onto EM grids, are seen to be labelled at their centromeres. Nonspecific labelling of chromosome arms is low.

A large specific signal was also observed after as little as 20 minutes labelling with magnetic particles. As chromosomes are rendered sensitive to a magnetic field by the presence of 1–10 particles, this suggests, that in the case of highly repeated sequences, specific labelling of chromosomes could be achieved in 10 minutes or less. Under the conditions used, essentially all the chromosomes were removed form mixtures of labelled and unlabelled chromosomes.

Thus, stabilized metaphase chromosomes can be specifically labelled with magnetic particles while immobilized on alginate/PEI. Labelling is rapid, taking as little as 20 mins. Labelled chromosomes can be purified in a magnetic field with high efficiency.

Example 3

Preparation of Solid Support

A. preparation of Coverslips

Glass coverslips preferably round, and which are about 1 cm in diameter, were acid washed, usually in HCl. Coverslips were then rinsed thoroughly in distilled water and dried, silanated according to methods of Pierce Chemical Co. (see section H1), air dried and stored at room temperature until needed.

The coverslips were prefixed by incubating each coverslip in 1 mM dithiobis-sulfa succinimidyl propionate (DTSSP) (freshly made up in 2×SSC) for 1 h at room temperature in a petri dish. The DTSSP solution generally was placed only on the top surface of the coverslip with a Pasteur pipette. Other reversible crosslinkers, e.g., SPDP, may be substituted. Mitotic cells were harvested from the tissue culture vessels while the coverslips were prefixing.

B. preparation of alginate coated supports

Cushions of alginate on glass coverslips were prepared by dipping the coverslips in a 1% solution of TIC alginate in water and placing the coated Coverslip in 1M $CaCl_2$ to solidify. The resulting cushions are optically clear, so that chromosome attachment and removal can be monitored by phase contrast microscopy. Alternatively, alginate cushions were soaked for 2 h in 0.5% PEI, followed by incubation for 2 min in 1 mM DTSSP prior to attachment of chromosomes.

Example 4

Labelling cellular components with an indicator

A. Labeling of cellular components with streptavidin labelled magnetic particle

The availability of extra-avid magnetic particles suggests the possibility of labelling hybridized chromosomes directly. That is, stabilized chromosomes can be hybridized with probe, immobilized on alginate, and then reacted with streptavidin labelled nanoparticles. Immobilization in this scheme is useful due to the presence of unhybridized probe in the suspension of labelled chromosomes, with which streptavidin-iron would bind if the reaction were performed in suspension. However, centrifugation of chromosomes through a cushion onto either an EM grid or an alginate pad removes unhybridized probe, which remains at the top of the cushion, so that the particles should react only with sites carrying hybrids.

EMISH data suggests that direct labelling is a viable approach. PI chromosomes can be labelled in one step with streptavidin (SA)-gold if they are first hybridized with an RNA probe that has been biotinylated chemically. These probes are produced by in vitro transcription with T3/T7 RNA polymerase in the presence of allylamine-UTP and can be chemically biotinylated to levels of up to 100%. This is greater than can be achieved by nick-translation of DNA.

This approach was tested by hybridizing PI stabilized L929 cell chromosomes with an RNA probe for pSAT1 that has been chemically biotinylated. Hybridized chromosomes were centrifuged onto EM grids and labelled with streptavidin-conjugated magnetic particles. Labelling conditions can be optimized by varying probe and particle concentrations. Controls were labelled with colloidal gold.

B. Conjugation of hybridization probes to magnetic particles

If high labelling levels are obtained with the extra-avid magnetic particles, one-step suspension labelling with hybridization probes immobilized on the surfaces of magnetic particles can be performed. Suspension labelling of chromosomes is very rapid and does not require immobilization. A precedent for this approach is the use of poly-A+ RNA from cells (Homes et al., 1990). Molday particles can constitute a more efficient reagent than DYNABEADS as their small size affects the hybridization kinetics of the probe less than for the large particles.

An oligonucleotide complementary to the mouse major satellite DNA repeat was conjugated to magnetic nanoparticles by tailing the probe with biotin and reacting it with streptavidin labelled magnetic particles. This strategy is used because oligonucleotides coupled to magnetic particles by conventional means may give rise to high levels of nonspecific labelling.

PI chromosomes from L929 cells were hybridized under standard conditions with the particles. Different particle concentrations were used to determine optimal labelling conditions. Hybridized chromosomes were then examined by TEM for labelling. TEM examination allows assessment of the efficiency of labelling (particles per chromosome and the percentage of total chromosomes actually labelled).

C. Labeling with magnetic particles

The small size of the magnetic particles necessitated EM examination of labelled chromosomes. Metaphase chromosomes from L929 and XTC cells were prepared by a modified Miller procedure, immobilized on an EM grid, and labelled by standard EM in situ hybridization (EMISH) (Rattner et al., 1978; Narayanswami et al., 1992, Experimental Protocols section). Chromosomes were hybridized with biotinylated pSAT1, followed by sequential incubation with rabbit-anti-biotin, biotinylated goat-anti-rabbit, and streptavidin, and labelling with biotin-conjugated microparticles. Streptavidin-labelled microparticles were tested by substitution for streptavidin in the labelling procedure. Preparations were labelled in parallel with similarly derivatized colloidal nanoparticles. Controls were labelled with 20 nm colloidal gold particles as for EMISH (Narayanswami et al., 1992).

To further assess specificity, some preparations of both L929 and XTC chromosomes were labelled with streptavidin gold prior to incubation with biotin-labelled microparticles. X-ray microanalysis was performed on labelled preparations in order to determine whether bound material was in fact iron.

Both micro- and nanoparticles labelled mouse centromeres with high specificity and efficiency (80%) in the case of biotin-labelled microparticles and 100% in the case of nanoparticles derivatized with either biotin or streptavidin), compared to controls. There is also negligible levels of nonspecific labelling of chromosome arms.

Chromosomes from XTC showed labelling only at the NORs, which take the form of cytologically distinct secondary constrictions (Narayanswami et al., 1990). Interestingly, magnetic particles labelled the smaller of the two NORs efficiently. This NOR is homologous to the diploid X. laevis NOR (Schmid et al., 1987), which contains 450 copies of the 18S+28S ribosomal RNA repeat per haploid genome. This cluster thus constitutes a typical middle repeated sequence.

Preparations labelled with streptavidin-gold prior to incubation with biotin-labelled microparticles showed magnetic particles only in regions previously labelled with gold. X-ray microanalysis of these preparations showed that the bound material was in fact ferric oxide (Kausch, unpublished results).

Both magnetic micro- and nanoparticles can be used to achieve efficient specific labelling of metaphase chromosomes. Levels of nonspecific labelling are negligible. The lower limit of detection with these particles is intermediately repetitive DNA sequences.

D. Labelling of propidium iodide stabilized chromosomes with magnetic particles

Chromosomes spread by a modified Miller procedure, although constituting excellent substrates for labelling with magnetic particles, are unsuitable for sorting because they decondense in the spreading solution. This causes attachment of the chromosomes to one another by unwound DNA at their peripheries and results in cross contamination of sorted preparations (Narayanswami, unpublished observations). Labelling was therefore repeated using metaphase chromosomes prepared as for flow cytometry.

Four different chromosome stabilization methods were tested: 1. hexylene glycol, 2. magnesium sulfate, 3. the polyamine method, and 4. stabilization with propidium iodide (PI) (Bartholdi et al., 1987). Stabilization with PI was further investigated because among the protocols examined, chromosomes prepared in this way have the best morphology and a moderate degree of condensation. Chromosomes prepared by the other methods are so condensed that individual chromosomes are no longer easily distinguishable, and furthermore, are poor substrates for probe hybridization and labelling (Narayanswami, unpublished). In contrast, PI chromosomes are labelled by EMISH with colloidal gold essentially to control levels. Furthermore, they are easy to prepare with minimal equipment (a syringe fitted with a 23 g needle) and without the use of complex detergent solutions. They are stable in suspension for several days, and contaminating interphase nuclei can be quickly removed by sedimentation at 1 g for 20–30 min. Chromosomes can be fixed in suspension with glutaraldehyde, after which they can be stored at 4C. for several weeks without apparent deterioration. They can be pelleted by overnight sedimentation at 1 g, and are easily resuspended by pipetting, making solution changes relatively simple.

PI chromosomes can be labelled with magnetic microparticles. PI stabilized L929 cell chromosomes were centrifuged onto EM grids and standard EMISH was performed with pSAT1 followed by labelling with magnetic particles, using the same procedure as described above. Preparations Were labelled with both micro- and nanoparticles.

This resulted in 100% labelling with nanoparticles and levels of labelling with microparticles comparable to Miller spread controls and negligible levels of nonspecific labelling. Stabilized chromosomes suitable for flow cytometry can therefore be labelled efficiently with both magnetic micro- and nanoparticles.

Figure 18A:
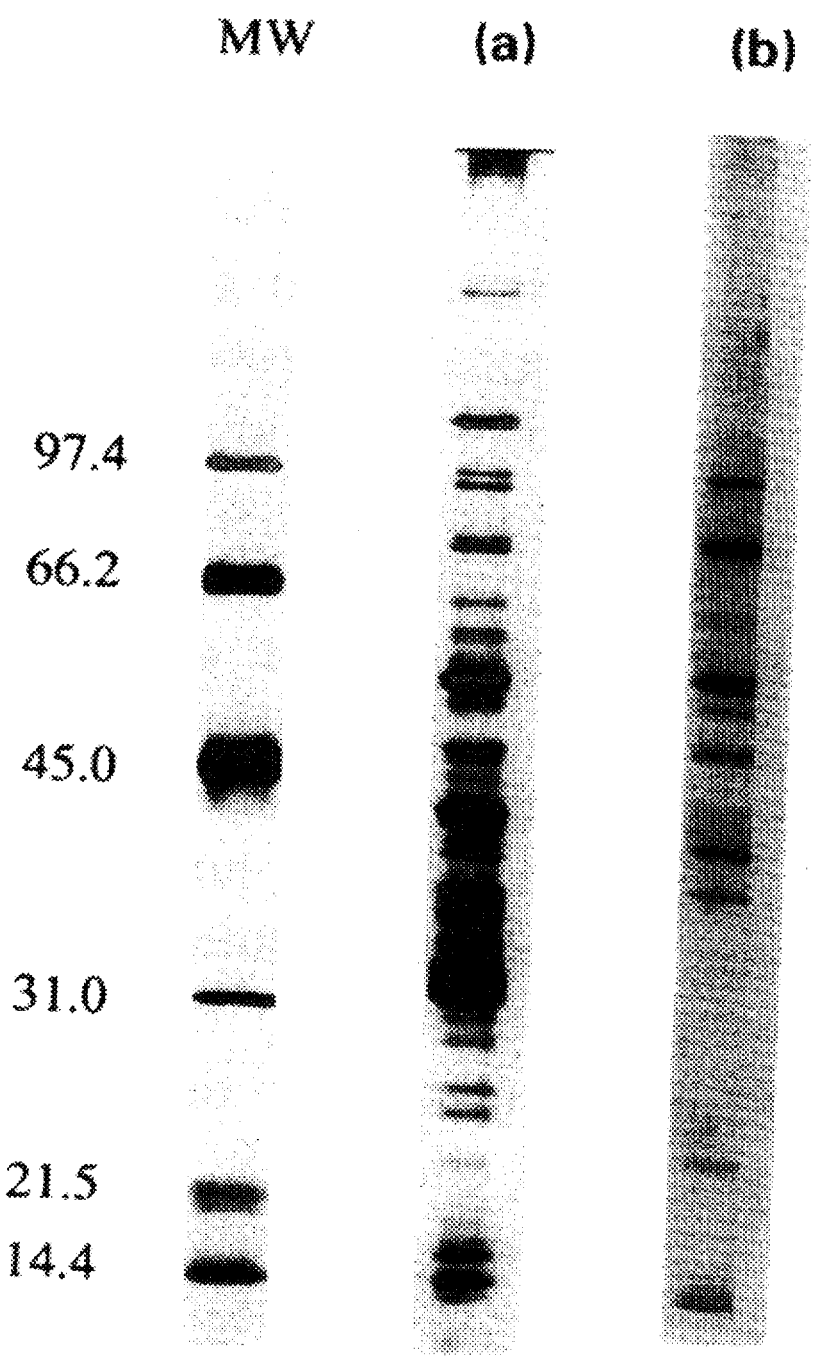
FIG. 18A illustrates a Western blot analysis of $\alpha$-OM to purified outer envelopes of pea chloroplasts. Lane A is total protein from outer envelopes of pea chloroplasts probed with $\alpha$-OM and Lane B indicates the presence of 5 strongly cross-reacting proteins.
Figure 18B:
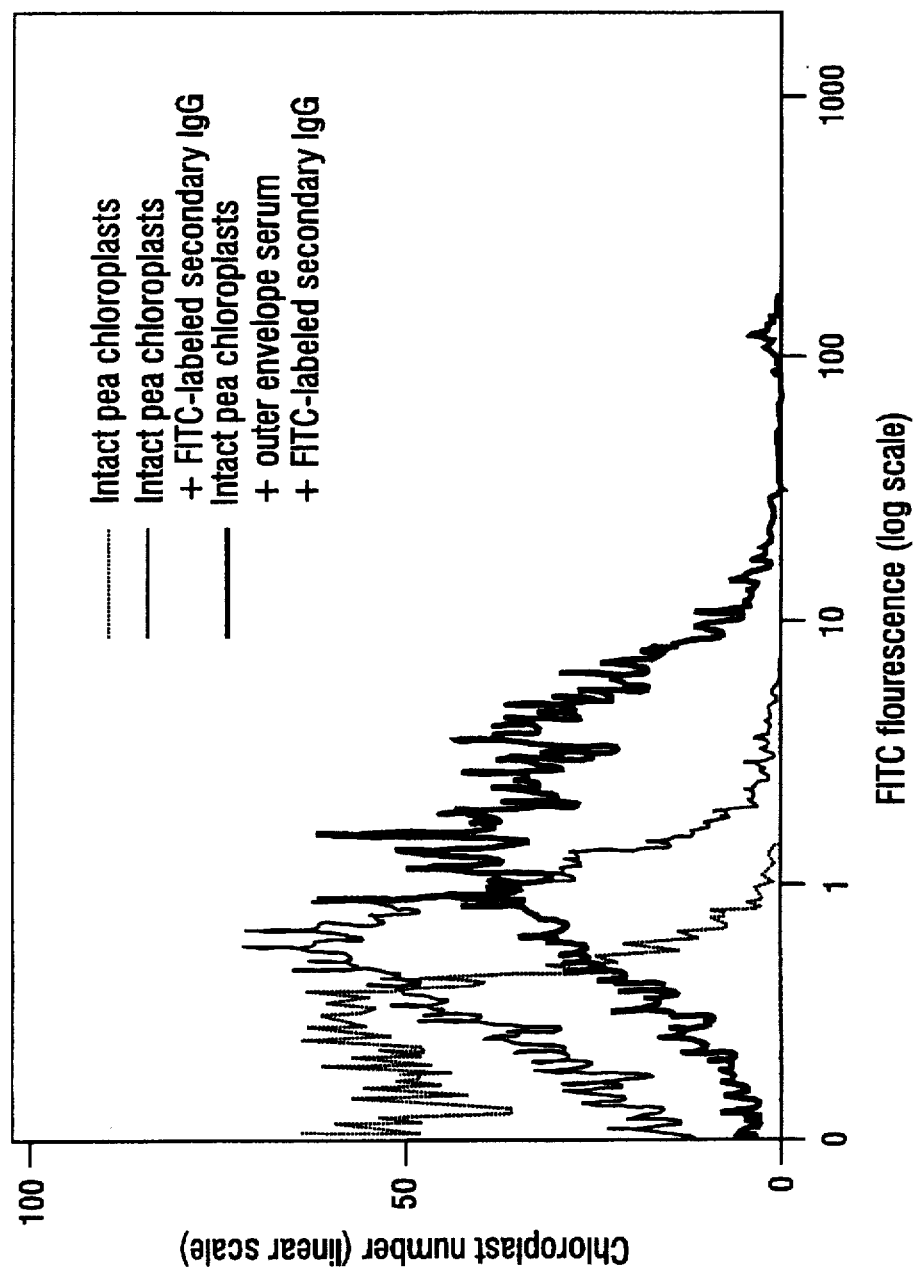
FIG. 18B illustrates a FACS analysis showing a shift in fluorescence of intact pea chloroplasts labelled with $\alpha$-OM and detected with a secondary FITC labelled IgG.

E. The α-OM Antisera Reacts with Extrinsic Epitopes on Chloroplast Outer Envelopes A polyclonal antibody (α-OM) has been prepared against isolated outer envelopes of mature green chloroplasts of pea (Keegstra and Yousif, 1986) and determined to recognize many epitopes of the chloroplast envelope. These antibodies cross react strongly with five different bands with molecular weights of 86 kD, 75 kD, 55 kD, 36 kD, and 14 kD on a Western blot of purified envelopes (FIG. 18A). Suspensions of sedimentation gradient prefractionated intact pea and maize chloroplasts were incubated in chloroplast immunolabelling buffer containing either preimmune serum, rabbit antihistone (α-RH) antisera, or the α-OM antisera. Under the conditions of this assay, only incubation with α-OM led to strong agglutination of the isolated chloroplasts. Both pea and maize chloroplasts appeared to be equally reactive. When prefractionated pea chloroplasts are labeled with α-OM and an FITC-labeled secondary IgG and analyzed with a fluorescence activated cell sorter (FACS) a significant shift occurs in FITC fluorescence compared with the control (FIG. 18B). By these observations it is concluded that the α-OM antisera is reacting with exposed epitopes on the cytosolic side of the outer chloroplast envelope.

Aliquots of the entire ammonium sulfate precipitated protein fraction of preimmune serum, and α-RH, or α-OM antisera containing total 1 gG were either coupled directly to various magnetic particle preparations or dialyzed against sodium bicarbonate and biotinylated- The functional activity of the protein coating on the magnetic preparations was assayed by incubation with serial dilutions of appropriate HRP-conjugated tracers detected by color substrate formation with OPD/peroxide. All of the various particle preparations are coated with functional proteins which are capable of binding their corresponding HRP-labeled tracers to a significant degree (Table 3). Both types of microbinding preparations are capable of binding approximately equivalent amounts of tracer for both the α-OM and the control α-RH. Therefore, it would be expected that their reactivity would be similar during immunolocalization experiments. As anticipated, the titer of streptavidin on all of the various particle preparations is very high. The nanoparticle streptavidin preparation contains a significantly higher titer of functional streptavidin compared to equal volumes of microparticle preparations, and this may be due to higher particle concentration and/or increased solid phase surface area.

TABLE 3

In vitro Starch Synthesis by Isolated Intact Amyloplasts

| Isolation Method | Source | Lysis | Total nmol/3 × 10⁷ Amyloplasts | Methanol Insoluble Products | |
|---|---|---|---|---|---|
| | | | | H₂O Insol. % Recovered | H₂O Sol % Recovered |
| ds | Endosperm | − | 89.8 | 73.7 | 26.3 |
| | | + | 10.8 | 78.4 | 21.6 |
| MIA | Endosperm | − | 80.6 | 77.1 | 22.9 |
| | | + | 8.7 | 79.1 | 20.9 |
| MIA* | Endosperm | − | 83.9 | 80.2 | 19.8 |
| | | + | 10.1 | 75.4 | 24.6 |
| ds | BMS susp. culture cells | 1 | 14.2 | 64.3 | 35.7 |
| | | + | 9.6 | 61.8 | 38.2 |
| MIA | BMS susp. culture cells | − | 12.7 | 65.9 | 34.1 |
| | | + | 7.9 | 57.4 | 42.6 |
| MIA* | BMS susp. culture cells | − | 16.4 | 67.2 | 32.8 |
| | | + | 8.3 | 60.9 | 39.1 |

*Incubation of [¹⁴c] ADP-Glc with magnetically adhered amyloplasts on the column.

F. Immunoabsorption of plastids to magnetic microparticles

The superparamagnetic polymer coated microparticles and the silane treated affinity chromatography Biomag preparations coupled to either preimmune serum, α-RH, or α-OM antisera were tested for their ability to specifically bind plastids. The various preparations were incubated with dilution series constructed from either prefractionated pea and maize chloroplasts or whole cell lysates prepared from protoplasts of pea and maize endosperm in isolation buffer plus 0.5% bovine serum albumin. These mixtures were incubated for intervals ranging from 5 min-3 hrs at 4 C. in the dark, and then precipitated at 10 min. intervals with a small neodymium-iron-boron disc magnet. A significant number of plastids (as indicated by chlorophyll measurements) were magnetically precipitated from all samples incubated with the polymer coated microparticles indicating nonspecific binding even during short incubation times. As a primary label for direct separation, only the silage treated biomag particles coupled to α-OM were capable of recovering specifically labelled organelles from samples incubated less than 15 min. However, only low numbers of plastids were recovered per sample even when the particles are present in excess. Longer incubations resulted in large numbers of immobilized plastids which were demonstrated to be highly magnetically responsive, however, similar numbers of plastids were observed bound to antihistone and preimmune controls. Chloroplasts which had been immobilized to magnetic microparticles were capable of being moved through several successive solution changes by magnetic precipitation and shown to be competent for the import of the in vitro synthesized precursor to the small subunit of ribulose 1,5-bisphosphate carboxylase. To determine if a biotin/streptavidin recognition system would either increase yield or reduce the apparent nonspecific reactivity, prefractionated chloroplast and amyloplast preparations were first incubated with a dilution series containing 0–500 μg of the various biotinylated antisera on ice for 10 min. in the dark. These primary labelled preparations were than reacted with 100 μl of either type of streptavidin conjugated magnetic microparticles for 5 min-3 hrs and separated on a neodymium-iron-boron disc magnet. The relative number of chloroplasts recovered was determined from chlorophyll content measurements. Compared to results using a primary antibody coupled directly to magnetic microparticles, these experiments showed that use of a secondary label did not increase the number of specially immunoabsorbed plastids or decrease the apparent background non specific reactivity.

Figure 19A:
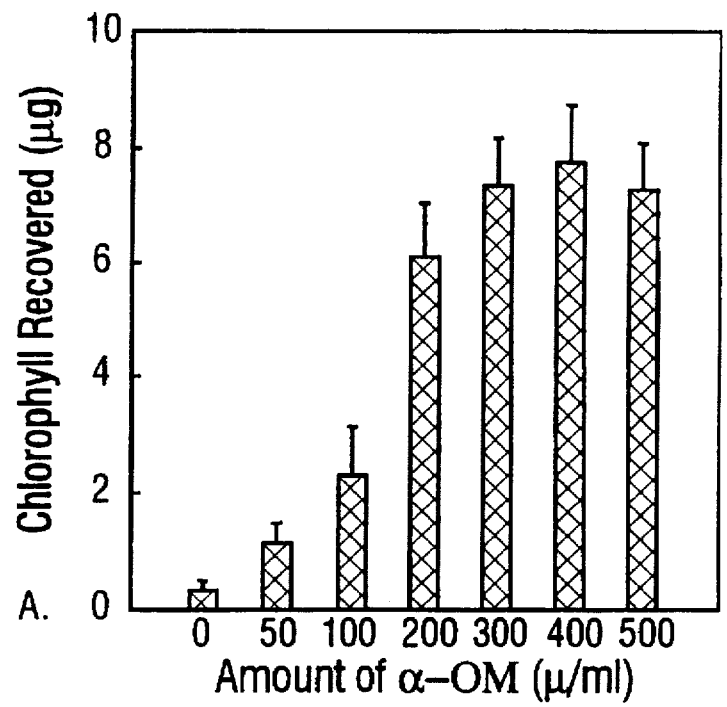
FIGS. 19A–C illustrate the parameters for immunoisolation of pea leaf chloroplasts. The open bars indicate no primary label. The right crosshatch indicates biotinylated PS. The left crosshatch indicates biotinylated $\alpha$-RH. The solid bars indicate biotinylated $\alpha$-OM.

Initially, to establish separation parameters for plastids immunolabelled with magnetic nanoparticles, the biotinylated antibody preparations were incubated with chloroplasts prefractionated by Percoll density sedimentation (Barlett et al., 1982). Chloroplasts samples were washed with ten times volume of isolation buffer, pelleted from the wash at 4550 g for 2 min., and resuspended in isolation buffer containing 2% nonfat milk, 20 mM KCl and 0.05 mg/ml preimmune serum to 500 μl aliquots with a chloroplast concentration containing 300 μg chlorophyll each. To establish a functional antibody concentration for immunolabelling, the chloroplast samples were incubated with a dilution series containing 0–500 μg of the biotinylated α-OM on ice for 10 min. in the dark. The labelled chloroplasts were then reacted for 5 min. with 100 μl of streptavidin conjugated magnetic nanoparticles (0.0025 mg/ml Fe₃O₄) and immediately separated with isolation buffer on a magnetic affinity column adjusted to a flow rate of 200 μl/min. at 4 C. in a high gradient magnetic field. After washing the column with approximately ten volumes of isolation buffer at a flow rate of 1.5 ml/min., the column was removed from the magnetic field and briefly passed through a 110 volt (A.C.) demagnetizer, backflushed with 1.0 mil isolation buffer, separated and washed again before the chloroplasts were eluted. The separated chloroplasts were finally eluted from the column matrix by gently backflushing with 1 ml cold isolation buffer after removal from the magnetic field and brief demagnetization. Background and depletion percentages were measured spectrophotometrically by chlorophyll recovered (FIG. 19A). At the flow rate used in these separations (200 µl/min.), trace amounts (0.33 µg) of chlorophyll were recovered from the column with samples containing no biotinylated antibody and increasing amounts of chlorophyll (up to 7.69 µg chlorophyll) were recovered from samples labelled with 400 µg of biotinylated α-OM. The present inventors could routinely recover $3 \times 10^7$ chloroplasts/ml using this separation procedure conducted in high gradient magnetic fields produced by either neodymium-iron-boron magnets or high field strength electromagnets rated to a field strength of greater than 7.0 kG or 0.6 Tesla.

Figure 19B:
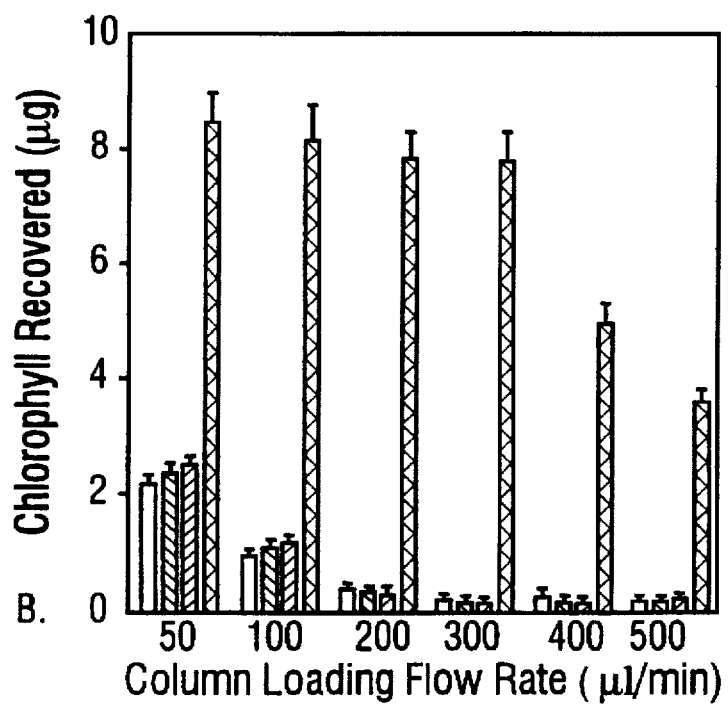

Nonspecific background reactivity was then determined by incubating magnetic streptavidin with unlabelled chloroplasts and chloroplasts labelled with biotinylated antihistone and preimmune serum, and adjusting the flow rate through the magnetic column to achieve the lowest amount of chlorophyll recovered (FIG. 19B). At flow rates through the column of less than 200 µl/min., significant numbers of chloroplasts (0.36–2.52 µg chlorophyll) were retained by physical lodging and nonspecific reactivity. The numbers of specifically labelled chloroplasts retained on the column decreased precipitously when flow rates were increased above 300 µl/min. For the columns used in these experiments, the most stringent conditions for chloroplast recovery without background attributable to physical lodging on the column, or low nonspecific antibody reactivity, proved to involve an initial loading flow rate of 300 µl/min. followed by a wash flow rate of 1.5 ml/min. Clumping of the plastids and retention on the columns was observed when high amounts (over 500 µg) of antisera was present during immunolabelling.

Figure 19C:
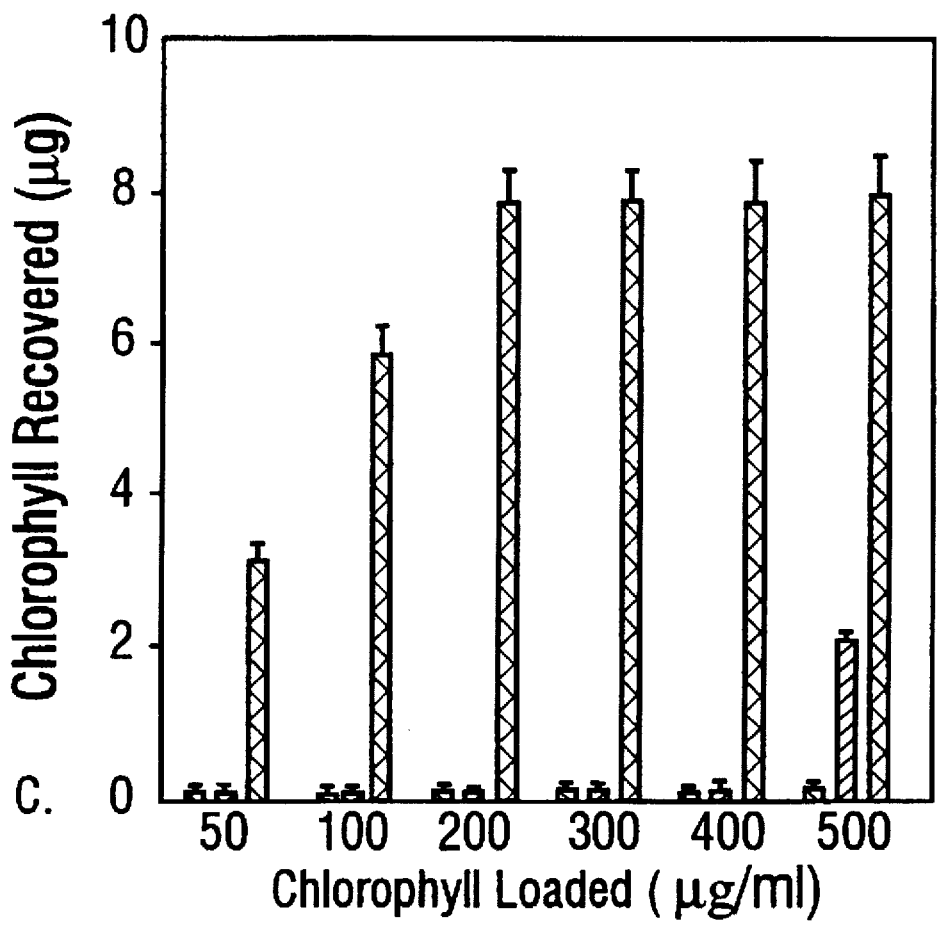

By using the parameters defined by the above studies, the recovery of labelled prefractionated pea chloroplasts from dilution series consisting of samples with increasing amounts chlorophyll was examined (FIG. 19C). Increasing the concentration of chloroplasts in the reaction results in increased recovery of labelled plastids until the system is apparently saturated. When a low concentration of primary labelled chloroplasts (50 µg chlorophyll) was incubated with a low number of streptavidine conjugated nanoparticles (10 µl) corresponding low but significant amounts of chlorophyll were recovered (1.96±0.19 µg). The labelled chloroplast samples reacted with various amounts of streptavidin conjugated magnetic nanoparticles show that increasing the amount of magnetic nanoparticles results in a corresponding increase in chlorophyll recovered. When higher amounts of magnetic nanoparticles (300 µl) are incubated in the presence of highly concentrated primary labelled samples (500 µg chlorophyll loaded), the recovery rate is significantly improved (up to 13.76±0.86 µg chlorophyll recovered) indicating that the excess of unreacted biotinylated proteins in the antibody preparation are competing for the magnetic particles and therefore reducing the efficient recognition by the immunoabsorbent of labelled organelles. By using specific affinity purified antibodies the yield of recovery should be dramatically increased.

The control samples reacted with biotinyiated preimmune or nonimmune antibodies define nonspecific binding. The level of recovery of nonspecifically labelled organelles can be adjusted to near zero by manipulating the flow through the column. Long incubations (>30 min.) with either primary or secondary label resulted in increased amounts of nonspecific binding. The antihistone and preimmune serum controls demonstrate the specificity of the isolation in samples reacted with α-OM above background (FIG. 19C) and define the necessary parameters for isolation experiments with whole cell lysates. Overall, the recovery of chloroplasts labelled with the α-OM antibody is shown to be specific but low, and this is attributed to low titer of the specific antibody binding to exposed epitopes.

Example 5

Preparation of Indicators

A. Magnetic microparticles

Superparamagnetic polymer coated (latex) microspheres, 0.74 µm, (Bangs Laboratories, Inc.) were covalently coupled to antisera preparations and streptavidin via carboxyl amino linkages. Affinity chromatography grade Biomag (Advanced Magnetics Corp.) magnetic microparticles were first density sedimented to recover particles that were less than 0.5 µm average diameter, then rinsed with acetone, and refluxed for 24 hrs. with N-(2-Aminoethyl)-3-aminopropyltriethoxysilane, providing an amino functional surface to which the antibody preparations were covalently coupled directly using glutaraldehyde (Pierce Chemical Co.). Covalent coupling of protein to either carboxylated or aminated microparticles was accomplished by slowly vortexing 1.0 ml of dilute purified antisera (1 mg/ml in MES buffer, pH 5.5) with 100 µl of colloidal microparticle suspension at room temperature for five minutes, before adding 0.1 ml CDI (1-ethyl-3-(3-dimethylaminopropyl)carbodiimide solution (Aldrich Chemical Co.) freshly prepared for 2 hours with 10 mg/ml in distilled water. Coupling proceeded for 2 hours with continuous gentle agitation at room temperature, before microparticles were precipitated from solution with a rare earth disc magnet, washed three times with a buffer containing 0.05M $NaH_2PO_4H_2O$, 0.1% NaCl and 0.2% gelatine and stored at 4 C. until used.

B. Magnetic nanoparticles

Magnetic nanoparticles were synthesized according to Molday and MacKenzie (1982) and consisted of ferric oxide crystals ($Fe_3O_4$) encapsulated by dextran. The crude particle preparation was filtered twice through 0.22 µm Millipore filters, activated by cyanogen bromide and subsequently coupled to the various antisera with diaminohexane according to the procedure by Miltenyi et al. (1990). Magnetic particles can also be purchased from Immunocon, Nitteryi Biotech and from other commercial sources.

C. Preparation of magnetic affinity columns

A typical magnetic affinity column used for these experiments consisted of 0.25 grams stainless steelwool (Formby's 00, average fiber diameter of 50 µm) which had been placed in a Pasture pipette, washed several times with ethanol to remove protective oil, coated with ultra low viscosity embedding medium, and cured overnight at 65 C. The columns were thantreated with Sigmacote (Sigma Chemicals, Inc.) and air dried, injected with 70% ethanol to thoroughly wet the surface, and rinsed with ten volumes of immunolabelling buffer to condition before loading.

Example 6

Flow cytometry of cellular components

A. chloroplasts and protoplasts

The flow cytometric analysis of various chloroplast and protoplast preparations involved the measurement of forward angle light scattered right angle light scatter and chlorophyll-a autofluorescence. Flow cytometry was conducted on a dual laser Becton Dickinson FACStar$^{Plus}$ flow cytometer. A Spectra Physics 5 Watt Argon ion laser (50 mWs of the 488 nm line) was used to measure the forward and right angle light scatter and to excite the chlorophyll-a autofluorescence. Fluorescence was resolved spectrally with the 670/ nm band pass filter. With the exception of forward scatter, all signals were collected with logarithmic amplifiers with no compensation and PMT voltage of 500 volts. Chloroplasts were in an isotonic buffer and were analyzed at the rate of 2500–4000/sec using sterile phosphate buffered saline as the sheath buffer. For each sample 10,000 particles were analyzed and acquired in list mode without gating. The forward angle light scatter signal was used for the triggering signal.

B. Chromosome purification by reversible immobilization, FITC labelling, and FACS Preliminary fluorescent labelling of L929 cell chromosomes hybridized with pSAT1, and labelled on alginate/PEI coated supports was performed. Postfixation of hybridized chromosomes was followed by labelling with rabbit-anti-biotin AB, biotinylated goat-anti-rabbit AB, and FITC-conjugated streptavidin for 30 mins each. Control samples were taken through the same procedure, but in the absence of probe. The optical clarity of alginate allowed rapid examination of preparations in the fluorescence microscope as for typical in situ hybridizations.

For FACS analysis, hybridized chromosomes were detached from the alginate pad after FITC labeling and propidium iodide and FITC fluorescence quantitated in a Becton-Dickinson FACSstar Plus. Unlabelled chromosomes were treated in the same way, as were mixtures of the two. Fluorescence microscopy demonstrates that L929 cell chromosomes are specifically labelled at their centromeres after hybridization with pSAT1 and labelling with FITC-streptavidin. Controls are unlabelled.

The FACS profile shOWs that FITC labelled chromosomes can be clearly distinguished form unlabelled chromosomes, both separately and in mixtures of the two. Fluorescence in situ hybridization can be successfully combined with reversible immobilization to produce labelled chromosomes that are analyzable by the FACS machine.

Example 7

Characterization of Cellular Components After Isolation

A. Characterization of the DNA obtained by magnetic isolation of mouse chromosomes Immunomagnetic purification of chromosomes is less useful if, in the process, DNA is damaged and rendered useless for subsequent procedures. Purified chromosomal DNA therefore characterized in terms of its molecular weight, sequence enrichment, strandedness, digestibility with restriction enzymes, and suitability for cloning.

Relative sequence enrichment of a sorted chromosome preparation is determined by slot blotting and hybridization with an appropriate probe. DNA from magnetically sorted chromosomes is purified by a combination of proteinase K digestion, to remove the iron tag, and standard phenol extraction to remove extraneous protein. Similar amounts of total mouse and pure Y DNA is slot blotted and hybridized with YB10. If purification is successful, the Y sample should show more hybridization at a given amount of DNA. Scanning the blots permits measurement of the relative degree of enrichment.

One of the methods relies on probe hybridization, and hence denaturation and renaturation of the target DNA regardless of whether antibodies or direct labelling are used. It is therefore conceivable that the DNA might be more disrupted than in FACS, where denaturation of the chromosomes does not occur. Hence, it is important to demonstrate that purified DNA is sufficiently intact for restriction enzyme digestion and cloning. Evidence from EMISH (Narayanswami, unpublished) suggests that chromosomal DNA renatures quickly during probe hybridization: denatured preparations stored for more than a few hours before addition of probe no longer show hybrid formation. Furthermore, primers hybridize efficiently to denatured chromosomal DNA during the PRINS procedure (Koch et al., 1989), showing that denatured chromosomes can renature rapidly. Finally, the denaturation/hybridization method employed in the sorting procedure is relatively gentle compared to the methods normally used for EMISE and should allow considerable renaturation of the chromosome (Stuart et al., 1978). The degree of double-strandedness is determined by digestion with single-strand specific nucleases and comparison with control DNA samples. The mean molecular weight of the DNA is assayed by standard gel electrophoresis.

Digestion of high molecular weight DNA with restriction enzymes results in a smear, representing a continuous size distribution of DNA fragments. Although the appearance of a smear on incubation of purified DNA with a restriction enzyme argues that the DNA was digested, the appearance of specific fragments is a better demonstration. For the Y this can be accomplished by digestion with EcoR1, gel electrophoresis of the DNA and blotting, followed by hybridization with pCRY8/B, which detects a 2.2 Kb Y-specific fragment within the Sxr region (Eicher et al., 1991). This fragment is sufficiently large that its presence argues against degradation of the DNA.

Whether purified DNA can be cloned is easily determined. The purified DNA is digested with several restriction endonucleases and ligated into the 2.9 kb multipurpose vector pBluescript II, followed by transformation of *E. coli* and growth by standard methods (Maniatis et al., 1982). The resulting clones are tested by restriction enzyme digestion for the presence of inserts, and by FISH for the presence of mouse DNA.

A YAC library can be constructed from purified mouse Y chromosomes. Whether immunomagnetically purified DNA is capable of being maintained in these vectors is determined by the rapid YAC library construction method of Strauss (Strauss et al., 1992), followed by probing with an already characterized sequence. These libraries are constructed and screened for Y-linked sequences. They constitute the first examples of the use of a new, inexpensive, and transferable technology that should significantly add to current efforts in the physical mapping of the mouse genome.

B. Recovery of high molecular weight DNA from alginate-immobilized chromosomes labelled with magnetic particles In a preliminary experiment, it was determined whether denaturation and probe hybridization, the steps where most damage occurs to the DNA, resulted in degradation. PI stabilized chromosomes were fixed, denatured, and hybridized with probe. DNA was extracted from the chromosomes and gel electrophoresis performed under standard conditions. Total mouse genomic DNA and DNA from unhybridized PI stabilized chromosomes were run as controls.

Metaphase chromosomes from L929 cells were then immobilized and labelled with magnetic particles as described above. Chromosomes were detached after labelling and the DNA extracted. In evaluating the quality of DNA from alginate purified chromosomes, a major concern is the removal of probe, antibodies, and magnetic particles from the DNA. The preparative method that is used is a standard one for preparing high molecular weight DNA but with the addition of an incubation in EDTA/DTT to remove residual alginate from the chromosomes. Proteinase K digestion is then employed to remove chromosomal proteins, antibodies and magnetic particles, followed by standard phenol extraction of the DNA. Residual magnetic particles can be easily removed from the DNA either by mild centrifugation or permanent rare-earth magnet. It is contemplated that the presence of hybridized probe is not a problem and hence it is not removed.

No significant difference was observed in the molecular weight profiles of total mouse DNA, unhybridized chromosomes. In all cases, the DNA was high molecular weight. DNA extracted from alginate labelled chromosomes is also high molecular weight. Although this result tells us that the DNA is large, it does not tell us whether the DNA is clonable as YAC-sized fragments. The mobility of the DNA must be examined under pulsed field conditions.

About 1 μg of DNA was obtained from 1 million mitotic cells. The chromosomes from these cells were immobilized on 6 1 cm coverslips. This yield could easily be improved by using a greater amount of starting material and larger immobilization matrices, for instance, Petri dish sized substrates. Scaling up of the procedure is in principle relatively easy. Furthermore, the DNA from several experiments could be pooled before cloning.

C. Metphase chromosome preparation for EM in situ hybridization

The standard methods for metaphase chromosome preparation and EM in situ hybridization are used for immunomagnetic labelling of both Miller spread and PI stabilized metaphase chromosomes.

Metaphase chromosomes for EM in situ hybridization were obtained by arresting L929 cells with 0.15 μg/ml Colcemid (Gibco) for 6 h at 37 C. Mitotic cells were collected by selective detachment. Cells were lysed in 0.5% Nonidet P40 and released chromosomes were deposited on EM grids by a modification of the Miller procedure as described in Rattner et al., 1978. Chromosomes were centrifuged through a 1M sucrose cushion in a microcentrifugation chamber onto an EM grid. After brief centrifugation (5 min at max speed in a Sorvall GLC2B benchtop centrifuge) grids were removed, rinsed in Kodak Photoflo and air dried.

D. Physiological integrity of magnetically isolated plastids

Figure 21B:
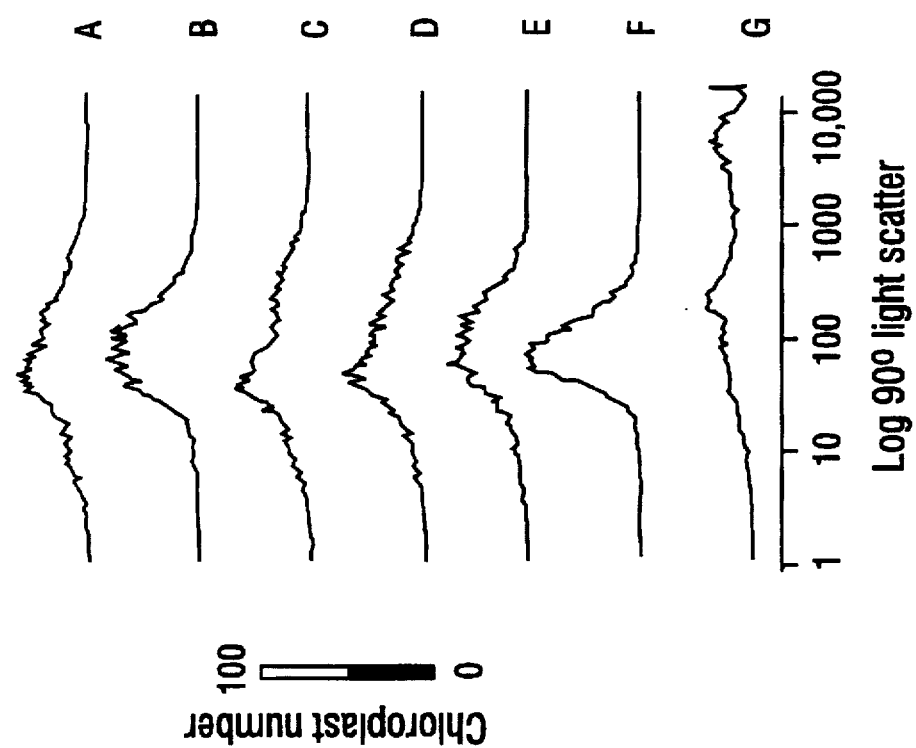
FIG. 21 illustrates a flow cytometric analysis of various chloroplast and protoplast preparations by measurement of forward angle light scatter, right angle light scatter and chlorophyll a autofluorescence. Sample A is a crude pea leaf homogenate prior to fractionation. Sample B is pea chloroplasts (intact) from Percoll gradient fractionation. Sample C is pea chloroplasts (broken) from Percoll gradient fractionation. Sample D is intact Percoll gradient fractionated pea chloroplasts which have been broken by a combination of hypotonic lysis and physical shearing through #25 gauge needle. Sample E is maize chloroplasts isolated by magnetic immunoabsorption with nanoparticles from whole cell lysate of ruptured leaf protoplasts. Sample F is pea chloroplast isolated by magnetic immunoabsorption with nanoparticles from whole cell lysate of ruptured leaf protoplasts. Sample G is isolated intact pea leaf protoplasts.
Figure 21A:
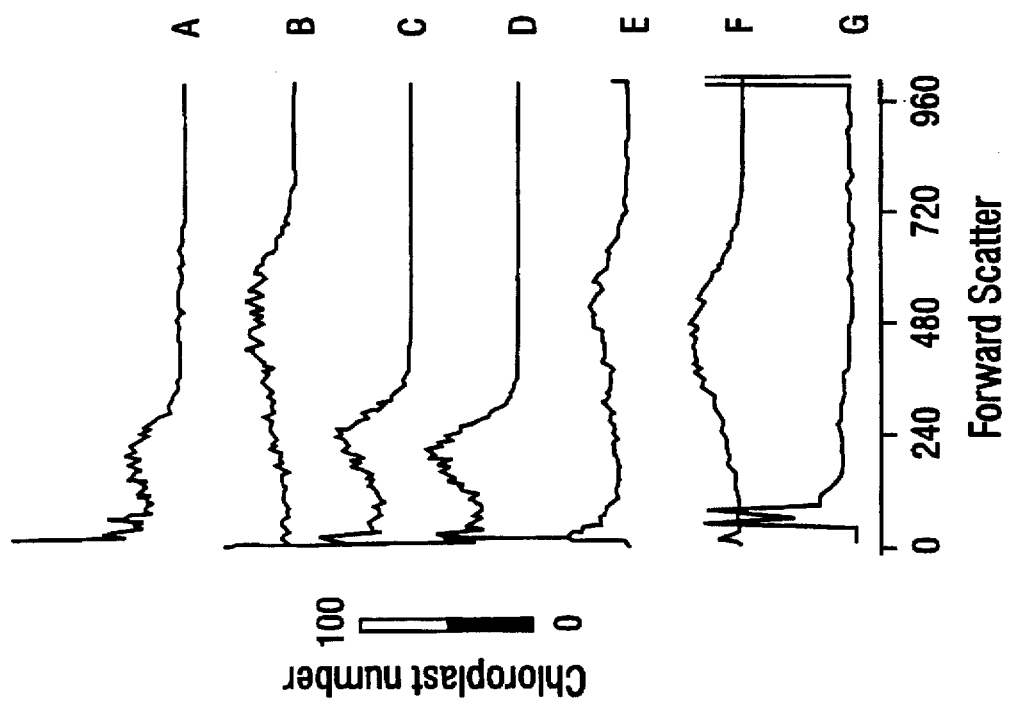
Figure 21C:
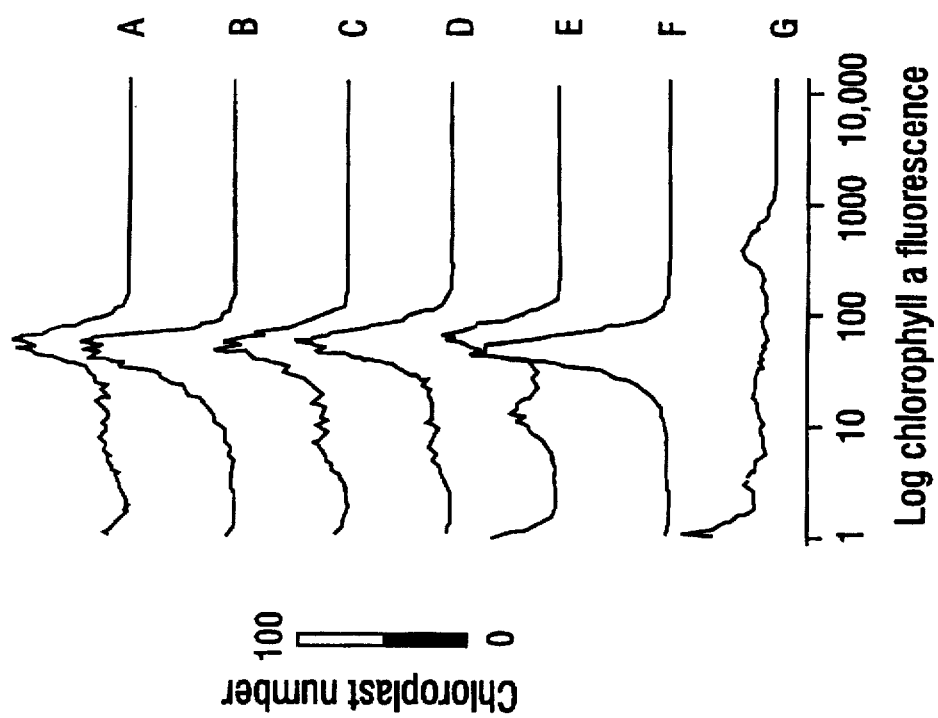

The degree of intactness of plastids isolated by magnetic immunoadsorption was examined by several different approaches. The integrity of chloroplasts isolated from pea and maize was determined by light scattering qualities and chlorophyll a autofluorescence with a flow cytometer. The fluorescence activated cell sort (FACS) is capable of quickly demonstrating the relative integrity of a large number of chloroplasts (FIG. 21). Compared with chloroplasts isolated from Percoll gradients, both maize and pea chloroplasts isolated from lysed protoplasts by magnetic immunoadsorption show a high degree of integrity. It is also possible to distinguish both populations of maize bundle sheath and mesophyll chloroplasts on the basis of their chlorophyll-a fluorgreence. Mesophyll chloroplasts have a much greater amount of photosystem II containing grana thylakoids which accounts for the 10 fold higher level of chlorophyll a fluorescence (FIG. 21E). Broken plastids become much less scattering and are represented by a signal less than channel 350 as shown in FIG. 21C and D. The chlorophyll-a fluorescence signal for magnetically isolated chloroplasts has the lowest coefficient of variation indicating a high degree of homogeneity.

Figure 22A:
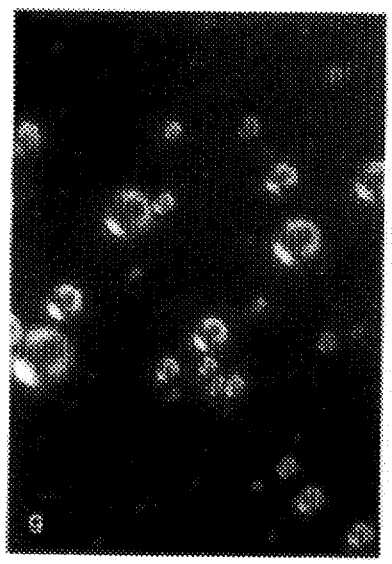
FIG. 22A illustrates phase contrast microscopy of amyloplast isolations prepared by conventional 1 g sedimentation.
Figure 22B:
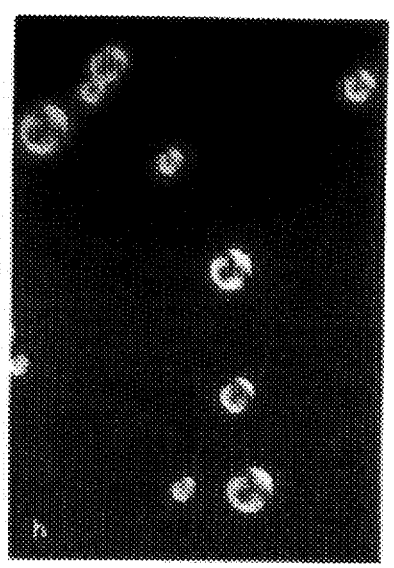
FIG. 22B illustrates phase contrast microscopy of amyloplast isolations prepared by magnetic immunoabsorption with steptavidin nanoparticles.
Figure 23C:
FIG. 23C is in organellar protein synthesis by pea chloroplasts isolated by magnetic immunoabsorption from whole cell lysate of ruptured protoplasts.
Figure 23D:
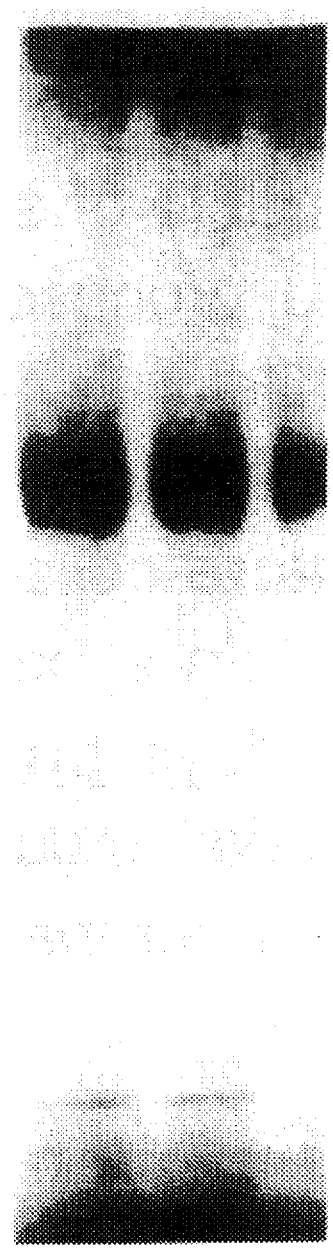
FIG. 23D is in organellar protein synthesis by maize (BMS) amyloplasts isolated by magnetic immunoabsorption from whole cell lysate of ruptured protoplasts of suspension culture cells.

As might be expected, the process of magnetic immunoadsorption does not strongly distinguish between intact versus ruptured organelles. Therefore, the degree of integrity is dependent to a large extent on the method used for cell disruption. The most intact plastids were recovered from lysed protoplast preparations made by an osmotic shock treatment followed by passing the cells through a 37 μm mesh nylon screen. Disadvantages to using protoplasts as starting material are that a truly representative population of cells may not be recovered from heterogeneous tissues, and that the process of protoplasting may alter the metabolism of the cell prior to organelle isolation. The integrity of amyloplasts isolated from chopped maize endosperm tissue was observed to over 95% (data not shown) by FITC-cationized ferritin staining of the plastid envelope. Light microscopy shows a difference between amyloplast preparations by conventional density sedimentation compared to those isolated by magnetic immunoabsorption (FIG. 22A–B). The physiological integrity of amyloplasts in these preparation was measured by their capacity for uptake and incorporation of [$^{14}$C] ADP-glucose to starch (Table 4). These assays could be conducted on magnetically absorbed maize amyloplasts which had been eluted and removed from the column or directly while still adhered on the magnetic affinity column. Amyloplasts from maize endosperm were observed to incorporate a high level of label as starch insoluble fraction) compared to the activity of amyloplasts isolated from maize suspension culture cells. These results show that the magnetically labelled organelles were physically and physiologically intact, and that biochemical assays can be run directly on the columns. It is noted that the activity of density sedimented amyloplasts was slightly higher than those isolated by magnetic immunoabsorption and this may reflect damage to the amyloplasts while loading the magnetic affinity column which requires one additional pipetting step compared to the density sedimented preparation. This observation further underscores the fragility of the amyloplast. Assays were then conducted to determine whether isolation of plastids in a magnetic field disrupts their ability to undergo in organellar protein synthesis (FIG. 23). In organellar protein synthesis was observed in both prefractionated (intact) pea and maize chloroplasts as well as pea chloroplasts and maize cell suspension amyloplasts separated by magnetic immunoabsorption. In those preparations, protein synthesis was not inhibited by cycloheximide, but was greatly reduced by chloramphenicol, indicating intactness and separation from contaminating cytoplasm. Physiological intactness was also indicated by their ability to uptake and process nuclear encoded protein precursors. Both maize and pea chloroplasts isolated by magnetic immunoabsorption are capable of synthesizing their own proteins and importing and processing in vitro synthesized precursor proteins. While in organellar protein synthesis was demonstrated by amyloplasts isolated from maize suspension culture cells, substantial amounts of protein synthesis were not observed in amyloplasts from maize endosperm 13 days post-pollination, even though the ADP-glucose uptake studies demonstrate that these latter plastids were physiologically intact.

TABLE 4

Evaluation of Activity of Functional Coating on Magnetic Preparations

| HRP CONJUGATE DILUTION FACTOR | SA | | α-RH | | | α-OM | |
|---|---|---|---|---|---|---|---|
| | PC | BM | M | PC | BM | PC | BM |
| 1:500 | >2.00 | >2.00 | >2.00 | >2.00 | >2.00 | >2.00 | >2.00 |
| 1:1,000 | >2.00 | >2.00 | >2.00 | >2.00 | >2.00 | >2.00 | >2.00 |
| 1:2,000 | >2.00 | >2.00 | >2.00 | >2.00 | >2.00 | >2.00 | >2.00 |
| 1:4,000 | >2.00 | >2.00 | >2.00 | 1.977 | 1.841 | 1.688 | 1.724 |
| 1:8,000 | >2.00 | >2.00 | >2.00 | 1.407 | 1.431 | 1.256 | 1.332 |
| 1:16,000 | >2.00 | >2.00 | >2.00 | 0.962 | 1.018 | 0.727 | 0.824 |
| 1:32,000 | >2.00 | 1.552 | >2.00 | 0.698 | 0.732 | 0.532 | 0.679 |
| 1:128,000 | 1.297 | 0.983 | >2.00 | 0.370 | 0.397 | 0.351 | 0.356 |
| 1:256,000 | 0.743 | 0.721 | 1.876 | 0.248 | 0.281 | 0.296 | 0.251 |
| 1:512,000 | 0.445 | 0.391 | 1.426 | 0.258 | 0.276 | 0.270 | 0.260 |
| 1:1,024,000 | 0.334 | 0.267 | 0.915 | 0.251 | 0.270 | 0.250 | 0.259 |

E. Assays to determine plastid integrity

In organellar protein synthesis assays were performed according to the method of Ellis (1982); uptake and incorporation of $^{14}$C-ADP-Glucose by isolated amyloplasts was observed by the method developed by Liu et al. (1991); FITC-cationized ferritin labelling for fluorescent determination of amyloplast membrane integrity was by the method of Sack et al. (1983); and in vitro synthesized precursor import assays were according to Bartlett et al. (1982).

F. EM in situ hybridization

Chromosome preparations on EM grids Were fixed in 0.1% glutaraldehyde,2×SSC, denatured for 10 min in pH12 2×SSC and hybridized at 30 C. overnight with 4 µg/ml denatured biotinylated probe DNA in a buffer containing 50% formamide, 10% dextran sulfate. After rinsing the preparations three times in 2×SSC at room temperature, hybrid sites were detected via incubation with appropriate antibodies in PBS/0.5M NaCl/2 mg/ml BSA at 37 C. followed by rinsing with PBS/NaCl at room temperature. The standard detection scheme for immunomagnetic labelling consisted of serial incubation with rabbit-anti-biotin antibody, biotinylated goat-anti-rabbit antibody, and streptavidin. Preparations were then labelled with biotin conjugated magnetic particles in PBS. They were rinsed in Photoflo, air dried, and examined in a JEOL 100C at 100 KV.

G. Light and electron microscopy

Light micrographs of isolated plastids were taken on samples in isolation buffer immediately after isolation with a Zeiss Axiophot using phase contrast and differential interference contrast microscopy. Transmission electron microscopy was done on isolated chloroplast samples fixed and processed according to (Bruce, 1991).

H. Analysis of activity of functional coating on magnetic particle preparations

To evaluate the activity of functional coating on the various protein coupled magnetic particle preparations, HRP-labeled tracers were detected and measure calorimetrically. A stock solution of Biotin hydrazide-HRP conjugate (0.65 mg biotin/ml) was serially diluted 1:500, 1:1,000, 1:4,000, 1:8,000, 1:16,000, 1:32,000, 1:64,000, 1:128,000, 1:256,000, 1:512,000 and 1,:1,024,000 in Dilutabody HRP conjugate diluent (Alerchek, Inc.). Stock solutions of cappel sourced affinity purified goat anti-rabbit (1.16 mg.ml protein) and goat anti-chicken (1.12 mg.ml) IgG's were serially diluted in the same fashion. Aliquots of 10 µl each of magnetic particle preparations were dispersed into glass tubes and washed four times, 1 ml/wash, with Standard immunoassay wash buffer (Alerchek, Inc.) particle preparations were centrifuged between wash steps to avoid any loss of material. After the last decanted wash, 100 µl of each dilution of biotin-HRP was added to the streptavidin coupled particles; similarly, 100 µl of each dilution of HRP-conjugated goat anti-rabbit IgG and HRP-conjugated goat ant-chicken IgG were added to the appropriate particle preparations. All tubes were incubated for 30 min. at room temperature and washed four times as before. After the last decanted wash 200 µl of OPD/peroxide color forming substrate was added, incubated for 15 min. at room temperature and stopped by addition of 200 µl 1N sulfuric acid. The mixture was separated magnetically and 200 µl of each aliquot was transferred to a microwell reader and measured at 492 nm.

Example 8

General Methods

A. In-Situ Hybridization

The hybridization buffer was prepared according to Narayanswami et al. (1989). The desired probe (e.g., biotinylated mouse satellite DNA) was added to 4 µg/ml and the mixture was heated for about 5 min. at 100° C., e.g., in a boiling water bath to denature the probe. The mixture was fast cooled on ice for about 2 min. and centrifuged briefly in a microcentrifuge to bring down any condensed buffer on the sides of the tube. The centrifuged buffer was kept on ice until needed. 50 ul buffer per coverslip was prepared.

The coverslips were fixed in freshly prepared 0.1% glutaraldehyde (EM grade, Polysciences) in 2×SSC for 20 min. at room temperature. The coverslip was covered with a few drops of 0–1% glutaraldehyde, 2×SSC, and then placed in a Petri dish. The coverslips were then rinsed briefly in 2×SSC.

Coverslips were denatured for 10 min. in 2×SSC at pH12 (about 12 drops of 10M NaOH in 50 ml of 2×SSC), rinsed in Photoflo, and placed on a clean glass slide. 50 ul of the hybridization buffer containing the denatured probe was quickly pipetted onto each coverslip. The coverslips were transferred to a wet box (a box containing moist paper towels, and having a lid) and hybridized at 30° C. overnight (12–15 h).

The coverslips were placed in a rack in a beaker. The coverslips were rinsed three times, for about 20 min. each at room temperature in 2×SSC (using about a 100 ml volume) to remove unhybridized probe.

B. Hybrid Detection

All of the following antibody incubations were performed in a physiological buffer, e.g., PBS, 0.5M NaCl, 2 mg/ml BSA (bovine serum albumin) from BRL for 2 h. at 37° C., in Petri dishes, in a wet box, unless otherwise stated. Incubations with Streptavidin were performed at room temperature, but otherwise as stated above.

For labelling with biotinylated ferric oxide particles, the coverslips were incubated successively in 1/500 rabbit-anti-biotin, followed by 1/500 biotinylated goat-anti-rabbit antibody, and then in 2 ug/ml Streptavidin (Bethesda Research Laboratories). After each incubation, in order to remove any unbound antibody, the coverslips were rinsed 3 times, for about 10 min. each, at room temperature, in PBS, 0.5M NaCl, in racks in a beaker (each rinse using about 100 mls vol).

For labelling with colloidal gold alone, preparations were first incubated in 1/500 rabbit-anti-biotin for 4 h at 37° C., and rinsed. This procedure was followed by overnight incubation in 1/7 goat-anti-rabbit-20 nm colloidal gold. Coverslips were rinsed 3 times for about 20 min. each in 1% BSA buffer (1% BSA, Fraction V, Sigma, 0.9% NaCl, 0.02M sodium azide, 20 mM Tris at pH 8.2) and chromosomes were detached.

If preparations were to be labelled with both colloidal gold and ferric oxide, overnight labelling in Streptavidin 20 nm gold was substituted for the Streptavidin incubation. Coverslips were then washed in 1% BSA as above, followed by labelling in ferric oxide. Chromosomes were then detached as described above.

C. Labelling with Ferric Oxide Particles

Biotinylated ferric oxide particles of a mean diameter of about 50 nm to 2 microns prepared by inverting about 10 mls of buffered suspension 48 h before it was needed and allowing the preparation to settle out at 4° C. The top 2 ml of the suspension were used for labelling. This layer was removed with a Pipetman.

The ferric oxide was diluted two fold in PBS just before use.

Each coverslip was placed in 1 ml of the ferric oxide suspension in the well of a cell culture plate (Falcon) or a 24-well multiwell tissue culture plate with a lid (#3047 Becton-Dickinson). The plate was covered with its lid.

A small round magnet was placed underneath the well such that the ferric oxide particles covered the coverslip evenly. The rationale was to force the magnetic beads to bind the streptavidin on the chromosome by using the magnet to keep these 2 components in forced contact. The magnet was left in place, and the coverslip was kept at room temperature overnight.

The magnet was removed from underneath the well and placed on the lid of the plate, over the well containing the coverslip. The unbound ferric oxide will come off the preparation, and when the plate has been opened, can be removed the supernatant over the coverslip with a pipette and discarded. The ferric oxide was replaced in the well with 1–2 ml PBS, the coverslip was removed, and rinsed in racks in a beaker (as described above) 3 times, for about 20 min. each, in PBS, at room temperature.

D. Detachment of Chromosomes from Support

The Coverslips were incubated for 2.5 h in 50 mM dithiothreitol (DTT) in 2×SCC, at room temperature, in a Petri dish. Preferably, a few drops of DTT were placed on the coverslip.

Pipetting vigorously with a Pasteur pipette was used to dislodge the chromosomes from the support. The supernatant containing the related chromosomes was removed. Detachment can be monitored under a 40×ocular using phase contrast microscopy. For electron microscope (EM) observation, the chromosomes may be Centrifuged through 1M sucrose, onto grids, as described in Rattner and Hamkalo (1978).

E. Mechanism of ISPDP Reaction Using Chromosomes as the Biological Material

1. Primary amines on controlled pore glass LCAA are converted to active sulfhydryls.

CPG-LCAA $\xrightarrow{\text{50 mM Traut's Reagent}}$ CPG-LCAA-SH

2. Primary fixation achieves coupling of the reversible cross linker (SPDP) to the CPG-LCAA-SH.

The SPDP reaction binds the chromosome with a limited number of cross linkers, which can be easily cleaved by low concentrations of DTT, hence chromosome recovery is higher, and chromosome integrity is retained.

F. DTTSP Reaction Using Chromosomes as the Biological Material

1. Silanation of cover glasses
   a. Rinse with 1M HCl
   b. Rinse with distilled $H_2O$—about three times
   c. Rinse with dry acetone—about three times
   d. Reflux about 2 hrs—overnight with Pierce #80379 N-(2-Aminoethyl)-3-aminopropyltrimethoxysilane; this is prepared to 25% (v/v) in dry acetone
   e. Rinse with dry acetone—about three times
   f. For quality assurance detect presence of free amines may be detected with 1% fluoraldehyde [this is O-Phthaladehyde—Pierce Chemical Co. #26015] in distilled water and read in a fluorometer.

2. Free amines are provided to glass (and $Fe_3O_4$ particles) as diagrammatically represented in FIG. 1.

G. Labelling of metaphase chromosomes with submicron magnetic particles

The magnetic beads (Dynabeads) used by Dudin and coworkers to label chromosomes (Dudin et al., 1988) are relatively with, with a mean size of 4 um. The particles used in this invention consist of two types of magnetic particle with distinct magnetic properties, surface characteristics, and mean diameter size ranges. They have unique applications in the isolation of biological structures. The first type consists of a suspension of ferric oxide microparticles less than 0.5 microns in average diameter. The second type consists of ferric oxide crystals encapsulated by dextran (Molday particles, Molday et al., 1982). These "nanoparticles" are 30–60 nanometers in diameter and stable in the form of a colloidal suspension. The microparticles have a relatively large magnetic moment and are easily separated with a simple hand-held rare-earth magnet. Nanoparticles, on the other hand, have a smaller magnetic moment due to smaller size. Their smallness renders them particularly suitable for subcellular isolations by virtue of their high reactivity and specificity. However, they migrate less quickly than microparticles in conventional ferromagnetic fields so that structures labelled with nanoparticles must be separated in a magnetic affinity column (Molday et al., 1982).

These particles have two major advantages over DYNA-BEADS. First, they are much smaller, so that effects due to steric hindrance are minimized. This permits greater accessibility to targets, increased sensitivity of detection, and in consequence, larger yields of labelled material. Second, their unique surface chemistry contributes substantially to their usefulness as magnetic tags since been specific binding and aggregation are minimized. They have been successfully used as TEM and SEM markers for whole cells (Molday et al., 1982).

Magnetic particles can be derivatized in several ways, for instance by activation with cyanogen bromide followed by coupling of protein with diaminohexane, or silanation followed by glutaraldehyde coupling of protein. The particles used in these studies were covalently conjugated with either biotin or streptavidin. Studies were then performed to determine whether submicron magnetic particles could be used to label chromosomes specifically.

The mouse L929 cell chromosome system was used to perform studies in protocol development because large quantities of metaphase chromosomes can be easily obtained from this cell line by mitotic arrest with Colcemid. The mouse major satellite DNA clone pSAT1 (Radic et al., 1987) was used as a hybridization probe to determine the effectiveness of labelling protocols, since all the mouse centromeres except that of the Y label heavily with this probe (Pardue et al., 1987).

Chromosomes from the *Xenopus laevis* cell line XTC (Narayanswami et al., 1990), which contains both a large and a small NOR chromosome, were used to assess specificity of labelling under conditions where only 1–2 of the chromosomes should be labelled, rather than the entire karyotype. The *X. laevis* 18S+28S ribosomal RNA repeat clone pXlr101 (Trendelenburg et al., 1978) was used as a hybridization probe.

REFERENCES

Albert, B., Bray, D., Lewis, J., Raff, M., Roberts, K., Watson, J. D. (1989) Chap. 9, The Cell Nucleus, Mol. Cell. Biol., Garland Publishing Inc. (New York).

Anderson, L. and Mosbach, K. (1977) Magnetic Ferrofluids for Preparation of Magnetic Polymers and Their Application in Affinity Chromatography. Nature, 270:259.

Atten, J. A., Buyes, C.H.C.M., van der Veen, A. Y., Mesa, J. R., Yu, L. C., Gray, J. W., Osinga, J., Stap, J. (1987) Stabilization of chromosomes by DNA intercalators for flow karyotyping and identification by banding of isolated chromosomes. Histochecm. 87:359–366.

Bartholdi, M., Meyne, J., Albright, K., Luedemann, M., Campbell, E., Chritton, D., Deaven, L. L., Cram, L. S. (1987) Chromosome sorting by flow cytometry. Meths. Enzymol. 151:252–267.

Bebee, R., Gebeyehu, G. (1990) DNA capture reagent: A novel reagent for the rapid isolation of DNA from complex biological fluids and buffer solutions. Focus 12(3):77–78.

Berman, J. S., and Center, D. M. (1987) Chemotactic Activity of Porcine Insulin for Human T Lymphocytes in Vitro. Journal of Immunology, 138:2100.

Burke, D. R., Rossi, J. M., Leung, J., Koos, D. S., Tilghman, S. M. (1991) A mouse genomic library of yeast artificial chromosome clones. Mammal. Genome 1:65.

Carrano, A. V., Gray, J. W., Langlois, R. G., Burkhardt-Schultz, K. J., Van Dilla, M. A. (1979) Measurement and purification of human chromosomes by flow cytometry and sorting. Proce. Natl. Acad. Sci. U.S.A. 76:1382–1384.

Cashmore, A., Szabo, L., Tinko, M., et al. (1985) Import of Polypeptides into Chloroplasts; a Review. Bio/Technology, 3:803–807.

CooOke, A., Tolmie, J. L., et al. (1989) Detection of an Unbalanced Translocation (4;14) in a Mildly-Retarded Father and Son by Flow Cytometry. Hum. Genet. 83:83–87.

Cooke, H. J. and Hindley, J. (1979) Cloning of Human Satellite III DNA: Different Components Are on Different Chromosomes. Nuc. Acids Res. 10:3177–3197.

Cruikshank, W. W., Berman, J. S., Theodore, A. C., Bernardo, J. and Center, D. M. (1987) Lymphokine Activation of T4 & T Lymphocytes and Monocytes. Journal of Immunology, 138:3818.

Czerlinski, G., Senyei, A., and Widder, K. (1978) Magnetic Guidance of Drug Carrying Microspheres. Journal of Applied Physics, 49:3578.

Damha, M. J., Giannaris, P. A., et al. (1990) An Improved Procedure for Derivatization of Controlled-Pore Glass Beads for Solid Phase Oligonucleotide Synthesis. Nucleic Acids Res. 18:3813–3821.

Darzynkievlcz, Z. and Crissman, H. O. (1990) Flow Cytometry, Academic Press, San Diego, Calif.

Dudin, G., Steegmayer, E. W., et al. (1988) Sorting of Chromosomes by Magnetic Separation. Human Genet. 80:111–116.

Dudin, G., Cremer, T., et al. (1987) A Method for Nucleic Acid Hybridization to Isolated Chromosomes in Suspension. Hum. Genet. 76:290–292.

Eicher, E. M., Hale, D. W., Hunt, P. C., Lee, B. K., Tucker, P. K., King, T. R., Eppig, J. T., Washburn, L. L. (1991) The mouse Y* chromosome involves a complex rearrangement, including interstitial positioning of the pseudoautosomal region. Cyto. Cell Genet. 57:221–230.

Eicher, E. M., Hutchison, K. W., Phillips S. J., Tucker, P. K., Lee, B. K. (1989) A repeated segment on the mouse Y chromosome is composed of retroviral-related, Y-enriched and Y-specific sequences. Genetics 122:181–192.

Elsevier, S. M., Ruddle, F. H. (1975) Location of genes coding for 18S+28S ribosomal RNA within the genome of *Mus musculus*. Chromosoma (Berl) 52:219–228.

Gelvin, S. B. and Schilperoort, R. A. (eds) (1988) Plant Molecular Biology Manual, Kluwer Academic Publishers, Boston.

Giaever, I. (1976) Magnetic Separation of Biological Particles. U.S. Pat. No. 3,970,518.

Gibson, T. J., Coulson, A. R., Sulston, J. R., Little, P. F. R. (1987) Lorist 2, a cosmid with transcriptional terminators insulating invector genes from interference by promoters within the insert effect on DNA and cloned insert frequency. Gene. 53:275–281.

Gould, A. P., Brookman, J. J., Strutt, D. I., White, R. A. H. (1990) Targets of homeotic gene control in Drosophila. Nature 48:308–312.

Graba, Y., Aragnol, D., Laurenti, P., Garzino, V., Charmot, D., Berenger, H., Pradel, J. (1992) Homeotic control in Drosophila; the scabrous gene is an in vivo target of Ultrabithorax proteins. EMBO J. 11(9):3375–3384.

Gray, J. W. (1990) Flow Cytogenetics, Academic Press, San Diego, Calif.

Gruissem, W., Greenberg, B. M., Zurawski, G., et al. (1983) Biosynthesis of Chloroplast Transfer RAA in a Spinach Chloroplast Transcription System. Cell, 35:815–828.

Hahn, P. J., Giddings, L., Longo, J., Lane, M. J., Scalzi, J., Hozier, J., (1992) Double-minute chromosomes as megabase cloning vehicles. GATA 9(1):17–25.

Harris, P., Morton, C. C., Guglielmi, P., et al. (1986) Mapping by Chromosome Sorting of Several Gene Probes Including C-myc, to the Derivative Chromosomes of a 3;8 Translocation Associated with Familial Renal Cancer. Cytometry 7:589–594.

Henderson, A. S., Eicher, E. M., Yu, M. T., Atwood, K. C. (1974) The chromosomal location of ribosomal DNA in the mouse. Chromosoma (Berl) 49:155–160.

Hormes, E., Korsnes, L. (1990) Magnetic DNA hybridization properties of oligonucleotide probes attached to superparamagnetic beads and their use in the isolation of poly (A) mRNA from eukaryotic cells. GATA 7(6):145–150.

Howell, K., Gruenberg, J., et al. (1988) Immuno-Isolation of Subcellular Components. In: Morre D. J., et al. (eds.) Cell-Free Analysis of Membrane Traffic. Liss, New York pp. 77–90.

Hunter, J. A. (1982) Ferrography—A New Method for Isolation of Particles from Biological Fluids. Journal of Clinical Pathology, 35:689.

Hutchison, N. J., Langer-Safer, P. R., et al. (1982) In-situ Hybridization at the Electron Microscope Level: Hybrid Detection by Autoradiography and Colloidal Gold. The Journal of Cell Biology 95:609–618.

Ito, T., Smith C. L. and Cantor, C. R. (1992) Sequence specific DNA purification by triplex affinity capture. Proc. Natl. Acad. Sci. U.S.A., 89:495–498.

Jones, K. W., Singh, L. (1985) Snakes and evolution of sex chromosomes. TIG 1(2):55161.

June, C., Ledbetter, J. A., Gillespie, M. M., Lindsten, Tullia and Thompson, C. B. (1987) T-Cell Proliferation Involving the CD28 Pathway is Associated with Cyclosporine-Resistant Interleukin-2 Gene Expression. Molecular and Cell Biology, 7:4473.

Handpal, R. P., Ward, D. C., Weissman, S. M. (1990) Selective enrichment of a large size genomic DNA fragment by affinity capture: an approach for genome mapping. Nucl. Acids. Res. 18(7):1789–1795.

KOch, J. E., Kolvraa, S., Petersen, K. B. Gregersen, N., Bolund, L. (1989) Obligonucelotide-priming methods for the chromosome-specific labelling if alpha satellite DNA in situ. Chromosoma (Berl) 98:259–265.

Kvalheim, G., Fodstad, O., Pihl, A., Nustad, K., Pharo, A., Ugelstad, J., Funderud, S. (1987) Elimination of B-lymphoma cells from human bone marrow: Model experiments using monodisperse magnetic particles coated with primary monoclonal antibodies. Cancer. Res. 47: 846–851.

Lea, T., Vartdol, F., et al. (1985) Magnetic Monosized Polymer Particles for Fast and Specific Fractionation of Human Mononuclear Cells. Scand. J. Immunol. 22:207–216.

Lehman, J. (1990) Brave new biosensors. Biotechnology 8:729–731.

Linette, G. P., Hartzman, R. J., Ledbetter, J. A., June, C. H. (1988) HIV-1-Infected Cells Show a Selective Signaling Defect after Perturbation of CD3/Antigen Receptor. Science, 241:573.

Little, P. F. R. (1990) Gene mapping and the human genome mapping project. Curr. Opinion in Cell Biol. 2:478–484.

Maniatis, T., Fritsch, E. F., Sambrook, J. (1982) Molecular cloning. In: *A Laboratory Manual*. Cold Spring Harbor Press, New York pp. 466–7.

Manning, J., Hershey, N. D., et al. (1975) A New Method for In-Situ Hybridization. Chromosome (Berl.) 55:107–117.

Margel, S., Rembaum, A., and Zisblatt, S. (1979) Polyglutaraldehyde: A New Reagent for Coupling Proteins to Microspheres and for Labeling Cell Surface Receptors. II. Simplified Labeling Method by Means of Non-Magnetic and Magnetic Polyglutaraldehyde Microspheres. Journal of Immunological Methods, 28:341.

Margel, S., Beitler, U. and Ofarim, M. (1982) Polyacrolein Microspheres as a New Tool in Cell Biology. J. Cell Sci. 56:157.

Menz, E. T., Havelick, J., et al. (1986) Magnetic Affinity Chromatography: An Emerging Technique. American Biotechnology Laboratory, September/October.

Merrifield, R. B., et al. (1963) J. Am. Chem. Soc. 85:2149.

Molday, R. S., MacKenzie, D. (1982) Immunospecific ferromagnetic iron-dextran reagents for the labelling and magnetic separation of cells. Immunol. Methods 52:353–367.

Molday, R. S., Rembaum, A., and Yen, S. P. S. (1977) Application of Magnetic Microspheres in Labeling and Separation of Cells. Nature, 268:437.

Morimoto, Y. (1981) Biomedical Applications of Magnetic Fluids II. Journal of Pharmacobio-dynamics, 4:624.

Morimoto, Y. (1983) Magnetic Guidance of Ferro-Colloid Entrapped Emulsion for Site Specific Drug Delivery. The Chemical and Pharmaceutical Bulletin, (Tokyo), 1:279.

Mosbach, K., and Schroder, U. (1979) Preparation and Application of Magnetic Polymers for Targeting of Drugs, FEBS Letters, 112.

Moser, H. E., Dervan, P. B. (1987) Sequence-specific cleavage of double helical DNA by triple helix formation. Science. 238:645–650.

Moyzis, R. K., Albright, K. L., Bartholdi, M. F., Cram, L. S., Deaven, L. L., Hildebrand, C. E., Joste, N. E., Longmire, J. L., Meyne, J. Schwarzacher-Robinson, T. (1987) Human chromosome-specific repetitive sequences: Novel markers for genetic analysis. Chromosoma (Berl) 95:375–386.

Narayanswami, S., Lundgren, K., and Hamkalo, B. A. (1989) Deoxyribonucleic Acid Sequence Mapping on Metaphase Chromosomes by Immunoelectron Microscopy. Scanning Microscopy Supplement 3:65–76.

Narayanswami, S. and Hamkalo, B. A. (1990) High Resolution Mapping of *Xenopus laevis* 5S and Ribosomal RNA Genes by EM In-Situ Hybridization. Cytometry 11:144–152.

Narayanswami, S., Kausch, A. P., Hamkalo, B. A. (1990) Reversible immobilization of in-situ hybridized chromosomes. A new approach to chromosome sorting. Proc. 4th Intl. Workshop on Mouse Genome Mapping.

Narayanswami, S., Doggett, N. A., Clark, L. M., Hildebrand, C. E., Weier, H-U., Hamkalo, B. A. (1992) Cytological and molecular characterization of centromeres in *Mus domesticus* and *Mus spretus*. Mamm. Gen. 2:186–194.

Newbower, R. (1973) Magnetic Fluids in the Blood, IEEE Transactions on Magnetics, MAG.-9, 447.

Padmanabhan, R., Corsico, C. D., Howard, T. H., et al. (1988) Purification of Transiently Transfected Cells by Magnetic Affinity Cell Sorting. Anal. Biochem., 170:341–348.

Pardue, M. L., and Gall, J. G. (1970) Chromosomal Localization of Mouse Satellite DNA. Science 168:1356–1358.

Radic, M. Z., Lundgren, K., Hamkalo, B. A. (1987) Curvature of mouse satellite DNA and condensation of heterochromatin. Cell 50:1101–1108.

Ranney, D. F., Senyei, A. E. and Widder, K. (1979) Magnetically Responsive Microspheres and Other Carriers for the Biophysical Targeting of Antitumor Agnets. Advances in Pharmacological Chemotherapy, 16:213.

Rattner, J. B. and Hamkalo, B. O. (1978) Higher Order Structure in Metaphase Chromosomes. The 250 Å Fiber. Chromosome (Berl.) 69:363–372.

Rembaum, A. and Dreyer, W. J. (1980) Immunomicrospheres: Reagents for Cell Labeling and Separation. Science, 208:364.

Rikke, B. A., Garyin, L. D., Hardies, S. C. (1991) Systematic identification of LINE-1 repetitive DNA sequence differences having species specificity between *Mus spretus* and *Mus domesticus*. J. Mol. Biol. 219:635–643.

Scarpelli, D., Senyei, A. and Widder, K. (1978) Magnetic Microspheres: A Model System for Site Specific Drug Delivery in Vivo. Proceedings of the Society for Experimental Biology and Medicine, 58:141.

Schmid, M., Vitelli, L., Batistoni, R. (1987) Chromosome banding in Amphibia. Chromosoma (Berl) 95:271–284.

Schreiber, P. H., Reiss, B. and Kuntz, M. (1988) Subcellular Targeting of Proteins In Vivo and In Vitro. In Gelvin and Schilperoort, pp. 1–22.

Schroeder, U., Segren, S., Gemmefors, C., et al. (1986) Magnetic Carbohydrate Nonparticles for Affinity Cell Separation. J. of Immunol. Methods 93:45–53.

Senyei, A. E. and Widder, K. (1981) Drug Targeting: Magnetically Responsive Albumin Microspheres—A Review of the System to Date. Gynecology and Oncology, 12:1.

Sherwood, J. K., Dause, R. B., and Saltzman, W. M., BIO/TECHNOLOGY, 10, 1446–1449, (1992))

Spangrude, G. J., Heimfeld, S. and Weissman, I. L. (1988) Purification and Characterization of Mouse Hematopoietic Stem Cells. Science, 241:58–62.

Staros, J. V. (1982) Nihydroxysulfosuccinimide active esters: Bis (N-hydroxysulfosuccinimide) esters of two dicarboxylic acids are hydrophilic, membrane impermeant protein crosslinkers. Biochemistry 21:3950–3955.

Sternberg, N. L. (1992) Cloning high molecular weight DNA fragments by the bacteriophage P1 system. TIG. 8(1):11–16.

Strause, W. M., Jaenisch, R. (1992) A strategy for rapid production and screening of yeast artificial chromosome libraries. Mamm. Gen. 2:150–157.

Stuart, W. D., Porter, D. L. (1978) An improved in situ hybridization method. Exp. Cell Res. 113:219–222.

Sugibayashi, K. (1982) Biomedical Applications of Magnetic Fluids. Biomaterials.

Trendelenburg, M. F., Gurdon, J. B. (1978) Transcription of cloned Xenopus ribosomal genes visualized after injection into oocyte nuclei. Nature. 276:292–294.

Uhlen, M. (198D) Magnetic Separation of DNA. Nature 340:733–734.

Van Dilla, M. A., Deaven, L. L. (1989) Construction of gene libraries for each human chromosome. Cytometry. 11:208–218.

Viegas-Pequignot, E. Dutrillaux, B. et al. (1989) Mapping of Single-Copy DNA Sequences on Human Chromosomes by In-Situ HybridizatiOn with Biotinylated Probes: Enhancement of Detection Sensitivity by Intensified-Fluorescence Digital-Imaging Microscopy. Proc. Natl. Acad. Sci. U.S.A. 86:582–586.

Waye, J. S., Durfy, S. J., Pinkel, D., et al. (1987) Chromosome-Specific Alpha Satellite DNA from Human Chromosome 1: Hierarchical Structure and Genomic Organization of a Polymorphic Domain Spanning Several Hundred Kilobase Pairs of Centromeric DNA. Genomics 1:43–51.

Weber, J., Weith, A., Kaiser, R., Grzeschik, K. E., Olek, K. (1990) Microdissection and Microcloning of Human Chromosome 7q22–32 Region. Somat. Cell and Mol. Genet. 16(2):123–128.

Wilchek, M. and Boyer (eds) E. A. (1990) Avidin-Biotin Technology, v. 184, Academic Press, San Diego, Calif.

Wong, A. K. C., Biddle, F. G., Rattner, J. B. (1990) The chromosomal distribution of the major and minor satellite is not conserved in the genus Mus. Chromosoma (Berl) 99:190–195.

Wu, D. and Walters, R. R. (1988) Protein Immobilization of Silica Supports: A Ligand Density Study. J. Chromat. 458:169–174.

What is claimed is:

1. A method for reversibly anchoring a biological material to a solid support comprising the steps of:

(a) placing a reversible polymer onto the solid support;

(b) attaching a reversible linker to the polymer; and (c) linking the biological material to the reversible linker with a binding composition, said binding composition comprising a nucleic acid, an antibody, an anti-idiotypic antibody or protein A, to reversibly anchor the biological material to the solid support;

wherein said biological material is a chloroplast, plastid, chromosome, fragment of chromosome, protein or nucleic acid.

2. The method of claim 1, further comprising releasing the biological material.

3. The method of claim 1, wherein said binding composition comprises a label.

4. The method of claim 1, wherein the reversible polymer comprises an alginate, lactide or glycolate polymer.

5. The method of claim 4, wherein the reversible polymer comprises an alginate polymer.

6. The method of claim 1, wherein the nucleic acid molecule binding composition comprises a triple helix forming molecule.

7. The method of claim 3, wherein the binding composition includes a luminescent indicator.

8. The method of claim 7, wherein the luminescent indicator comprises a fluorescent indicator.

9. The method of claim 3, wherein the binding composition comprises magnetic particles.

10. The method of claim 9, wherein the magnetic particles are from about 2 nm to about 10 microns in diameter.

11. The method of claim 10, wherein the magnetic particles are from about 2 nm to about 2 microns in diameter.

12. The method of claim 3, wherein the binding composition comprises colloidal gold.

13. The method of claim 1, wherein the reversible crosslinker is DTSSP, SPDP, SAED, SMPT, DPDPS, DSP, BSOCOES, EGS, APDP, DTBP, BASED or SADP.

14. The method of claim 13, wherein the reversible crosslinker is DTSSP o SPDP.

15. A method for reversibly anchoring a biological material to a solid support comprising the steps of:

(a) placing a reversible polymer onto the solid support;

(b) attaching a reversible linker to the polymer;

(c) linking the biological material to the reversible linker with a binding composition, said binding composition comprising a nucleic acid, an antibody, an anti-idiotypic antibody or protein A, to reversibly anchor the biological material to the solid support;

wherein said biological material is chloroplast, plastid, chromosome, fragment of chromosome, protein or nucleic acid;

(d) releasing the biological material by reversing both the reversible polymer and the reversible crosslinker; and (e) obtaining the biological material obtained therefrom.

16. A kit for reversibly anchoring a biological material to a said support, said kit comprising:

(a) a reversibly polymerizable material;

(b) a linker material; and (c) a container means.

17. The kit of claim 16, further comprising a means of reversing said reversible polymerizable and crosslinker material.

18. The kit of claim 16, further comprising a binding composition.

19. A method for reversibly anchoring a biological material to a solid support comprising the steps of:

(a) placing a polymer that solidifies in the presence of a counter ion onto the solid support;

(b) attaching a reversible linker to the polymer, wherein said linker is reversible by thiol reduction; and (c) linking the biological material to the reversible linker with a binding composition, said binding composition comprising a nucleic acid, an antibody, an anti-idiotypic antibody or protein A, to reversibly anchor the biological material to the solid support;

wherein said biological material is proteins, DNA, RNA, chloroplasts, plastids, chromosomes or fragments of chromosomes.

20. The method of claim 19, further comprising the step of releasing the biological material.

21. The method of claim 20, wherein said releasing is by DTT.

22. The method of claim 19, wherein said reversible polymer comprises an alginate, lactide or glycolate polymer.

23. The method of claim 19, wherein said binding composition further comprises a label.

* * * * *

UNITED STATES PATENT AND TRADEMARK OFFICE
CERTIFICATE OF CORRECTION

PATENT NO. : 5,665,582
DATED : September 9, 1997
INVENTOR(S) : Albert P. Kausch and Sandya Narayanswami It is certified that error appears in the above-identified patent and that said Letters Patent is hereby corrected as shown below:

```
Title page, item [73], insert --The Jackson Laboratory, Bar
Harbor, Maine--.
In claim 14, column 58, line 17, delete "DTSSP o SPDP" and
insert --DTSSP or SPDP-- therefor.
```

Signed and Sealed this

Twenty-ninth Day of September, 1998

Attest:

BRUCE LEHMAN

*Attesting Officer*        *Commissioner of Patents and Trademarks*